(12) United States Patent
Yun et al.

(10) Patent No.: US 8,933,230 B2
(45) Date of Patent: Jan. 13, 2015

(54) PHOSPHORUS-CONTAINING GROUP-SUBSTITUTED QUINOLINE, ITS PREPARATION PROCESS, MEDICAL COMPOSITION CONTAINING THE COMPOUNDS AND APPLICATION

(75) Inventors: Ziwei Yun, Guangdong (CN); Hongtao Wang, Guangdong (CN)

(73) Assignee: Beijing Konruns Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 13/982,180

(22) PCT Filed: Apr. 6, 2011

(86) PCT No.: PCT/CN2011/072456
§ 371 (c)(1),
(2), (4) Date: Aug. 22, 2013

(87) PCT Pub. No.: WO2012/100459
PCT Pub. Date: Aug. 2, 2012

(65) Prior Publication Data
US 2013/0331359 A1    Dec. 12, 2013

(30) Foreign Application Priority Data

Jan. 28, 2011 (CN) .......................... 2011 1 0036623

(51) Int. Cl.
C07D 215/38 (2006.01)
C07F 9/60 (2006.01)
A61K 31/675 (2006.01)
C07F 9/6558 (2006.01)

(52) U.S. Cl.
CPC ................. *C07F 9/60* (2013.01); *A61K 31/675* (2013.01); *C07F 9/65583* (2013.01)
USPC .......................................... 546/153; 514/312

(58) Field of Classification Search
USPC .......................................... 546/153; 514/312
See application file for complete search history.

(56) References Cited

U.S. PATENT DOCUMENTS

2010/0239576 A1    9/2010   Xi

FOREIGN PATENT DOCUMENTS

CN    102093421    6/2011

*Primary Examiner* — D M Seaman
(74) *Attorney, Agent, or Firm* — Stites & Harbison PLLC; Cong Ding

(57) ABSTRACT

Phosphorus-containing group-substituted quinolines of formula (I) are provided in the present invention. The preparation process and application of the compound, and formulation comprising phosphorus-containing group-substituted quinolines are also disclosed. The compounds are protein kinase inhibitor and can be used for treating protein kinase abnormal activity-associated diseases, such as tumor, etc.

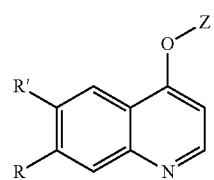

(I)

18 Claims, 2 Drawing Sheets

PHOSPHORUS-CONTAINING GROUP-SUBSTITUTED QUINOLINE, ITS PREPARATION PROCESS, MEDICAL COMPOSITION CONTAINING THE COMPOUNDS AND APPLICATION

TECHNICAL FIELD

The present invention relates to the fields of organic chemistry and medicinal chemistry, particularly relates to a phosphorus-containing group-substituted quinoline, its preparation process, pharmaceutical composition containing the compound and the application.

BACKGROUND ART

Protein kinase is a kind of phosphotransferase, and it has the function of transferring γ-phosphate group of ATP to a specific amino acid residue of a substrate, making a protein phosphorylated and exhibit its physiological and biochemical functions. Protein kinase is a kind of important kinase, and it mainly has the following two functions in signal transduction: on one hand, it regulates the activity of proteins by phosphorylation; on the other hand, it amplifies the signals step by step through protein phosphorylation step by step, thereby causing cell response.

Protein kinase abnormal activity not only closely relates to abnormal state of a certain stage in series of intra- or extracellular signal transduction pathways such as tumor proliferation, apoptosis, metastasis, but also a main cause of incurring series of other human diseases associated with inflammation, or proliferation response, for example, rheumatoid arthritis, cardiovascular and neural system diseases, asthma, psoriasis. It is known by now that there are over 400 kinds of human diseases directly or indirectly related to protein kinase, which makes the protein kinase become another kind of important drug target following the G-protein coupled receptor.

Protein kinase as a big family consists of over 500 members, and is generally classified into two types, i.e., protein tyrosine kinases (PTKs) and serine-threonine kinases. According to the position of kinases in a cell, they are classified into receptor kinases and non-receptor kinases, also called intracellular kinases. The receptor kinases generally belong to tyrosine kinases, also called receptor tyrosine kinases (RTKs), such receptor kinases consist of the portion outside cell membrane, transmembrane domain and the portion in the cytoplasm, the catalytic portion of the kinase is located in the cytoplasm. Most of the serine-threonine kinases are located inside the cell, and belong to non-receptor kinases, or called cytosolic kinases.

The typical representatives of the RTKs family are growth factor receptors, which have at least 19 sub-families, the following are the main sub-families:

(a) HER family receptor tyrosine kinases, which include EGFR (epithelial growth factor receptor), HER2, HER3 and HER4. EGFR is a target of synthetic small-molecule drugs such as Tarceva®, Tykerb® and monoclonal antibody Erbitux® for treating non-small cell lung cancer.

(b) Insulin family consists of insulin receptor (IR), insulin-like growth factor I receptor (IGF-1R) and insulin receptor-related receptor (IRR); wherein IGF-1R is a well-known anticancer target, since it is too similar to IR, particularly the kinase portion inside the cell, their amino acid sequences are 100% identical, inhibition of the activity of IGF-1R generally also inhibits the activity of IR. It is proved that IR is also an effective anticancer target, since the inhibition of IR may have the risk of increasing blood sugar, and it needs to find a balance between efficacy and safe risk for using IR inhibitor as anticancer agent.

(c) Platelet-derived growth factor receptors (PDGFRs) family, which includes PDGFR-α, PDGFR-β, CSF1R, c-KIT and c-fms; wherein c-KIT is a molecule target of leukemia-treating drugs such as Gleevec® and also for treating gastrointestinal stromal tumors.

(d) Vascular endothelial growth factor receptors (VEGFRs) family, which includes FLT1 (Fms-like tyrosine kinase 1 or VEGFR1), KDR (or VEGFR-2) and FLT4 (or VEGFR3). The members among them are molecular target of Sutent® and Naxavar®.

(e) Fibroblast growth factor receptors (FGFRs) family, which includes FGFR1, FGFR2, FGFR3 and FGFR4 and 7 ligands, FGF1, FGF2, FGF3, FGF4, FGF5, FGF6 and FGF7. The members among them are molecular targets of drugs currently undergoing clinical tests.

(f) MET family, which includes c-Met or called human hepatocyte growth factor receptor (hHGFR), and RON; wherein c-Met plays an important role in the growth and metastasis of the initial tumor, drugs targeting the member of MET family are currently in clinical trials.

(g) RET family, RETs are receptors of a member from GDNF family and have isoforms of RET51, RET43 and RET9, drugs targeting the member of RET family are currently in clinical trials.

(h) Eph family, which is the biggest family of receptor tyrosine kinases, consists of 16 receptors (EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6) and 9 ligands (EFNA1, EFNA2, EFNA3, EFNA4, EFNA5, EFNB1, EFNB2, EFNB3). These members play important roles in development of animals, and some of them play roles in tumors.

Non-receptor kinases do not have the portion outside cell membrane and the transmembrane domain, and the whole kinase is in the cytoplasm. By now it is known that there are at least 24 non-receptor kinases, which are divided into 11 subfamilies, i.e. Src, Frk, Btk, CsK, Abl, Zap70, Fes, Fps, Fak, Jak and AcK subfamilies; wherein Src subfamily is the biggest and includes Src, Yes, Fyn, Lyn, Lck, Blk, Hck, Fgr, AUR1, AUR2 and Yrk kinases. For more detailed information, see: Neet, K.; Hunter, T. *Genes to Cells* 1996, 1, 147-169 and the documents cited therein. Although several non-receptor kinases belong to tyrosine kinases, most of the non-receptor kinases belong to serine-threonine kinases; wherein several members of them are molecular targets of leukemia-treating drugs such as Gleevec® and Sprycel®.

As stated above, receptor kinases and non-receptor kinases as antitumor targets have been fully proved in clinical and practical applications, and several antitumor drugs are approved to sale on the markets to be used for patients. in addition to treatment of tumors, inhibiting abnormal activity of receptor kinases and non-receptor kinases may also be used for treating the following diseases, which include, but not limited to: psoriasis, hepatic cirrhosis, diabetes, angiogenesis-related diseases, restenosis-related diseases, eye diseases, age-related macular degeneration, rheumatoid arthritis and other inflammatory diseases, immune system diseases such as autoimmune disease, cardiovascular diseases such as atherosclerosis, or kidney disease etc. Thus it is needed to go on developing desired inhibitors of these kinases.

CONTENTS OF THE INVENTION

One purpose of the present invention is to provide a phosphorus-containing group-substituted quinoline having the activity of inhibiting protein kinase, and the preparation process thereof.

Another purpose of the present invention is to provide use of the above phosphorus-containing group-substituted quinoline in manufacturing of medicaments for treating protein kinase abnormal activity-associated diseases.

Still another purpose of the present invention is to provide a pharmaceutical composition comprising the above phosphorus-containing group-substituted quinoline capable of treating protein kinase abnormal activity-associated diseases.

Technical Solution of the Invention

A phosphorus-containing group-substituted quinoline, which has a molecular structure represented by the following formula (I):

1.

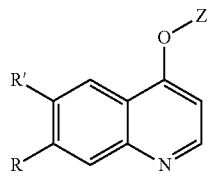

(I)

in which,

Z represents

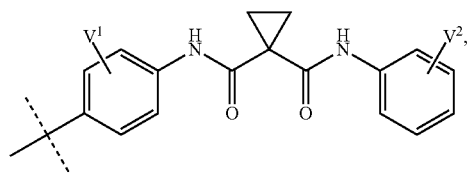

$V^1$ and $V^2$ are each independently selected from hydrogen, halogen, —$OCF_3$, —$CF_3$, —$NO_2$, —CN, —OH, —$NH_2$, —$NMe_2$, $C_{1-6}$ alkyl, $C_{3-6}$ cycloalkyl, $C_{3-6}$ heterocycloalkyl, $C_{1-6}$ alkoxy, $C_{3-6}$ cycloalkoxy, or $C_{3-6}$ heterocycloalkoxy; Either of R and R' represents phosphorus-containing substituent Q, the other is selected from hydrogen, methoxyl, methoxyethoxyl, or phosphorus-containing substituent Q;

Wherein, the phosphorus-containing substituent Q represents

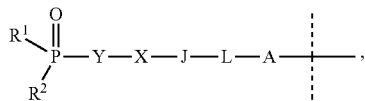

A is absent or represents O, NH, $S(=O)_m$, or $C_{1-6}$ alkyl, and A is optionally substituted with $G^1$;

L is absent or represents $C_{1-6}$ alkyl, $C_{3-6}$ cycloalkyl, $C_6$ aryl, $C_{5-6}$ heteroaryl, or $C_{3-6}$ heterocycloalkyl, and L is optionally substituted with $G^2$;

J is absent or represents O, NH, $S(=O)$, $C_{1-6}$ alkyl, $C_{3-6}$ cycloalkyl, $C_6$ aryl, $C_{5-6}$ heteroaryl, or $C_{3-6}$ heterocycloalkyl and J is optionally substituted with $G^3$;

X is absent or represents —$C(=O)$—, —$S(O)_m$—, $C_{1-6}$ alkyl, $C_{3-6}$ cycloalkyl, $C_6$ aryl, $C_{5-6}$ heteroaryl, or $C_{3-6}$ heterocycloalkyl, and X is optionally substituted with $G^4$;

Y is absent or represents $C_{1-6}$ alkyl, $C_{3-6}$ cycloalkyl, $C_6$ aryl, $C_{5-6}$ heteroaryl, or $C_{3-6}$ heterocycloalkyl, and Y is optionally substituted with $G^5$;

$R^1$ and $R^2$ are each independently selected from —OH, $C_{1-6}$ alkyl, $C_{3-6}$ cycloalkyl, $C_6$ aryl, $C_{5-6}$ heteroaryl, $C_{3-6}$ heterocycloalkyl, $C_{1-6}$ alkoxy, $C_{3-6}$ cycloalkoxy, $C_6$ aryloxy, $C_{5-6}$ heteroaryloxy, or $C_{3-6}$ heterocycloalkoxy, and $R^1$ and $R^2$ are each optionally substituted with $G^6$; $R^1$ and $R^2$ together with the phosphorus atom to which they are attached may form a $C_{3-6}$ heterocycloalkyl ring, this $C_{3-6}$ heterocycloalkyl ring may further comprise heteroatom(s) selected from O, N, or $S(=O)_m$;

wherein, $G^1, G^2, G^3, G^4, G^5$ and $G^6$ are each independently selected from H, —CN, —$CF_3$, —$CO_2H$, halogen, $C_{1-6}$ alkyl, $C_{3-6}$ cycloalkyl, $C_{2-6}$ alkenyl, $C_{2-6}$ alkynyl, $C_6$ aryl, $C_{5-6}$ heteroaryl, $C_{3-6}$ heterocycloalkyl, $R^3O$—, $R^3R^4N$—, $R^3S(=O)_m$—, $R^3R^4NS(=O)_m$—, $R^5C(=O)$—, $R^3R^4NC(=O)$—, $R^3OC(=O)$—, $R^5C(=O)O$—, $R^3R^4NC(=O)O$—, $R^5C(=O)NR^3$—, $R^3R^4NC(=O)NR^6$—, $R^3OC(=O)NR^6$—, $R^3S(=O)_mNR^6$—, $R^3R^4NS(=O)_mNR^6$—, $R^3R^4NC(=NR^7)NR^6$—, $R^3R^4NC(=CHNO_2)NR^6$—, $R^3R^4NC(=N-CN)NR^6$—, $R^3R^4NC(=NR^7)$—, $R^3S(=O)(=NR^7)NR^6$—, or $R^3R^4NS(=O)(=NR^7)$—;

$R^3, R^4, R^5, R^6$ and $R^7$ are each independently selected from H, $C_{1-6}$ alkyl, $C_{3-6}$ cycloalkyl, $C_6$ aryl, $C_{5-6}$ heteroaryl, or $C_{3-6}$ heterocycloalkyl; when $R^3$ and $R^4$ are attached to the same nitrogen atom, $R^3$ and $R^4$ together with the nitrogen to which they are attached may form a $C_{3-6}$ heterocycloalkyl ring, this $C_{3-6}$ heterocycloalkyl ring may further comprise heteroatom(s) selected from O, N, or $S(=O)_m$; and $R^3, R^4, R^5, R^6$ and $R^7$ may be optionally substituted with halogen, CN, $C_{1-6}$ alkyl, or $C_{3-6}$ cycloalkyl;

m=0-2.

Provided herein is a phosphorus-containing group-substituted quinoline represented by formula (Ia) below:

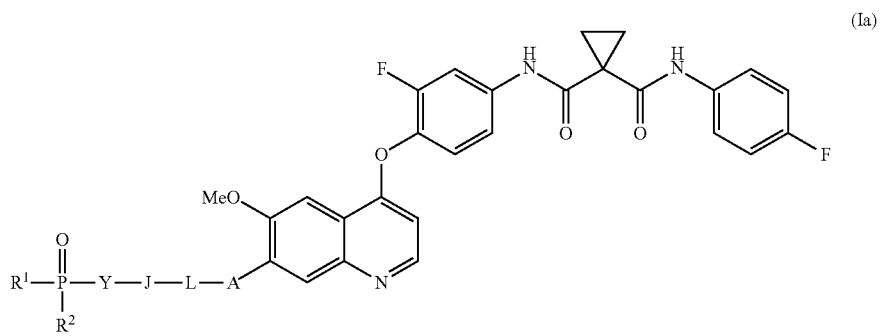

(Ia)

in the above formula,

A represents O, NH, or S(=O)$_m$, and A is optionally substituted with G$^1$;

L represents C$_{1-6}$ alkyl, or C$_{3-6}$ cycloalkyl, and L is optionally substituted with G$^2$;

J represents O, NH, or S(=O)$_m$, and J is optionally substituted with G$^3$;

Y represents C$_{1-6}$ alkyl, or C$_{3-6}$ cycloalkyl, and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;

m=0-2.

A phosphorus-containing group-substituted quinoline is represented by formula (Ib) below:

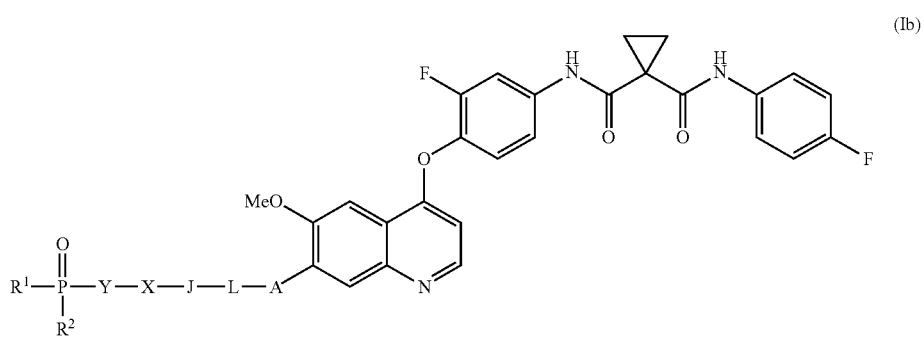

(Ib)

in the above formula,

A represents O, NH, or S(=O)$_m$, and A is optionally substituted with G$^1$;
L represents C$_{1-6}$ alkyl, and L is optionally substituted with G$^2$;
J represents C$_{3-6}$ cycloalkyl, or C$_{3-6}$ heterocycloalkyl, and J is optionally substituted with G$^3$;
X is absent or represents —C(=O)—, or —S(O)$_m$—;
Y represents C$_{1-6}$ alkyl, or C$_{3-6}$ cycloalkyl; and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;
m=0-2.

A phosphorus-containing group-substituted quinoline is represented by formula (Ic) below:

i.

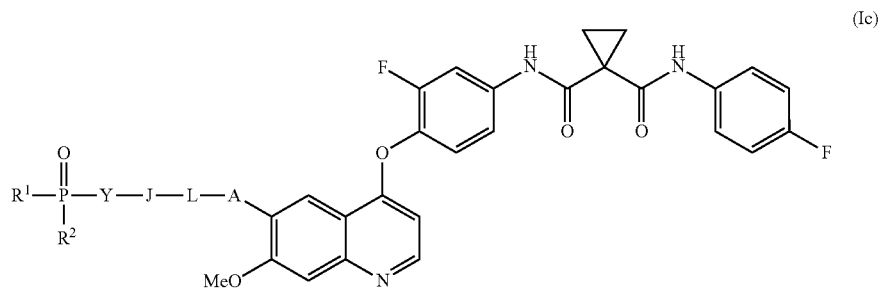

(Ic)

in the above formula,
A represents O, NH, or S(=O)$_m$, and A is optionally substituted with G$^1$;
L represents C$_{1-6}$ alkyl, or C$_{3-6}$ cycloalkyl, and L is optionally substituted with G$^2$;
J represents O, NH, or S(=O)$_m$, and J is optionally substituted with G$^3$;
Y represents C$_{1-6}$ alkyl, or C$_{3-6}$ cycloalkyl, and Y is optionally substituted with G$^5$;
R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;
m=0-2.

Provided herein is a phosphorus-containing group-substituted quinoline represented by formula (Id) below:

i.

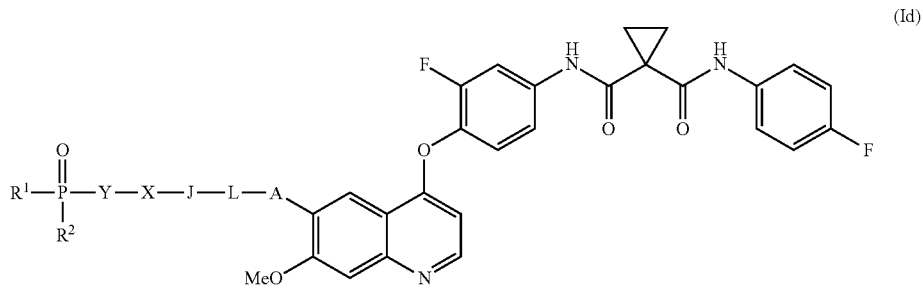

(Id)

in the above formula,

A represents O, NH, or S(=O)$_m$, and A is optionally substituted with G$^1$;

L represents C$_{1-6}$ alkyl, and L is optionally substituted with G$^2$;

J represents C$_{3-6}$ cycloalkyl, or C$_{3-6}$ heterocycloalkyl, and J is optionally substituted with G$^3$;

X is absent or represents —C(=O)—, or —S(O)$_m$—;

Y represents C$_{1-6}$ alkyl, or C$_{3-6}$ cycloalkyl, and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;

m=0-2.

Provided herein is a phosphorus-containing group-substituted quinoline represented by formula (Ie) below:

i.

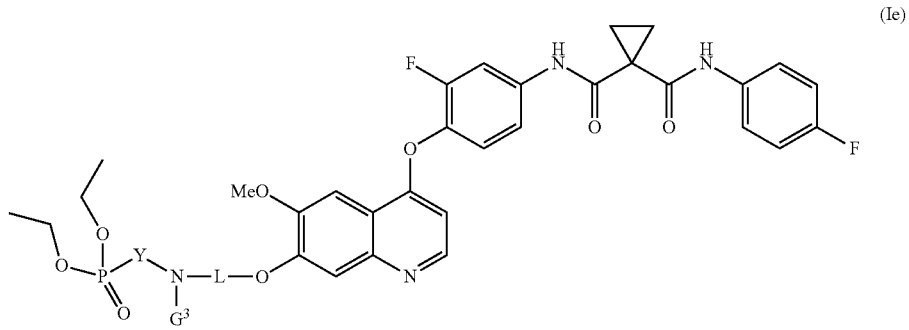

(Ie)

in the above formula,

L represents C$_{1-6}$ alkyl, or C$_{3-6}$ cycloalkyl, and L is optionally substituted with G$^2$;

Y represents C$_{1-6}$ alkyl, or C$_{3-6}$ cycloalkyl, and Y is optionally substituted with G$^5$.

A phosphorus-containing group-substituted quinoline is represented by formula (If) below:

ii.

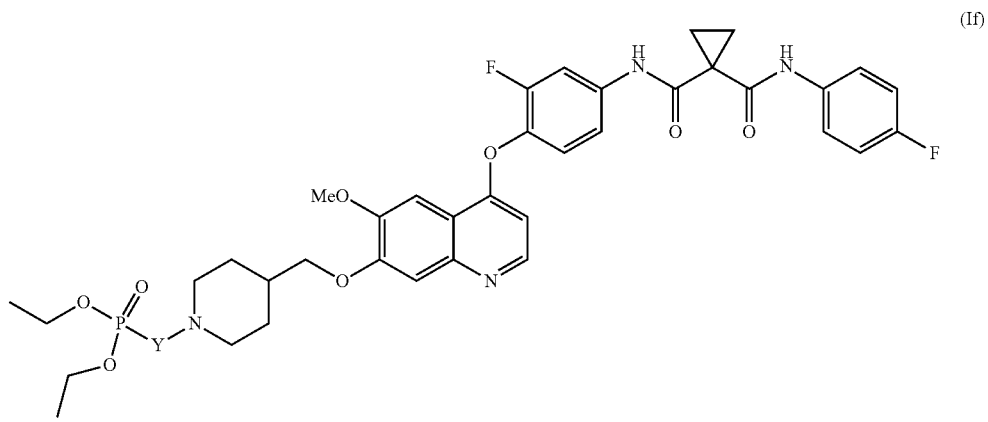

(If)

in the above formula,

Y represents $C_{1-6}$ alkyl, or $C_{3-6}$ cycloalkyl, and Y is optionally substituted with $G^5$.

The phosphorus-containing group-substituted quinoline is selected from the group consisting of one or more of the following compounds:

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethylamino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(methyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(n-propyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(methyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(n-propyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(acetyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(formyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(propionyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(isopropionyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(cyclopropylformyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(acetyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(formyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(propionyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(isopropionyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(cyclopropylformyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1'-[4-[[7-[3-(aminocarbonyl(diethoxyphosphorylmethyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(ethylaminocarbonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(methylaminocarbonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(N,N'-dimethylaminocarbonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(aminocarbonyl(diethoxyphosphorylmethyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(ethylaminocarbonyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(methylaminocarbonyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(N,N'-dimethylaminocarbonyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(methylsulfonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(ethylsulfonyl)amino)propoxyl]-6-methoxyl-4-quinolyl]oxyl]-3-fluorophenyl]-N1-(4-fluorophenyl)cyclopropane-1,1-dicarboxamide;

N1-[4-[[6-[3-(diethoxyphosphorylmethylamino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethylamino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(methyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(ethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(n-propyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(ethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(methyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(ethyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(n-propyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(ethyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(acetyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(formyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(propionyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(isopropionyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(cyclopropylformyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(acetyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(formyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(propionyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(isopropionyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(cyclopropylformyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide;

N1'-[4-[[6-[3-(aminocarbonyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide;

N1'-[4-[[6-[3-(diethoxyphosphorylmethyl)(ethylaminocarbonyl)amino)propoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(methylaminocarbonyl)amino)propoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(N,N'-dimethylaminocarbonyl)amino)propoxyl]-7-methoxyl-4-quinolyl]oxyl]-3-fluorophenyl]-N1-(4-fluorophenyl)cyclopropane-1,1-dicarboxamide;

N1'-[4-[[6-[3-(aminocarbonyl(diethoxyphosphorylmethyl)amino)ethoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(ethylaminocarbonyl)amino)ethoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(methylaminocarbonyl)amino)ethoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(N,N'-dimethylaminocarbonyl)amino)ethoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(methylsulfonyl)amino)propoxyl]-7-methoxyl-4-quinolyl]oxyl]-3-fluorophenyl]-N1-(4-fluorophenyl)cyclopropane-1,1-dicarboxamide;

N1'-[4-[[6-[3-(diethoxyphosphorylmethyl)(ethylsulfonyl)amino)propoxyl]-7-methoxyl-4-quinolyl]oxyl]-3-fluorophenyl]-N1-(4-fluorophenyl)cyclopropane-1,1-dicarboxamide;

N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide;

N1-[4-[[7-[[1-(2-diethoxyphosphorylacetyl)-4-piperidinyl]methoxyl]-6-methoxyl-4-quinolyl]oxyl]-3-fluorophenyl]-N1'-(4-fluorophenyl)cyclopropane-1,1-dicarboxamide;

N1-[4-[[6-[[1-(diethoxyphosphorylmethyl)-4-piperidinyl]methoxyl]-7-methoxyl-4-quinolyl]oxyl]-3-fluorophenyl]-N1'-(4-fluorophenyl)cyclopropane-1,1-dicarboxamide;

N1-[4-[[6-[[1-(2-diethoxyphosphorylacetyl)-4-piperidinyl]methoxyl]-7-methoxyl-4-quinolyl]oxyl]-3-fluorophenyl]-N1'-(4-fluorophenyl)cyclopropane-1,1-dicarboxamide.

A phosphorus-containing group-substituted quinoline, which is selected from the group consisting of one or more of the following compounds:

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphoryl(N-methyl)methylamino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(acetyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[[1-(2-diethoxyphosphorylacetyl)-4-piperidinyl]methoxyl]-6-methoxyl-4-quinolyl]oxyl]-3-fluorophenyl]-N1'-(4-fluorophenyl)cyclopropane-1,1-dicarboxamide;

N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide.

A racemate or enantiomer of a phosphorus-containing group-substituted quinoline.

Provided herein is a preparation process of the phosphorus-containing group-substituted quinoline, consisting of the steps in the following Scheme 1:

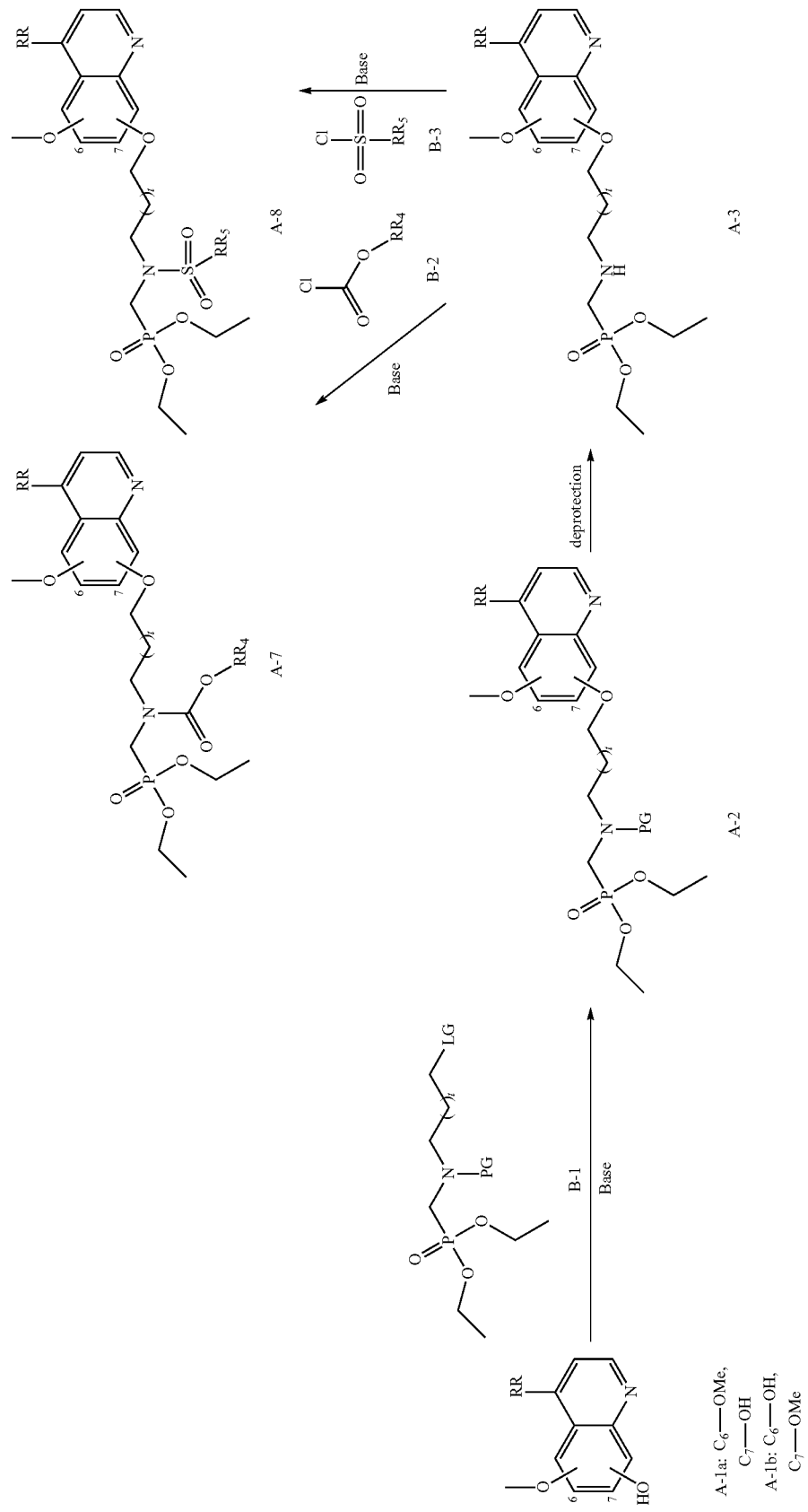

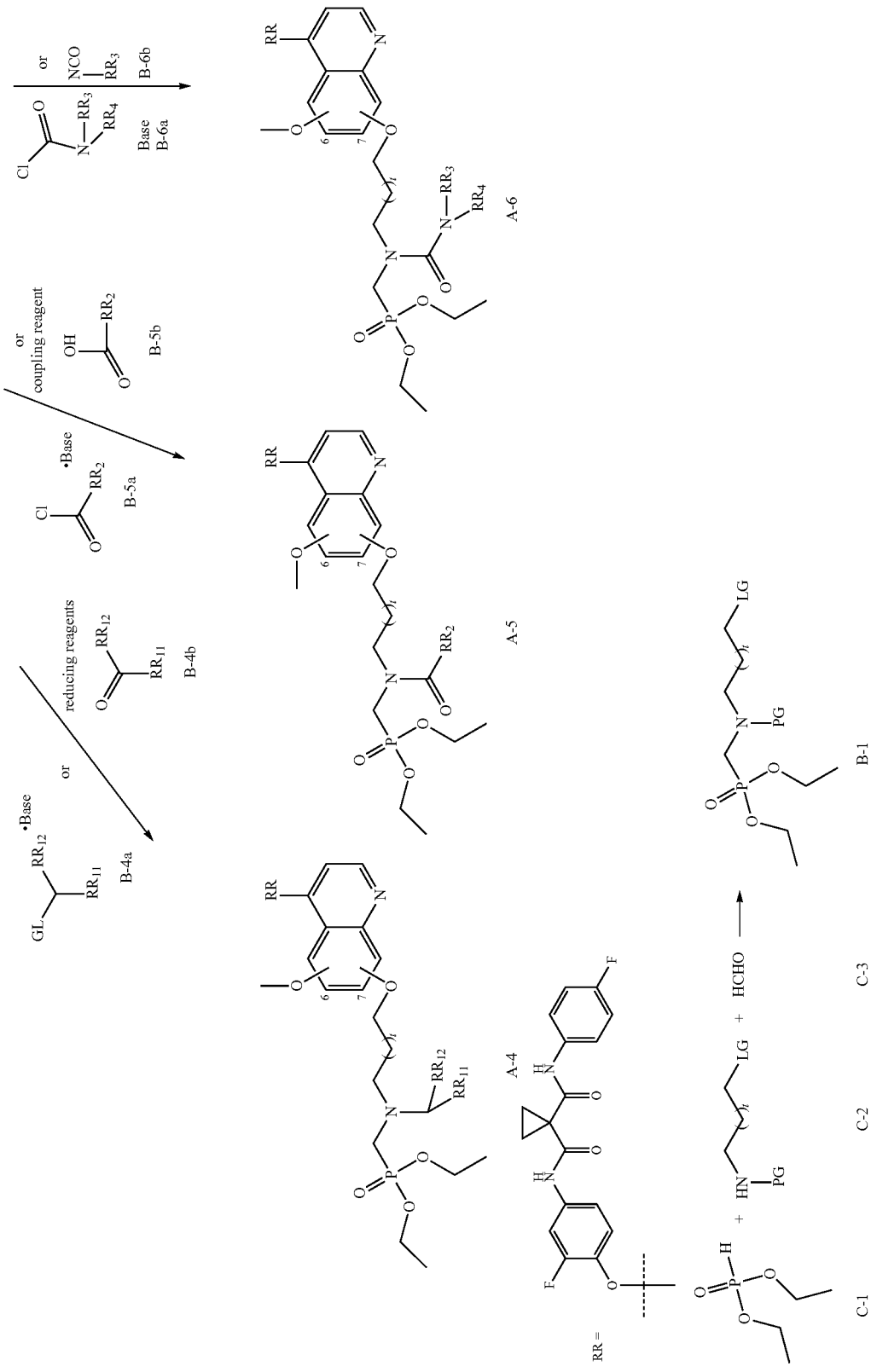

wherein t=0-4;

LG or GL represents common leaving groups in the organic chemistry field;

PG represents common protecting groups in the organic chemistry field;

$RR_1$, $RR_{11}$, $RR_{12}$, $RR_2$, $RR_3$, $RR_4$, or $RR_5$ is each selected from H, $C_{1-6}$ alkyl, $C_{3-6}$ cycloalkyl, $C_6$ aryl, $C_{5-6}$ heteroaryl, or $C_{3-6}$ heterocycloalkyl, and is optionally substituted with H, —CN, —$CF_3$, —$CO_2H$, halogen, $C_{1-6}$ alkyl, $C_{3-6}$ cycloalkyl, $C_{2-6}$ alkenyl, $C_{2-6}$ alkynyl, $C_6$ aryl, $C_{5-6}$ heteroaryl, $C_{3-6}$ heterocycloalkyl, $R^3O$—, $R^3R^4N$—, $R^3S(=O)_m$—, $R^3R^4NS(=O)_m$—, $R^5C(=O)$—, $R^3R^4NC(=O)$—, $R^3OC(=O)$—, $R^5C(=O)O$—, $R^3R^4NC(=O)O$—, $R^5C(=O)NR^3$—, $R^3R^4NC(=O)NR^6$—, $R^3OC(=O)NR^6$—, $R^3S(=O)_mNR^6$—, $R^3R^4NS(=O)_mNR^6$—, $R^3R^4NC(=NR^7)NR^6$—, $R^3R^4NC(=CHNO_2)NR^6$—, $R^3R^4NC(=N—CN)NR^6$—, $R^3R^4NC(=NR^7)$—, $R^3S(=O)(=NR^7)NR^6$—, or $R^3R^4NS(=O)(=NR^7)$), wherein $R^3$, $R^4$, $R^5$, $R^6$ and $R^7$ are each independently selected from hydrogen, $C_{1-6}$ alkyl, $C_{3-6}$ cycloalkyl, $C_6$ aryl, $C_{5-6}$ heteroaryl, or $C_{3-6}$ heterocycloalkyl; when $R^3$ and $R^4$ are attached to the same nitrogen atom, $R^3$ and $R^4$ together with the nitrogen to which they are attached may form a $C_{3-6}$ heterocycloalkyl ring, this $C_{3-6}$ heterocycloalkyl ring may further comprise heteroatom(s) selected from O, N, $S(=O)_m$; and $R^3$, $R^4$, $R^5$, $R^6$ and $R^7$ are each optionally substituted with halogen, CN, $C_{1-6}$ alkyl, or $C_{3-6}$ cycloalkyl; m=0-2.

Provided herein is a preparation process of the phosphorus-containing group-substituted quinoline, consisting of the steps in the following Scheme 2:

Scheme 2

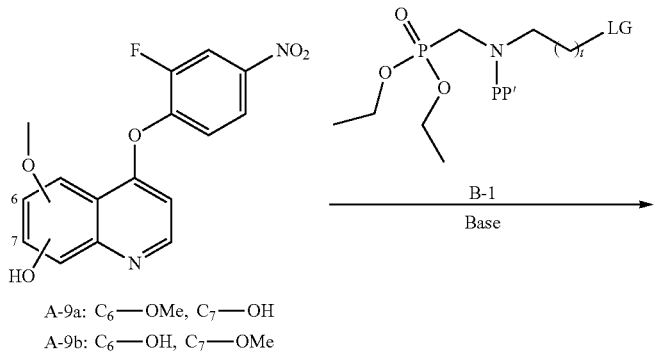

A-9a: $C_6$—OMe, $C_7$—OH
A-9b: $C_6$—OH, $C_7$—OMe

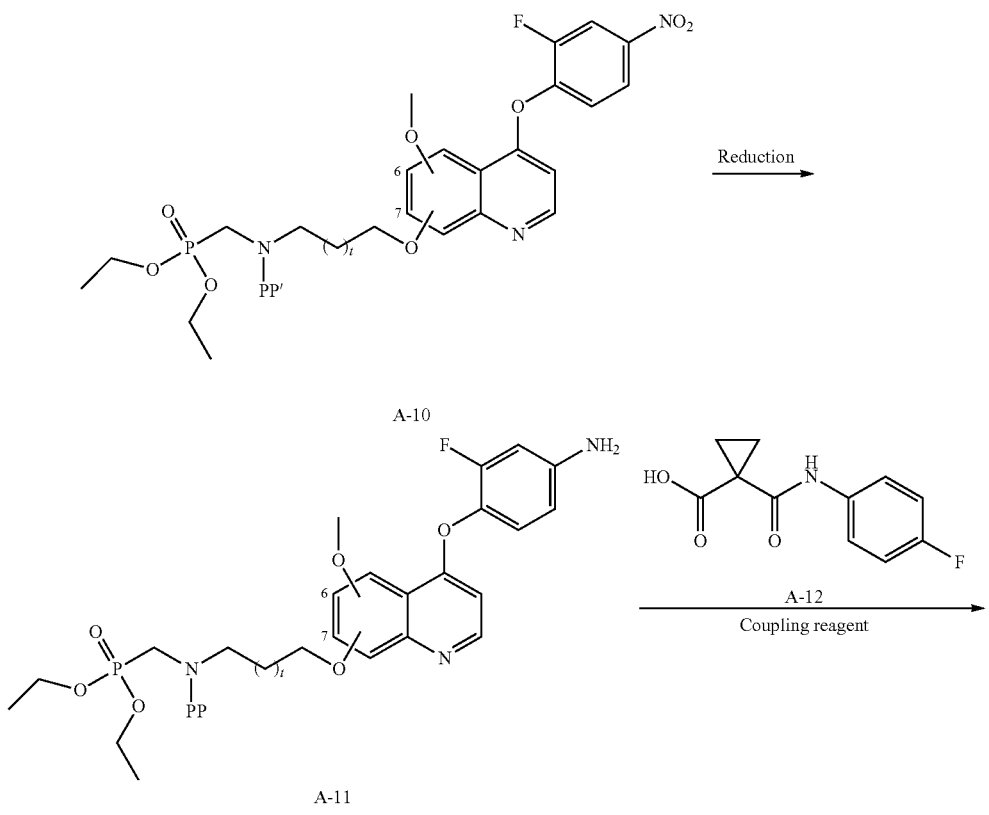

-continued
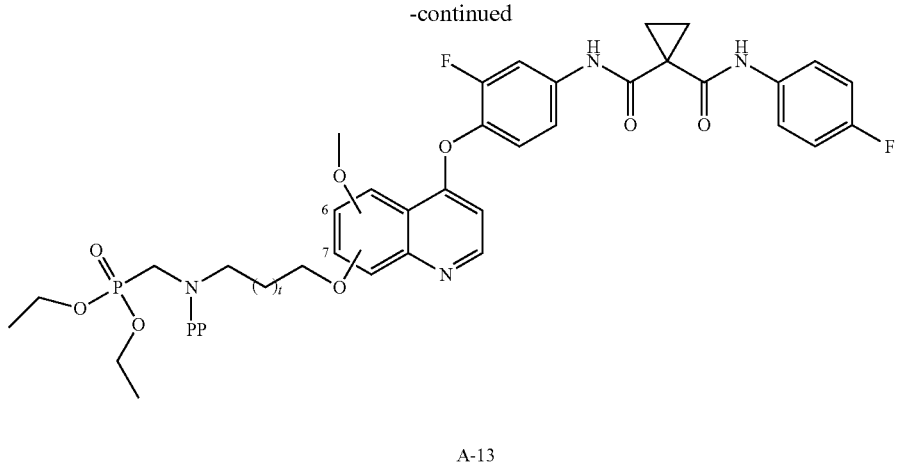
A-13
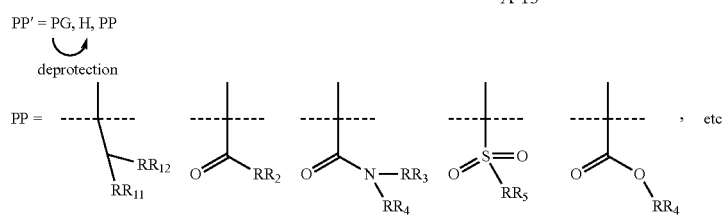
wherein
PP' can be any one of PG, H and PP, and PG can be converted into H by deprotection.
Provided herein is preparation process of the phosphorus-containing group-substituted quinoline, consisting of the steps in the following Scheme 3:
Scheme 3
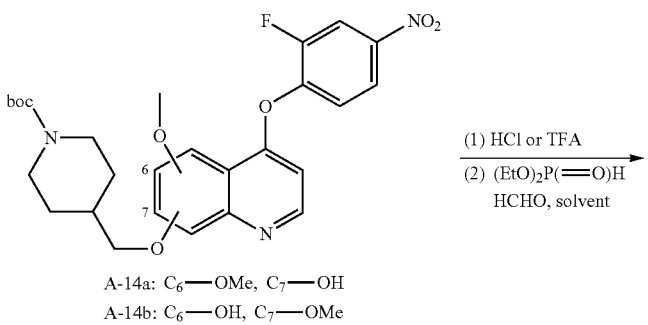
A-14a: $C_6$—OMe, $C_7$—OH
A-14b: $C_6$—OH, $C_7$—OMe
(1) HCl or TFA
(2) $(EtO)_2P(=O)H$
HCHO, solvent
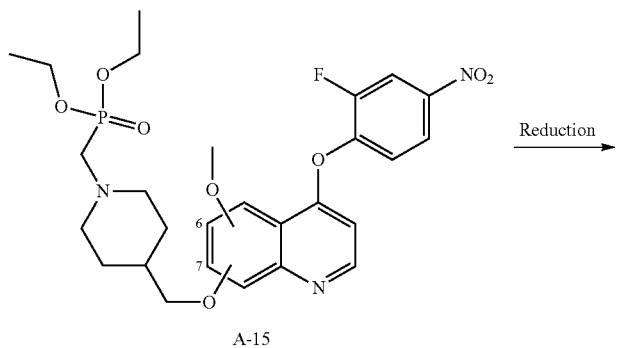
A-15
Reduction

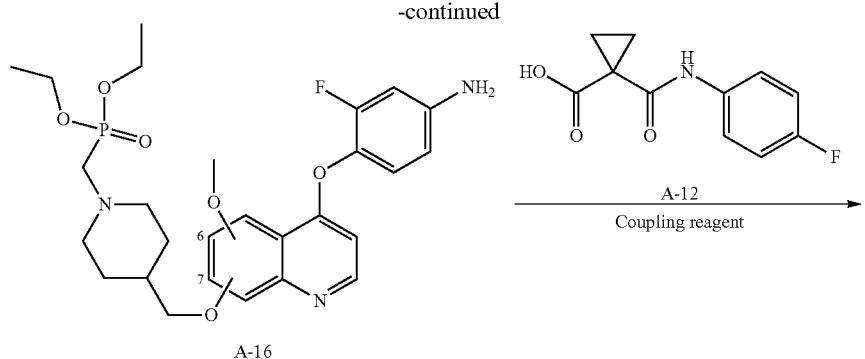
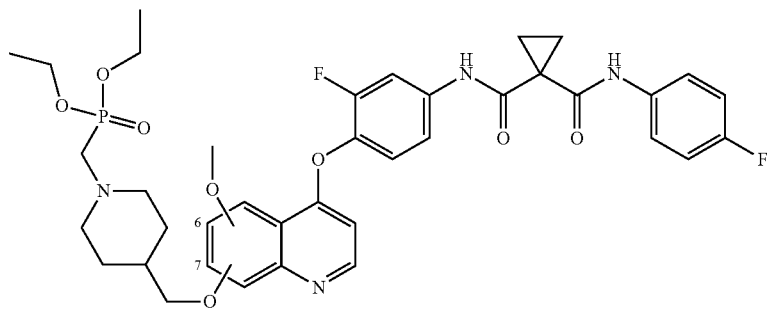
Provided herein is a preparation process of there phosphorus-containing group-substituted quinoline, consisting of the steps in the following Scheme 4:
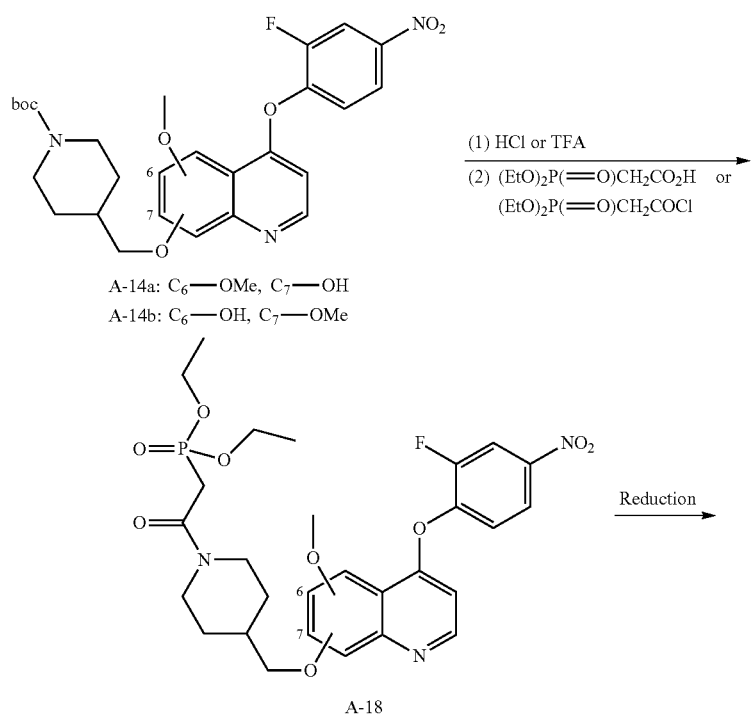

-continued
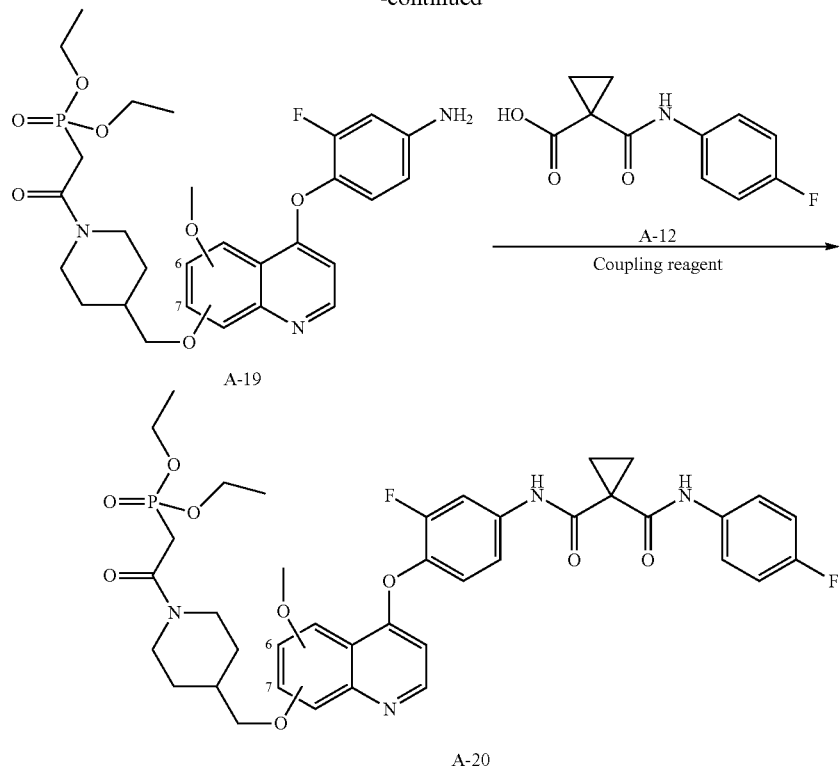
Provided herein is a preparation process of the phosphorus-containing group-substituted quinoline, consisting of the steps in the following Scheme 5:
Scheme 5
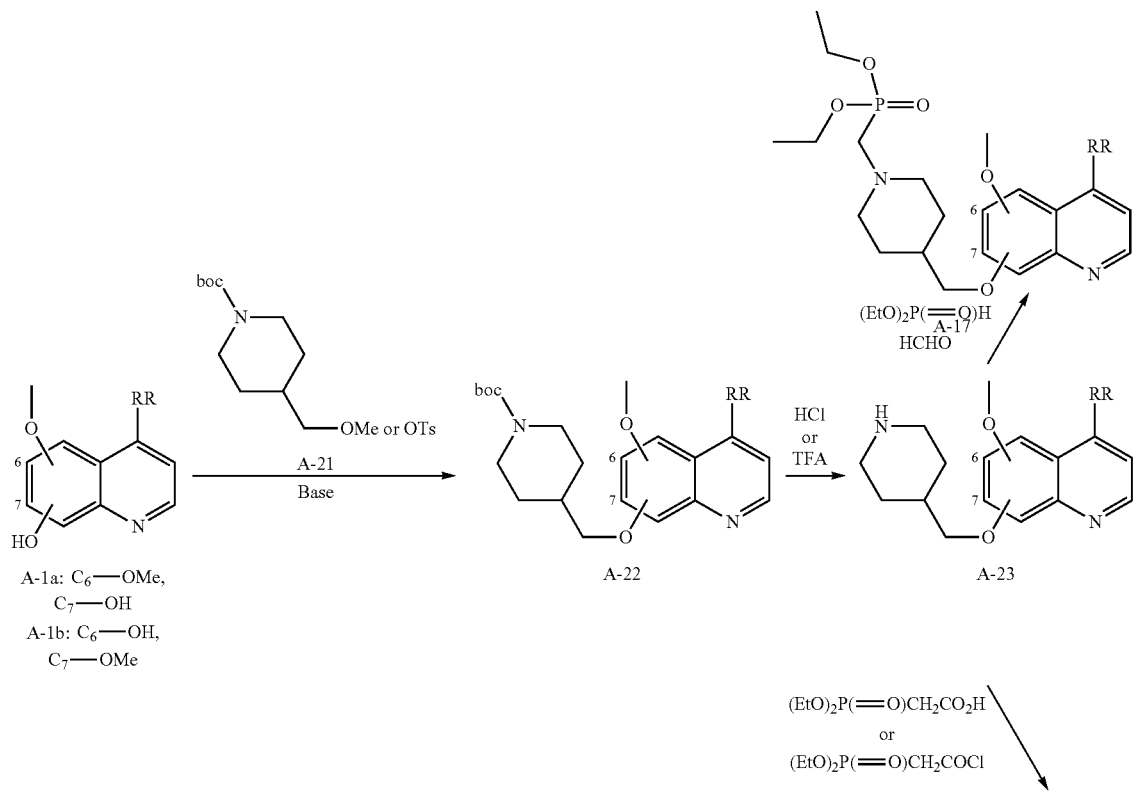

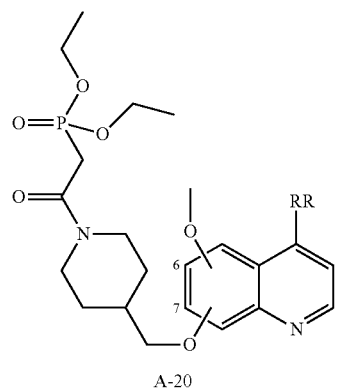

A-20

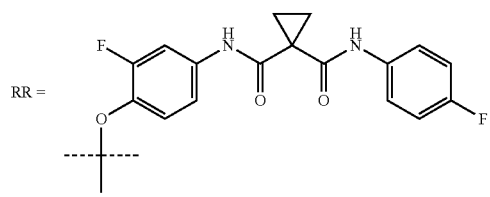

Provided herein is the use of a pharmaceutical composition comprising a phosphorus-containing group-substituted quinoline, wherein the composition is used for treating protein kinase abnormal activity-associated diseases.

Provided herein is the use of a pharmaceutical composition comprising a phosphorus-containing group-substituted quinoline, wherein the protein kinase is c-Met, KDR, or VEGFR2, RET, PDGFR-β, c-KIT, Flt3, MEK5, DDR1, LOK, CSF1R, EPHA7, EPHA8, EPHB6, MKNK2, BLK, HIPK4, HCK, or Flt4.

Provided herein is the use of a pharmaceutical composition comprising a phosphorus-containing group-substituted quinoline, wherein the protein kinase is RON, ALK (or Anaplastic Lymphoma Kinase), EGF1R, HER2, HER3, HER4, PDGFR-α, c-fms, FLT1, Src, Frk, Btk, CsK, Abl, Fes, Fps, Fak, AcK, Yes, Fyn, Lyn, Lck, Hck, Fgr, Yrk, PDK1, TAK1, Tie-2, Tie-1, YSK4, TRK A, TRK B, TRK C, SLK, PKN2, PLK4, MST1R, MAP4K, or DDR2.

Provided herein is the use of a pharmaceutical composition comprising a phosphorus-containing group-substituted quinoline, wherein the disease treated with the composition is psoriasis, hepatic cirrhosis, diabetes, angiogenesis-mediated diseases, eye diseases, immune system diseases, or cardiovascular diseases.

Provided herein is the use of a pharmaceutical composition comprising a phosphorus-containing group-substituted quinoline, wherein the disease treated with the composition is tumor, including solid and liquid tumors.

Provided herein is the use of a pharmaceutical composition comprising a phosphorus-containing group-substituted quinoline, wherein the disease treated with the composition is tumor, including lung cancer, bone cancer, pancreatic cancer, skin cancer, head and neck cancer, skin or intraocular melanoma, uterine cancer, ovarian cancer, rectal cancer, anal region cancer, stomach cancer, colon cancer, breast cancer, fallopian tube cancer, endometrial cancer, cervical cancer, vaginal cancer, vulva cancer, Hodgkin's disease, esophageal cancer, intestinal cancer, endocrine system cancer, thyroid cancer, parathyroid cancer, soft tissue sarcoma, urethral cancer, penile cancer, prostate cancer, chronic or acute leukemia, bladder cancer, kidney or ureter cancer, renal cancer, central nervous system (CNS) tumors, spinal axis tumors, pituitary adenomas, gastrointestinal stromal tumors, colorectal cancer, non-small cell lung cancer, small cell lung cancer, mastocytosis, glioma, sarcoma, lymphoma Provided herein is a medicament for treating protein kinase abnormal activity-associated diseases, which comprises any one of the above compounds or pharmaceutically acceptable salt, solvate, prodrug thereof, or a racemate or enantiomer of any one of the above compounds or pharmaceutically acceptable salt, solvate, prodrug thereof.

The above medicament further comprises at least one pharmaceutically acceptable carrier.

The above medicament is in a form of the following Formulations: (1) oral formulation; (2) injectable formulation; (3) anal suppository; (4) nasal inhalation; (5) eye drop; (6) skin patch.

A series of experiments confirm that, the phosphorus-containing group-substituted quinolines according to the present invention have the following advantages: (1) the screening tests for inhibiting the kinase reveal that, the compound of present invention exhibits strong inhibiting effect on a series of protein kinases and mutants thereof; (2) the tests for inhibiting tumor reveal that, such phosphorus-containing group-substituted quinoline significantly inhibits tumors without apparent toxicity; (3) the compound of the present invention can be used in combination with other anti-tumor drugs and thus obtain synergistic or additive effect; (4) the compound of the present invention can be used together with other tumor therapies, for example, radiotherapy, interventional therapy etc. This shows that a phosphorus-containing group-substituted quinoline according to the invention may be used as a medicament for effective treatment of protein kinase abnormal activity-associated diseases.

In the protein kinase abnormal activity-associated diseases treated by the compound according to the invention, the kidney cancers are adrenal cancer, renal cell carcinoma or carcinoma of renal pelvis; the gliomas are brain stem neuroglioma, neuroendocrine glioma and neuroglioma.

Besides tumor, the protein kinase abnormal activity-associated diseases which the compound of the invention is used to treat further include psoriasis, hepatic cirrhosis, diabetes, angiogenesis-related diseases, restenosis-related diseases, eye diseases such as AMD, rheumatoid arthritis and other inflammatory diseases, immune system diseases such as autoimmune disease (eg. AIDS), cardiovascular diseases such as atherosclerosis, or kidney disease etc.

A pharmaceutical composition comprising the compound of the present invention may be used for treating protein kinase abnormal activity-associated diseases in mammals, such as human patients.

Through a preparation (formulation) process, the compound according to the invention (including racemate, enantiomer and other stereoisomer) or the pharmaceutically acceptable salt, hydrate, solvate or prodrug thereof together with proper pharmaceutically acceptable carriers and commonly used medical auxiliaries may be prepared into a pharmaceutical composition which is favorable for administration.

The routes of administration of the medicament comprising the compound according to the invention may be: (1) oral administration, for example, tablet, capsule etc.; (2) injection, for example, intravenous, subcutaneous, intramuscular, eye injection, intraperitoneal injection etc.; (3), anal plug, for example, suppository, gels etc.; (4), nasal inhalation, for example spray, aerosol etc.; (5) eye drop; (6) skin patch. The drug release system, for example, liposome, slow release techniques etc. also may be used, wherein oral administration and injection are preferably used, particularly oral administration is more preferably used.

The various formulations of the pharmaceutical composition comprising the compound according to the present invention may be prepared by conventional methods in medical industry, for example, mixing, dissolving, granulating, grinding, emuldifying, encapsuling, sugar-coating, freeze-drying, freeze spraying etc.

The content of the compound according to the present invention present in the pharmaceutical composition is in a range of 0.001-100%. The effective amount of the pharmaceutical composition for administrating in mammals including human beings is 0.1-500 mg/per kilogram body weight in each day, preferably in an amount of 1-100 mg/per kilogram body weight in each day. In such an effective amount range, the compound of the present invention exhibits the pharmaceutical actions of inhibiting protein kinase activity and treating protein kinase abnormal activity-associated diseases (for example, cancer).

The administration frequency of the medicament according to the present invention may vary, depending on the used compound or the pharmaceutical composition thereof and the diseases to be treated; the pharmaceutical composition according to the present invention is typically administrated 1-6 times each day, optimized administration frequency is 1-3 times each day.

The packaging and storing of the medicament according to the present invention are similar to those of the general western medicines, for example, the medicament of solid formulation can be directly filled in a bottle made of glass, plastic, paper or metal, desicant is preferably contained in the bottle to maintain the quality of the medicament; generally the medicament of liquid formulation is filled in a bottle made of glass, plastic or metal, or flexible pipe; and the medicament of fogging formulation is generally filled in a overpressure resistant container made of plastic or metal and equipped with pressure-reducing valve etc.

DEFINITION OF TERMS

The following are definitions of the terms mentioned in the present invention. The variable groups used in the present invention, for example $R^a$, $R^b$, m etc. are only applied to this section (i.e., the section of "Definition of Terms").

According to the common knowledge of a person skilled in this field, most of the chemical reactions need to be carried out in a solvent; the commonly used solvents for preparing the compound according to the invention include, but not limited to, water, methanol, ethanol, isopropanol, n-propanol, n-butanol, isobutanol, t-butanol, 2-methoxyethanol, 2,2,2-trifluoroethanol, dichloromethane, 1,2-dichloroethane, chloroform, THF, dioxane, DME, ethyl acetate, diethyl ether, methyl t-butyl ether, hexane, cyclohexane, toluene, acetonitrile, DMF, DMSO, or a mixture of any two or more of the above solvents. In some cases the chemical reactions need to be carried out in the presence of acid or base; the commonly used bases for preparing the compound according to the invention include, but not limited to, $Et_3N$, $Me_3N$, $i-Pr_2NEt$, pyridine, DBU, DABCO, tetramethyl guanidine, NaOH, KOH, $Cs_2CO_3$, $Na_2CO_3$, $K_2CO_3$, $NaHCO_3$, KF, CsF, $K_3PO_4$, $K_2HPO_4$, $KH_2PO_4$, NaH, n-BuLi, s-BuLi, t-BuLi, NaN$(SiMe_3)_2$, LiN$(SiMe_3)_2$, KN$(SiMe_3)_2$, or a mixture of any two or more of the above bases; and the commonly used acids include, but not limited to, $HCO_2H$, AcOH, TFA (trifluoroacetic acid), HCl (hydrochloric acid), $H_2SO_4$, $HNO_3$, $H_3PO_4$, p-TsOH, $PhSO_3H$, CSA, MsOH or Lewis acid such as $ZnCl_2$, $AlCl_3$, $BF_3 \cdot OEt_2$. In some cases the chemical reactions need to be carried out in the presence of coupling reagent; the commonly used coupling reagents for preparing the compound according to the invention include, but not limited to, DCC, EDC, HATU, TBTU, PyBOP, HCTU, BOP, DIC, HOBt, HOAt, CDI, DEPBT etc. In some steps of preparing the compound according to the invention, reduction reaction and reducing reagents are needed; the reducing reagents include, but not limited to, $H_2$+Pd/C, $H_2$+Pd(OH)$_2$, $H_2$+PtO$_2$, $H_2$+Raney Ni, $H_2NNH_2$+Raney Ni, Mg+MeOH, Fe+AcOH, Fe+HCl, Zn+AcOH, Zn+HCl, Zn+NH$_4$OAc, SnCl$_2$, LiAlH$_4$, NaBH$_4$, NaBH$_3$(CN), NaB(OAc)$_3$H, BH$_3$, etc. In some steps of preparing the compound according to the invention, deprotections are needed; when the protecting group is Boc, the commonly used deprotection reagents include, but not limited to, HCl, TFA, $H_2SO_4$ etc.; when the protecting group is CBZ, the commonly used deprotection reagents include, but not limited to, strong HCl, $H_2$+Pd/C etc.; when the protecting group is Bn, the commonly used deprotection reagents include, but not limited to, $H_2$+Pd/C, $H_2$+Pd(OH)$_2$, $H_2$+Pd/C+HCl etc. The reaction for preparing the compound according to the invention is typically carried out at room temperature, however sometimes the temperature needs to be decreased to −78° C. or increased to 200° C.; typically the reaction is carried out at the conditions of the above solvents, and temperatures with conventionally stirring, however sometimes it needs to be carried out in a microwave oven; when the base, reagent, catalyst are sensitive to water or oxygen, the reaction needs to be carried out under the anhydrous and oxygen-free conditions; in such case protonic solvents can not be used.

The term "pharmaceutically acceptable salt" means a salt formed by the reaction of the compound according to the invention with inorganic acid, organic acid, inorganic base, or organic base; the salt has the same or similar biological activity and effectiveness of the compound according to the invention. The inorganic acid or organic acid may be hydrochloric acid, hydrobromic acid, hydroiodic acid, sulfuric acid, nitric acid, carbonic acid, phosphoric acid, perchloric acid, acetic acid, citric acid, oxalic acid, lactic acid, malic acid, salicylic acid, tartaric acid, methanesulfonic acid, ethanesulfonic acid, benzenesulfonic acid, acid substituted benzenesulfonic acid (for example, p-toluene sulfonic acid), isonicotinic acid, oleic acid, tannic acid, pantothenic acid, ascorbic acid, succinic acid, maleic acid, gentisic acid, fumaric acid, gluconic acid, uronic acid, glucaric acid or sugar acid, formic acid, benzoic acid, glutamic acid, pamoic acid, sorbic acid etc.; the inorganic base or organic base may be sodium hydroxide, potassium hydroxide, lithium hydroxide, iron hydroxide, calcium hydroxide, barium hydroxide, aluminum hydroxide, magnesium hydroxide, zinc hydroxide, ammonia, organic quaternary ammonium hydroxide, sodium carbonate, potassium carbonate, lithium carbonate, calcium carbonate, barium carbonate, magnesium carbonate, carbonated organic quaternary ammonium salts, sodium hydrogencarbonate, potassium hydrogencarbonate, lithium hydrogencarbonate, calcium hydrogencarbonate, barium hydrogencarbonate, magnesium hydrogencarbonate, hydrogencarbonated organic quaternary ammonium salt etc.

The term "solvate" means a stable substance formed by the compound according to the invention and a solvent commonly used in chemical reactions through covalent bond, hydrogen bond, ionic bond, van der Waals forces, complexation, inclusion etc.; the solvent may be methanol, ethanol, propanol, butanol, ethylene glycol, propanediol, polyethylene glycol, acetone, acetonitrile, diethyl ether, methyl tert-butyl ether etc.

The term "hydrate" means a solvate, in which the solvent is water.

The term "prodrug" means a compound which is obtained by conversion of the compound of the present invention by chemical synthesis or physical approach and is converted back into the compound according to the present invention in the body of the mammal after it is administrated to a mammal. Usually the "prodrug" approach is used to overcome the poor or bad physicochemical property or druggability of the medical compound itself.

The term "racemate, enantiomer and other stereoisomer" means compounds having the same molecular formula and molecular weight, but they are different due to the different bonding manners between atoms and different space arrangements, such compounds are called isomer or stereoisomer. When these stereoisomers mirror image for each other, i.e. look similar but can not superimpose completely, just like the left hand and right hand; these compounds are called enantiomers. The absolute configurations of enantiomers are typically represented by (R)- and (S)- or R- and S-. Particularly the rules of determining absolute configurations, see Chapter 4 of "Advanced Organic Chemistry," 4$^{th}$ edition (by J. March, John Wiley and Sons, New York, 1992). (R)- and (S)-enantiomers rotate polarized light through opposite angles, i.e. rotating left and rotating right. When (R)- and (S)-enantiomers are mixed or present in a ratio of 1:1, the mixture has no rotating effect on polarized light, such a mixture is called racemate.

The compound according to the invention may have tautomers, rotamers, cis-trans isomers etc., these concepts can be found and understood in "Advanced Organic Chemistry," 4$^{th}$ edition, by J. March. As long as these isomers have the same function of inhibiting the activity of protein kinase as the compound according to the invention, thus these isomers are covered by the present invention.

According to the common knowledge in the art, after the compound of the present invention is administrated to mammals (for example, human beings), it is likely to be metabolized into various metabolites in the body of the mammal by different enzymes, as long as these metabolites have similar function of inhibiting protein kinase activity to that of the compound according to the invention, they are also covered by the present invention.

The term "pharmaceutical composition" means a mixture obtained by mixing one or more of the compounds according to the invention, pharmaceutically acceptable salt or solvate, or hydrate or prodrug thereof with other chemical ingredient (for example pharmaceutically acceptable carrier). The purpose of preparation of a pharmaceutical composition is to facilitate the administration to animals. The above pharmaceutical compositions, besides a pharmaceutically acceptable carrier, may further comprise pharmaceutically commonly used auxiliaries, for example, antibacterial agent, antifungal agent, antimicrobial agent, preservative agent, toner, solubilizer, thickening agent, surfactant, complexing agent, protein, amino acid, fat, carbohydrate, vitamins, minerals, trace elements, sweetening agent, pigment, essence or the combinations thereof.

The term "pharmaceutically acceptable carrier" refers to a non-active ingredients in the pharmaceutical composition, it may be calcium carbonate, calcium phosphate, a variety of sugars (for example lactose, mannitol etc.), starch, cyclodextrin, magnesium stearate, cellulose, magnesium carbonate, acrylic polymer, methyl, acrylic polymer, gel, water, polyenthylene, glycol, propanediol, ethylene glycol, castor oil, hydrogenated castor oil, polyethoxyl hydrogenated castor oil, sesame oil, corn oil, peanut oil etc.

The term "alkyl" means a linear or branched saturated hydrocarbon group having specific number of carbon atoms, for example $C_{1-12}$ alkyl stands for linear or branched groups having 1-12 carbon atoms. $C_0$ alkyl stands for one covalent single bond. As used in the present invention, the alkyl includes, but is not limited to, methyl, ethyl, propyl, butyl, isopropyl, neopentyl, 2-methyl-1-hexyl etc. One or all hydrogen atoms of the alkyl may be substituted with the following groups: cycloalkyl, aryl, heteroaryl, heterocycloalkyl ring, halogen, amino, hydroxyl, cyano, nitro, carboxyl, thio, oxo, alkoxy, aryloxy, alkylthio, arylthio, carbonyl, thiocarbonyl, C-amide, N-amide, O-aminocarbonyloxy, N-aminocarbonyloxy, O-thioaminocarbonyloxy, N-thioaminocarbonyloxy, C-ester, O-ester and —NR$^a$R$^b$, wherein R$^a$ and R$^b$ are respectively selected from hydrogen, alkyl, cycloalkyl, aryl, acetyl, carbonyl, sulfonyl, and trifluoromethylsulfonyl, and R$^a$ and R$^b$ together with the nitrogen atom to which they are attached may form a 5- or 6-member heterocycloalkyl ring.

The term "cycloalkyl" or "cyclic alkyl" stands for a single-, double- or multiple-ring hydrocarbon group having specific number of carbon atoms, in case of double- or multiple-ring, they can be joined together in fused (two adjacent carbon atoms are shared by two or more rings) or spiro (one carbon atoms is shared by two or more rings) manner, for example $C_{1-12}$ cycloalkyl stands for single-, double- or multiple-ring hydrocarbon compound groups having 1-12 carbon atoms. $C_0$ cycloalkyl stands for one covalent single bond. A cycloalkyl may comprise unsaturated double- or triple-bond, but does not have completely conjugated π electronic system. As used in the present invention, the cycloalkyl includes, but not limited to, cyclopropyl, cyclobutyl, cyclohexyl, cyclopentenyl, cycloheptatrienyl, adamantine (examples are shown in Table 1):

TABLE 1

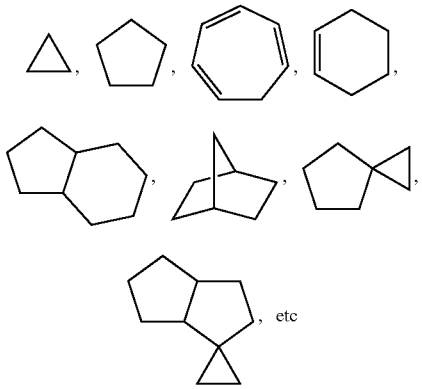

, etc

One or all hydrogen atoms of the cycloalkyl or cycloalkane may be substituted with the following groups: alkyl, aryl, heteroaryl, heterocycloalkyl ring, halogen, amino, hydroxyl, cyano, nitro, carboxyl, thio, oxo, alkoxy, aryloxy, alkylthio, arylthio, carbonyl, thiocarbonyl, C-amide, N-amide, O-aminocarbonyloxy, N-aminocarbonyloxy, O-thioaminocarbonyloxy, N-thioaminocarbonyloxy, C-ester, O-ester and —NR$^a$R$^b$, wherein R$^a$ and R$^b$ are respectively selected from hydrogen, alkyl, cycloalkyl, aryl, acetyl, carbonyl, sulfonyl, trifluoromethylsulfonyl, and R$^a$ and R$^b$ together with the nitrogen atom to which they are attached may form a 5- or 6-member heterocycloalkyl ring.

The term "halogen" stands for fluorine, chlorine, bromine or iodine.

The term "alkoxy" or "alkoxyl" means that an alkyl having specified number of carbon atoms is attached to other group through oxygen atom. As used in the present invention, alkoxy includes, but is not limited to, methoxyl, ethoxyl, propoxy, butoxyl, cyclopentyloxy, cyclohexyloxy, isopropoxy, neopentyloxy, 2-methyl-1-hexyloxy etc.

The term "cycloalkoxy" or "cycloalkoxyl" means that a cycloalkyl having specified number of carbon atoms is attached to other group through oxygen atom. As used in the present invention, cycloalkoxy includes, but not limited to, cyclopropoxy, cyclobutoxy, cyclohexoxy, and the like.

The term "aryl" stands for a single-, double- or multiple-ring group consisting of 6-12 carbon atoms, wherein at least one ring has completely conjugated π electronic system and meets for the Rule N+2, i.e., having aromaticity; but the whole group is not necessary to conjugate completely. An aryl may also be present in form of arylene, i.e., there are two or more atoms attached to other groups in the structure of aryl. As used in the present invention, aryl includes, but is not limited to, phenyl, naphthyl, indenyl, indanyl, tetrahydronaphthalene etc. One or all hydrogen atoms of the aryl may be substituted with the following groups: alkyl, cycloalkyl, heteroaryl, heterocycloalkyl ring, halogen, amino, hydroxyl, cyano, nitro, carboxyl, thio, oxo, alkoxy, aryloxy, alkylthio, arylthio, carbonyl, thiocarbonyl, C-amide, N-amide, O-aminocarbonyloxy, N-aminocarbonyloxy, O-thioaminocarbonyloxy, N-thioaminocarbonyloxy, C-ester, O-ester and —NR$^a$R$^b$, wherein R$^a$ and R$^b$ are respectively selected from the group consisting of hydrogen, alkyl, cycloalkyl, aryl, acetyl, carbonyl, sulfonyl and trifluoromethylsulfonyl, and R$^a$ and R$^b$ together with the nitrogen atom to which they are attached may form a 5- or 6-member heterocycloalkyl ring.

The term "heteroaryl" stands for a single-, double- or multiple-ring group consisting of 5-12 ring atoms other than hydrogens, wherein at least one atom is O, N or S($=$O)$_m$ (wherein m=0-2), and, wherein at least one ring has completely conjugated π electronic system and meets for the Rule N+2, i.e., having aromaticity; but the whole group is not necessary to conjugate completely; for example, C$_5$ heteroaryl stands for an aromatic ring group consisting of 5 ring atoms, wherein at least one ring atom is selected from O, N or S($=$O)$_m$ (wherein m=0-2). A heteroaryl may also be present in form of heteroarylene, i.e., there are two or more atoms attached to other groups in the structure of heteroaryl. As used in the present invention, heteroaryl includes, but not limited to, pyridinyl, pyridinonyl, tetrahydropyridinonyl, pyrimidinyl, pyrazinyl, pyridazinyl, imidazolyl, thiazolyl, thiophenyl, furanyl, indolyl, azaindolyl, benzimidazolyl, indolinyl, indolonyl, quinolinyl etc. (examples are shown in Table 2):

TABLE 2

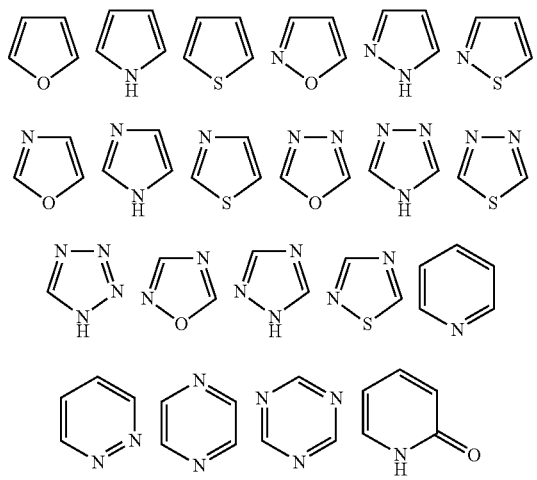

TABLE 2-continued

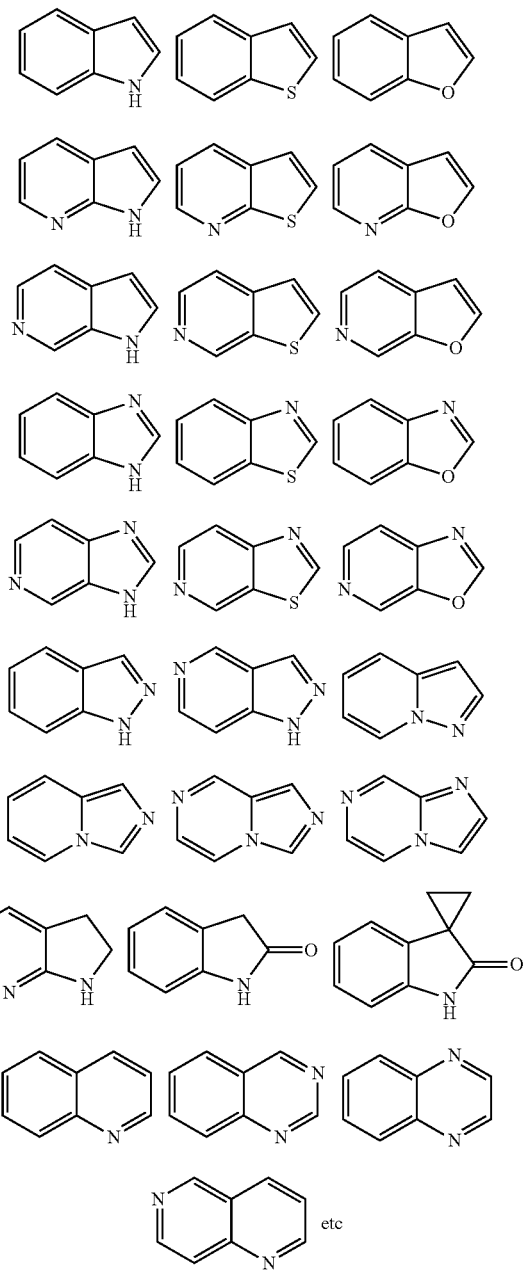

One or all hydrogen atoms of the heteroaryl may be substituted with the following groups: alkyl, cycloalkyl, aryl, heterocycloalkyl ring, halogen, amino, hydroxyl, cyano, nitro, carboxyl, thio, oxo, alkoxy, aryloxy, alkylthio, arylthio, carbonyl, thiocarbonyl, C-amide, N-amide, O-aminocarbonyloxy, N-aminocarbonyloxy, O-thioaminocarbonyloxy, N-thioaminocarbonyloxy, C-ester, O-ester and —NR$^a$R$^b$, wherein R$^a$ and R$^b$ are respectively selected from the group consisting of hydrogen, alkyl, cycloalkyl, aryl, acetyl, carbonyl, sulfonyl, and trifluoromethylsulfonyl, and R$^a$ and R$^b$ together with the nitrogen atom to which they are attached may form a 5- or 6-member heterocycloalkyl ring.

The term "heterocycloalkyl or heterocycloalkyl ring" stands for a single-, double- or multiple-ring alkyl or alkane consisting of 3-12 ring atoms other than hydrogen atoms, wherein at least one atom is O, N or S($=$O)$_m$ (wherein m=0-2), for example, C$_6$ heterocycloalkyl stands for a single ring group consisting of 6 ring atoms, wherein at least one ring atom is selected from O, N or S(=O)$_m$ (wherein m=0-2). Such ring may further comprise double or triple bonds other than single bonds, but these double or triple bonds do not form a aromatic structure. Such single-, double- or multiple-ring alkyls or alkanes may be present in form of fused ring, bridged ring or spiro ring. As used in the present invention, heterocycloalkyl or heterocycloalkyl ring includes, but not limited to, piperidinyl, morpholinyl, piperazinyl, pyrrolidinyl, indolinyl, tetrahydropyridinyl, tetrahydrofuranyl, tropinyl etc. (examples are shown in Table 3):

TABLE 3

[Chemical structures]

One or all hydrogen atoms of the heterocycloalkyl or heterocycloalkyl ring may be substituted with the following groups: alkyl, cycloalkyl, aryl, heteroaryl, heterocycloalkyl ring, halogen, amino, hydroxyl, cyano, nitro, carboxyl, thio, oxo, alkoxy, aryloxy, alkylthio, arylthio, carbonyl, thiocarbonyl, C-amide, N-amide, O-aminocarbonyloxy, N-aminocarbonyloxy, O-thioaminocarbonyloxy, N-thioaminocarbonyloxy, C-ester, O-ester and —NR$^a$R$^b$, wherein R$^a$ and R$^b$ are respectively selected from the group consisting of: hydrogen, alkyl, cycloalkyl, aryl, acetyl, carbonyl, sulfonyl, trifluoromethylsulfonyl, and R$^a$ and R$^b$ together with the nitrogen atom to which they are attached may form a 5- or 6-member heterocycloalkyl ring.

The term "aryloxy" means that an aryl is attached to other group through oxygen atom. As used in the present invention, aryloxy includes, but not limited to, phenoxy, naphthyloxy etc.

The term "heteroaryloxy" means that a heteroaryl is attached to other group through oxygen atom. As used in the present invention, heteroaryloxy includes, but not limited to, 4-pyridinyloxy, 2-thienyloxy etc.

The term "amino" stands for H$_2$N— or H$_2$N— in which hydrogen atoms are substituted, i.e., R$^a$HN— and R$^a$R$^b$N—.

The term "oxo" or "oxyl" stands for =O, i.e., the oxygen is attached to carbon or heteroatoms including N, S, P, through double bond. Examples of substance substituted by oxyl include, but not limited to, those shown in Table 4:

TABLE 4

[Chemical structures]

"Hydroxyl" stands for —OH.
"Nitro" stands for —NO$_2$.
"Carboxyl" stands for —CO$_2$H.
"Thio" stands for —SH.
"Alkylthio" stands for alkyl-S—.
"Arylthio" stands for aryl-S—.
"Carbonyl" stands for —C(=O)—.
"Thiocarbonyl" stands for —C(=S)—.
"C-amide" stands for —C(=O)NR$^a$R$^b$.
"N-amide" stands for C(=O)NR$^a$—.
"O— aminocarbonyloxy" stands for —O—C(=O)NR$^a$R$^b$.
"N— aminocarbonyloxy" stands for O—C(=O)NR$^a$—.
"O— thioaminocarbonyloxy" stands for —O—C(=S)NR$^a$R$^b$.
"N— thioaminocarbonyloxy" stands for O—C(=S)NR$^a$—.
"C— ester" stands for —C(=O)OR$^a$.
"N— ester" stands for C(=O)O—.
"Acetyl" stands for CH$_3$C(=O)—.
"Sulfonyl" stands for —SO$_2$R$^a$.
"Trifluoromethylsulfonyl" stands for CF$_3$SO$_2$—.

SPECIFIC EMBODIMENTS

Figure 1:
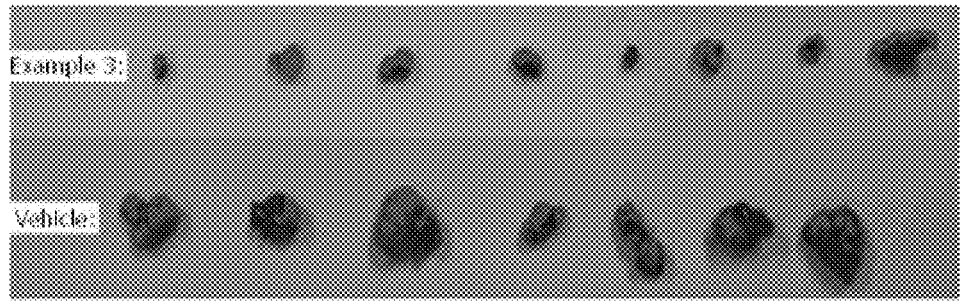
FIG. 1 is a picture of tumors from the GTL-16 xenograft mouse models.

The present invention is further described in the following examples, such that the public may further understand the method of preparing the compound according to the invention and the advantageous effect thereof. But the examples should not be construed as limiting the scope of the present application.

The followings are the abbreviations used in the Examples and their corresponding meanings. If any abbreviation not included in the following list appears in the Examples, it stands for a generally accepted meaning.

DMSO: dimethyl sulfoxide
TMS: tetramethylsilane
DCM: dichloromethane
CDCl$_3$: deuterio-trichloromethane
CD$_3$OD: deuterio-methanol
DME: 1,2-dimethoxyethane
THF: tetrahydrofuran
aq.: aqueous solution
TLC: thin-layer charomatography
LC-MS: liquid chromatography-mass spectrometry
g: gram
mg: milligram
mmol: milimole
μM: micromole
μL: microliter
nM: nanomole
M: molarity
N: normality (equivalent concentration)
m/z: mass-to-charge ratio
δ: chemical shift
DMAP: 4-dimethylaminopyridine
DIPEA: diisopropylethylamine
HATU: 2-(7-azabenzotriazol)-N,N,N',N'-tetramethyluronium hexafluoro-phosphate
EDC.HCl: 1-ethyl-3-(3-dimethylaminopropyl)carbodiimide hydrochloride.

General Experimental Conditions:

The hydrogen and carbon spectra of Nuclear Magnetic Resonance are obtained by using equipment Varian NOVA 500NB or Varian 400 MHz or Bruker 400 MHz (the solvent is deuterio-DMSO, deuterio-trichloromethane, or deuterio-methanol etc, and the internal standard is TMS). Mass spectrum is obtained using Liquid Chromatography-Mass Spectrometer (ESI or APCI ion source ZQ4000, Waters Corporation, USA). Ultraviolet spectrum is measured by UV-3010 ultraviolet spectrophotometer of Hitachi Corporation, Japan. Infrared spectrum is measured by NICOLET6700 infrared spectrometer (KBr discs). High Performance Liquid Chromatography is obtained by Waters 2695 ZORBAX High Performance Liquid Chromatograph (Bx-C$_8$ 5μ 150×4.6 mm Column). Melting point is measured by Electrothermal Digital Melting Point Apparatus IA9100, without correction.

Starting materials, reagents and solvents are commercially available from: Beta-Pharma, Shanghai; Shanghai PI Chemicals; AndaChem, Taiyuan; Shanghai FWD Chemicals; Sigma-Aldrich, Milwaukee, Wis., USA; Acros, Morris Plains, N.J., USA; Frontier Scientific, Logan, Utah, USA; Alfa Aesar, Ward Hill, Mass., USA etc., or synthesized by methods reported in the literature. Unless otherwise indicated, generally a solvent from supplier is directly used without being dried or it is dried by molecular sieve.

Preparation methods of various intermediates (including intermediate A, intermediate B, intermediate C, intermediate D, intermediate F, intermediate G, intermediate H, intermediate I, intermediate J, intermediate K) needed for preparing the compound according to the invention are as follows:

Preparation Method of Intermediate A: 4-(2-fluoro-4-nitrophenoxy)-6-methoxylquinolyl-7-ol

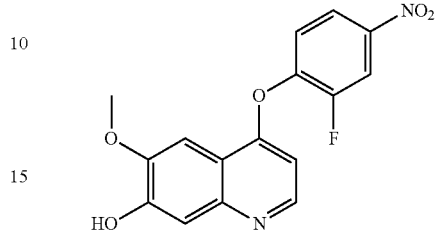

The Intermediate A is prepared according to the method of WO2008/035209, and the analytical data of the resulting product are as follows: $^1$HNMR (400 MHz, DMSO-d$_6$): δ=11.74 (s, br, 1H), 8.76 (d, J=6.8 Hz, 1H), 8.47 (dd, J=2.8 Hz, J=10.4 Hz, 1H), 8.23 (dd, J=1.2 Hz, J=8.8 Hz, 1H), 7.81 (m, 1H), 7.65 (s, 1H), 7.49 (s, 1H), 7.04 (d, J=6.4 Hz, 1H), 3.94 (s, 3H).

Preparation Method of Intermediate B: 4-(2-fluoro-4-nitrophenoxy)-7-methoxylquinolyl-6-ol

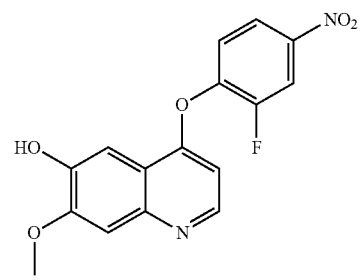 [SMILES: COc1cc2nccc(Oc3ccc([N+](=O)[O-])cc3F)c2cc1O]

The Intermediate B is prepared according to the methods of documents WO2003/033472 and WO2004/039782, and the analytical data of the resulting product are as follows: mass spectrum m/z: 331.12 [M+H].

Preparation Method of Intermediate C: tert-butyl 4-[[4-(4-amino-2-fluorophenoxy)-6-methoxyl-7-quinolyl]oxymethyl]piperidine-1-carboxylate

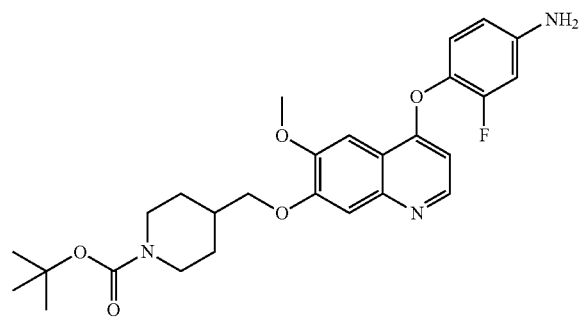 [SMILES: COc1cc2c(Oc3ccc(N)cc3F)ccnc2cc1OCC1CCN(C(=O)OC(C)(C)C)CC1]

The Intermediate C is prepared according to the method of document WO2008/076415, and the analytical data of the resulting product are as follows: mass spectrum m/z: 498.21 [M+H].

Preparation Method of Intermediate D: 1-[(4-fluorophenyl)carbamoyl]cyclopropanecarboxylic acid

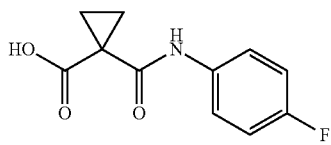

The Intermediate C is prepared according to the method of document WO2005/030140, and the analytical data of the resulting product are as follows: $^1$HNMR (400 MHz, DMSO-$d_6$): δ=13.0 (s, 1H), 10.6 (s, 1H), 7.62-7.57 (m, 2H), 7.15-7.09 (m, 2H), 1.39 (s, 4H).

Preparation Method of Intermediate E: N-benzyl-3-chloro-N-(diethoxyphosphorylmethyl)propan-1-amine

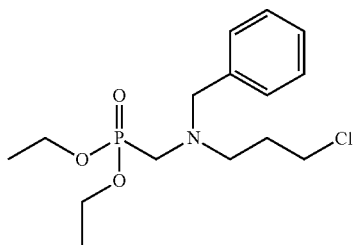 [SMILES: CCOP(=O)(CN(CCCCl)Cc1ccccc1)OCC]

1.6 mL of 37% aqueous formaldehyde solution is added to a suspension of N-benzyl-3-chloropropan-1-amine hydrochloride (7.9 g or 35.9 mmol) in dioxane (60 mL), the resulting mixture is slightly heated until it becomes a solution. The solution is cooled to room temperature, 3.2 mL of diethyl phosphate is added thereto, stirring at room temperature for 30 min, and then stirring at 90-100° C. for 3 h, the reaction is completed. The solvent is removed under reduced pressure, and the residue is purified by column chromatography (eluent: 1-4% MeOH in DCM) to obtain 7.6 g target compound (yield: 63%). The analytical data of the obtained product are as follows: $^1$HNMR (400 MHz, DMSO-$d_6$): δ=7.30-7.21 (m, 5H), 4.01-3.93 (m, 4H), 3.69 (s, 2H), 3.59 (t, J=6.8 Hz, 2H), 2.83 (d, J=10.0 Hz, 2H), 2.61 (t, J=6.8 Hz, 2H), 1.85-1.82 (m, 2H), 1.2 (t, J=7.2 Hz, 6H).

Preparation Method of Intermediate F: 4-[[7-[3-(benzyl(diethoxyphosphorylmethyl)amino)propoxyl]-6-methoxyl-4-quinolyl]oxyl]-3-fluorophenylamine

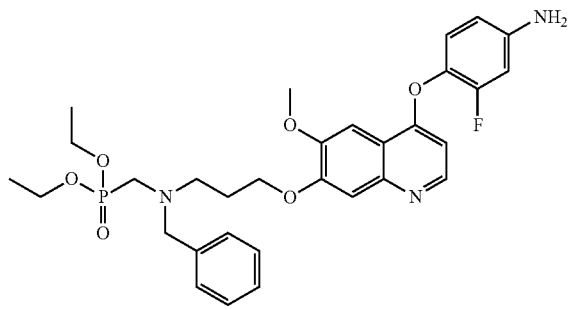 [SMILES: CCOP(=O)(CN(CCCOc1cc2nccc(Oc3ccc(N)cc3F)c2cc1OC)Cc1ccccc1)OCC]

Step 1: preparation of N-benzyl-N-(diethoxyphosphorylmethyl)-3-[[4-(2-fluoro-4-nitrophenoxy)-6-methoxyl-7-quinolyl]oxyl]propan-1-amine: potassium carbonate (7.3 g or 53.2 mmol) is added to DMF solution (100 mL) of intermediate E (7.6 g or 22.8 mmol) and intermediate A (5.0 g or 15.2 mmol). The resulting mixture is stirred at 110° C. for 2 h. The reaction mixture is diluted with 500 ml of ethyl acetate, inorganic salt is removed by filtering, the filtrate is concentrated, and the residue is purified by column chromatography (eluent: 1-4% MeOH in DCM) to obtain 3.6 g target compound (yield: 38%). The analytical data of the obtained product are as follows: $^1$HNMR (400 MHz, DMSO-$d_6$): δ=8.57 (d, J=5.2 Hz, 1H), 8.47 (dd, J=2.4, 10.4 Hz, 1H), 8.21-8.18 (m, 1H), 7.63 (t, J=8.8 Hz, 1H), 7.41-7.18 (m, 8H), 6.78 (d, J=5.2 Hz, 1H), 4.17 (t, J=6.4 Hz, 2H), 4.04-3.96 (m, 4H), 3.86 (s, 3H), 3.78 (s, 2H), 2.91 (d, J=10.0 Hz, 2H), 2.73 (t, J=6.4 Hz, 2H), 2.00 (t, J=6.4 Hz, 2H), 1.24-1.19 (m, 6H).

Step 2: preparation of 4-[[7-[3-(benzyl(diethoxyphosphorylmethyl)amino) propoxyl]-6-methoxyl-4-quinolyl]oxyl]-3-fluorophenylamine: N-benzyl-N-(diethoxyphosphorylmethyl)-3-[[4-(2-fluoro-4-nitrophenoxy)-6-methoxyl-7-quinolyl]oxyl]propan-1-amine (3.6 g or 28.7 mmol) obtained from Step 1 is dissolved in 300 ml of THF, 5 g of Raney nickel is added thereto, the resulting mixture is stirred at 30° C. under 30 psi of hydrogen pressure for 2 h. Finally the reaction mixture is filtered, and the filtrate is concentrated under reduced pressure to obtain 2.9 g of target compound (yield: 83%). The analytical data of the obtained product are as follows: mass spectrum m/z: 598.01 [M+H].

Preparation Method of Intermediate G: 4-[[6-[3-(benzyl(diethoxyphosphorylmethyl)amino)propoxyl]-7-methoxyl-4-quinolyl]oxyl]-3-fluorophenylamine

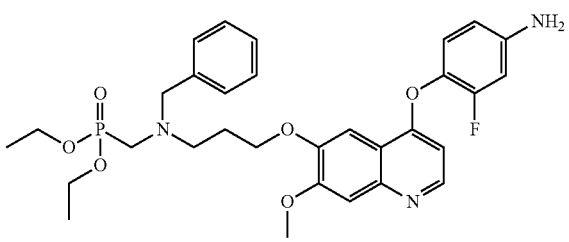 [SMILES: CCOP(=O)(CN(CCCOc1cc2c(Oc3ccc(N)cc3F)ccnc2cc1OC)Cc1ccccc1)OCC]

Starting from intermediate E and intermediate B, intermediate G is prepared in the same manner as the method of preparing intermediate F. The analytical data of the obtained product are as follows: mass spectrum m/z: 598.08 [M+H].

Preparation Method of Intermediate H: 3-chloro-N-(diethoxyphosphorylmethyl)-N-methylpropan-1-amine

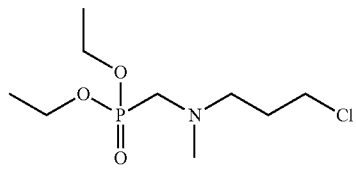

0.8 mL of 37% aqueous formaldehyde solution is added to suspension of 3-chloro-N-methylpropan-1-amine (1.4 g or 1.3 mmol) in dioxane (30 mL), the resulting mixture is slightly heated until it becomes a solution. The solution is cooled to room temperature, 1.6 mL of diethyl phosphate is added thereto, stirring at room temperature for 30 min, and then stirring at 90-100° C. for 3 h, the reaction is completed. The solvent is removed under reduced pressure, and the residue is purified by column chromatography (eluent: 1-4% MeOH in DCM) to obtain 2.3 g target compound (yield: 81%). The analytical data of the obtained product are as follows: $^1$HNMR (400 MHz, CDCl$_3$): δ=4.17-4.10 (m, 4H), 3.74-3.53 (m, 4H), 3.28-3.08 (m, 2H), 2.80 (s, 3H), 2.25-2.09 (m, 2H), 1.29 (t, J=6.8 Hz, 6H).

Preparation Method of Intermediate I: 4-[[7-[3-(di-ethoxyphosphorylmethyl(methyl))amino)propoxyl]-6-methoxyl-4-quinolyl]oxyl]-3-fluorophenylamine

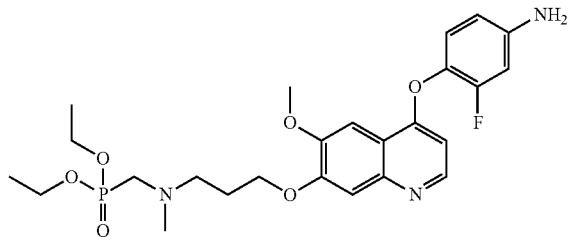 [SMILES: CCOP(=O)(CN(C)CCCOc1cc2nccc(Oc3ccc(N)cc3F)c2cc1OC)OCC]

Step 1: preparation of N-(diethoxyphosphorylmethyl)-3-[[4-(2-fluoro-4-nitrophenoxy)-6-methoxyl-7-quinolyl]oxyl]-N-methyl-propan-1-amine: potassium carbonate (2.9 g or 21.0 mmol) is added to DMF solution (45 mL) of intermediate H (2.0 g or 6.0 mmol) and intermediate A (2.3 g or 9.0 mmol). The resulting mixture is stirred at 110° C. for 2 h. The reaction mixture is diluted with 100 ml of ethyl acetate, inorganic salt is removed by filtering, the filtrate is concentrated, and the residue is purified by column chromatography (eluent: 1-5% MeOH in DCM) to obtain 1.8 g target compound (yield: 55%). The analytical data of the obtained product are as follows: $^1$HNMR (400 MHz, DMSO-$d_6$): δ=8.55 (d, J=5.2 Hz, 1H), 8.46 (dd, J=2.4, 10.8 Hz, 1H), 8.22-8.15 (m, 1H), 7.62 (t, J=8.4 Hz, 1H), 7.43 (d, J=12.8 Hz, 2H), 6.76 (d, J=5.2 Hz, 1H), 4.20 (t, J=8.4 Hz, 2H), 4.01-3.95 (m, 4H), 3.91 (s, 3H), 2.82 (d, J=10.8 Hz, 2H), 2.64 (t, J=6.8 Hz, 2H), 2.34 (s, 3H), 1.96-1.93 (m, 3H), 1.21 (t, J=4.4 Hz, 6H).

Step 2: preparation of 4-[[7-[3-(diethoxyphosphorylmethyl(methyl))amino)propoxyl]-6-methoxyl-4-quinolyl]oxyl]-3-fluorophenylamine: N-(diethoxyphosphorylmethyl)-3-[[4-(2-fluoro-4-nitrophenoxy)-6-methoxyl-7-quinolyl]oxyl]-N-methyl-propan-1-amine (1.8 g or 3.3 mmol) obtained from Step 1 is dissolved in 170 ml of THF, 5 g of Raney nickel is added thereto, the resulting mixture is stirred at 30° C. under 30 psi of hydrogen pressure for 2 h. Finally the reaction mixture is filtered, and the filtrate is concentrated under reduced pressure to obtain 1.6 g of target compound (yield: 97%). The analytical data of the obtained product are as follows: mass spectrum m/z: 522.10 [M+H].

Preparation Method of Intermediate J: 4-[[6-[3-(di-ethoxyphosphorylmethyl)(methyl)amino)propoxyl]-7-methoxyl-4-quinolyl]oxyl]-3-fluorophenylamine

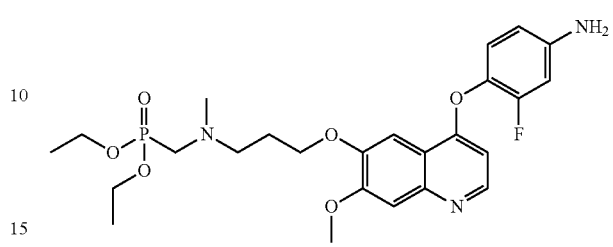

Starting from intermediate H and intermediate B, intermediate J is prepared in the same manner as the method of preparing intermediate I. The analytical data of the obtained product are as follows: mass spectrum m/z: 522.12 [M+H].

Preparation Method of Intermediate K: N1-[3-fluoro-4-[[6-methoxyl-7-(4-piperidinylmethoxyl)-4-quinolyl]oxyl]phenyl]-N1'-(4-fluorophenyl)cyclopropane-1,1-dicarboxamide dihydrochloride

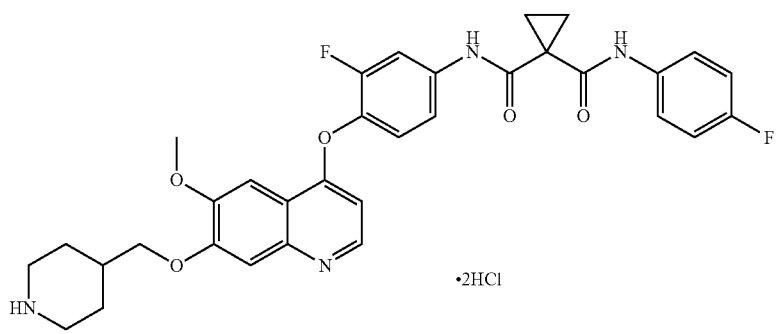 [SMILES: COc1cc2c(Oc3ccc(NC(=O)C4(C(=O)Nc5ccc(F)cc5)CC4)cc3F)ccnc2cc1OCC1CCNCC1]

Step 1: preparation of tert-butyl 4-[[4-[2-fluoro-4-[[1-[(4-fluorophenyl)aminocarbonyl]cyclopropane carbonyl]amino]phenoxy]-6-methoxyl-7-quinolyl]oxymethyl]piperidine-1-carboxylate: a mixture of intermediate C (1.5 g or 3.0 mmol), intermediate D (1.7 g or 7.6 mmol), DIPEA (1.55 g or 12.0 mmol), HATU (2.3 g or 6.0 mmol), DMAP (0.183 g or 1.5 mmol) in DMF (60 mL) is stirred at 30-40° C. overnight. The mixture is concentrated under reduced pressure, and the residue is purified by column chromatography (eluent: 1-5% MeOH in DCM) to obtain 1.9 g target compound (yield: 90%). The analytical data of the obtained product are as follows: mass spectrum m/z: 703.30 [M+H].

Step 2: preparation of tert-butyl N1-[3-fluoro-4-[[6-methoxyl-7-(4-piperidinylmethoxyl)-4-quinolyl]oxyl]phenyl]-N1'-(4-fluorophenyl)cyclopropane-1,1-dicarboxamide dihydrochloride: at 0° C., saturated EtOAc solution (40 mL) of HCl is added to a solution of tert-butyl 4-[[4-[2-fluoro-4-[[1-[(4-fluorophenyl)amino carbonyl]cyclopropanecarbonyl]amino]phenoxy]-6-methoxyl-7-quinolyl]oxymethyl]piperidine-1-carboxylate (1.6 g or 2.3 mmol) obtained from Step 1 in EtOAc (40 mL), the resulting mixture is stirred at room temperature for 4 h. The mixture is filtered to collect the precipitate followed by washing with EtOAc to give 1.0 g of target compound (yield: 69%). The analytical data of the obtained product are as follows: mass spectrum m/z: 603.10 [M+H].

EXAMPLE 1

Preparation of one of the phosphorus-containing group-substituted quinolines according to the present invention, N1-[4-[[7-[3-(benzyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide:

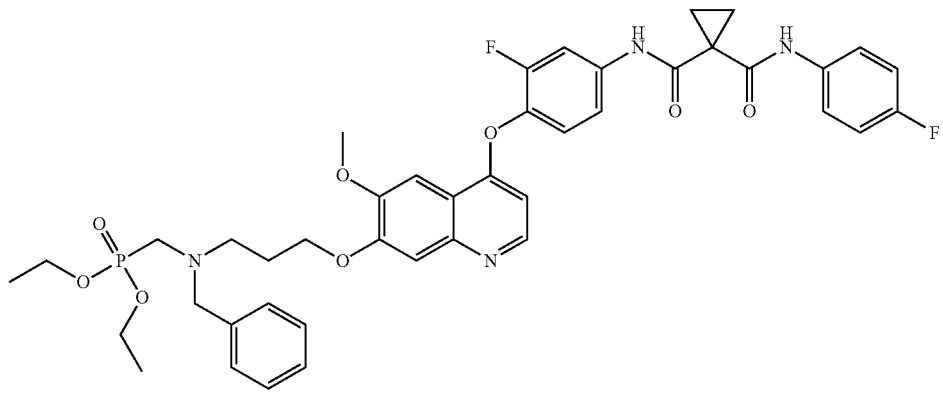 [SMILES: CCOP(=O)(CN(CCCOc1cc2nccc(Oc3ccc(NC(=O)C4(C(=O)Nc5ccc(F)cc5)CC4)cc3F)c2cc1OC)Cc1ccccc1)OCC]

A mixture of intermediate F (3.3 g or 5.5 mmol), intermediate D (3.1 g or 13.8 mmol), DIPEA (3.8 g or 22.1 mmol), HATU (4.2 g or 11.0 mmol), DMAP (0.337 g or 2.8 mmol) dissolved in DMF (150 mL) is stirred at 30-40° C. overnight. The mixture is concentrated under reduced pressure, and the residue is purified by column chromatography (eluent: 1-4% MeOH in DCM) to obtain 3.0 g of the compound according to the invention (yield: 68%). The analytical data of the obtained product are as follows: mass spectrum m/z: 803.10 [M+H].

EXAMPLE 2

Preparation of one of the phosphorus-containing group-substituted quinolines according to the present invention, N1-[4-[[6-[3-(benzyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide:

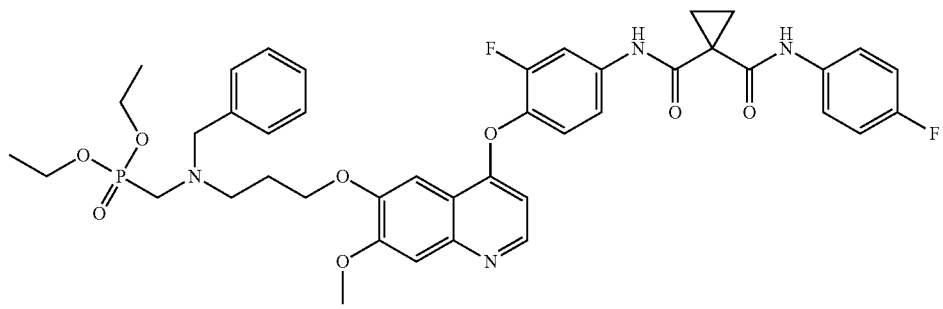 [SMILES: CCOP(=O)(CN(CCCOc1cc2c(Oc3ccc(NC(=O)C4(C(=O)Nc5ccc(F)cc5)CC4)cc3F)ccnc2cc1OC)Cc1ccccc1)OCC]

Using intermediate G and intermediate D, the above compound is prepared in the same manner as Example 1. The analytical data of the obtained product are as follows: mass spectrum m/z: 803.13 [M+H].

EXAMPLE 3

Preparation of one of the phosphorus-containing group-substituted quinolines according to the present invention, N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide:

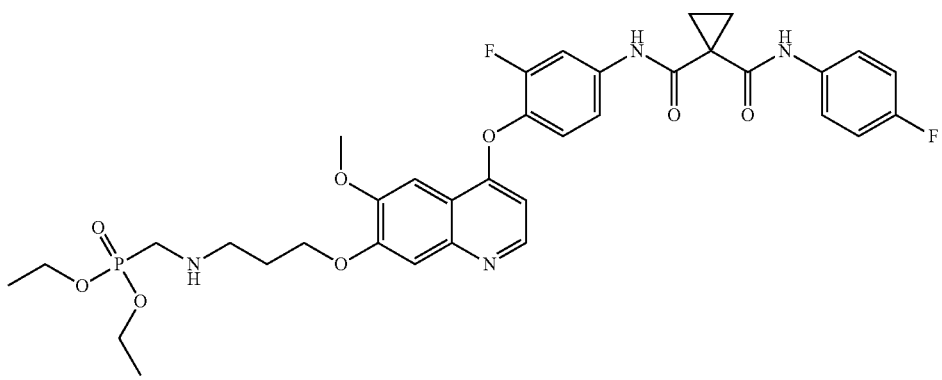 [SMILES: CCOP(=O)(CNCCCOc1cc2nccc(Oc3ccc(NC(=O)C4(C(=O)Nc5ccc(F)cc5)CC4)cc3F)c2cc1OC)OCC]

N1-[4-[[7-[3-(benzyl(diethoxyphosphorylmethyl)amino) propoxyl]-6-methoxyl-4-quinolyl]oxyl]-3-fluorophenyl]-N1'-(4-fluorophenyl)cyclopropane-1,1-dicarboxamide obtained from Example 1 (1.0 g or 1.2 mmol) is dissolved in EtOH/THF (1:1, 250 mL), Pd(OH)$_2$ (1 g) is added thereto, and the resulting mixture is stirred at 45° C. under 50 psi of hydrogen pressure for 18 h. Finally, the reaction mixture is filtered, the filtrate is concentrated under reduced pressure, and the residue is purified by column chromatography (eluent: 1-4% MeOH in DCM) to give 0.368 g of the compound according to the invention (yield: 43%). The analytical data of the obtained product are as follows: mass spectrum m/z: 713.20 [M+H].

EXAMPLE 4

Preparation of one of the phosphorus-containing group-substituted quinolines according to the present invention, N1-[4-[[6-[3-(diethoxyphosphorylmethylamino)propoxyl]-7-methoxyl-4-quinolyl]oxyl]-3-fluorophenyl]-N1'-(4-fluorophenyl)cyclopropane-1,1-dicarboxamide:

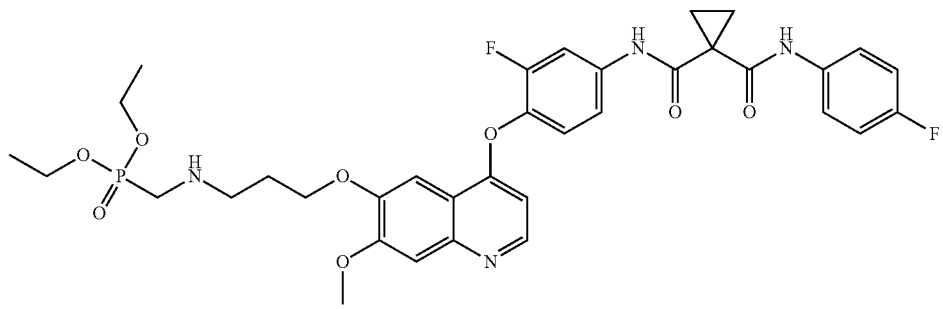 [SMILES: CCOP(=O)(CNCCCOc1cc2c(Oc3ccc(NC(=O)C4(C(=O)Nc5ccc(F)cc5)CC4)cc3F)ccnc2cc1OC)OCC]

Using N1-[4-[[6-[3-(benzyl(diethoxyphosphorylmethyl) amino)propoxyl]-7-methoxyl-4-quinolyl]oxyl]-3-fluorophenyl]-N1'-(4-fluorophenyl)cyclopropane-1,1-dicarboxamide obtained from Example 2, the above compound is prepared in the same manner as Example 3. The analytical data of the obtained product are as follows: mass spectrum m/z: 713.21 [M+H].

EXAMPLE 5

Preparation of one of the phosphorus-containing group-substituted quinolines according to the present invention, N1-[4-[[7-[3-(acetyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide:

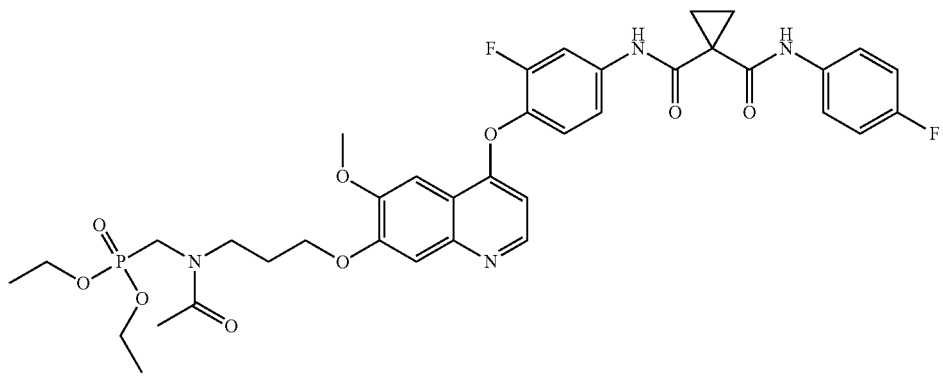 [SMILES: CCOP(=O)(CN(CCCOc1cc2nccc(Oc3ccc(NC(=O)C4(C(=O)Nc5ccc(F)cc5)CC4)cc3F)c2cc1OC)C(C)=O)OCC]

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide obtained from Example 3 (1.0 g or 1.4 mmol) and DIPEA (0.544 g or 4.2 mmol) are dissolved in DCM (50 mL), acetic anhydride (0.428 g or 4.2 mmol) is added thereto, and the resulting mixture is stirred at room temperature for 2 h. The reaction mixture is diluted with DCM, followed by washing with brine, and then concentrating, and the residue is purified by column chromatography (eluent: 1-3% MeOH in DCM) to give 0.856 g of the compound according to the invention (yield: 81%). The analytical data of the obtained product are as follows: mass spectrum m/z: 755.18 [M+H].

EXAMPLE 6

Preparation of one of the phosphorus-containing group-substituted quinolines according to the present invention, N1-[4-[[6-[3-(acetyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide:

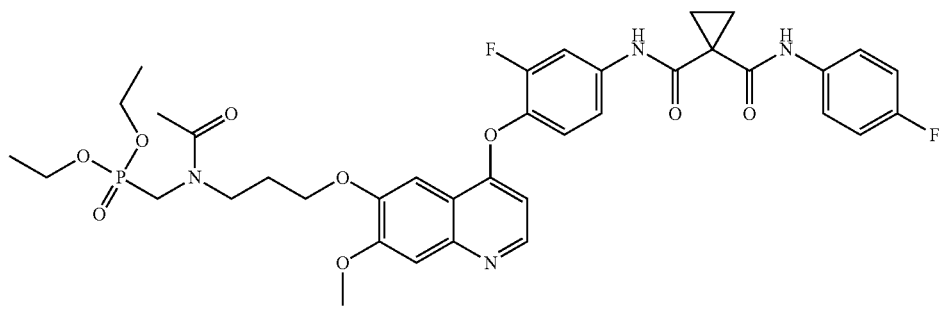 [SMILES: CCOP(=O)(CN(CCCOc1cc2c(Oc3ccc(NC(=O)C4(C(=O)Nc5ccc(F)cc5)CC4)cc3F)ccnc2cc1OC)C(C)=O)OCC]

Using N1-[4-[[6-[3-(diethoxyphosphorylmethylamino) propoxyl]-7-methoxyl-4-quinolyl]oxyl]-3-fluorophenyl]-N1'-(4-fluorophenyl)cyclopropane-1,1-dicarboxamide obtained from Example 4, the above compound is synthesized in the same manner as Example 5. The analytical data of the obtained product are as follows: mass spectrum m/z: 755.18 [M+H].

EXAMPLE 7

Preparation of one of the phosphorus-containing group-substituted quinolines according to the present invention, N1-[4-[[7-[3-(diethoxyphosphorylmethyl)(methyl)amino)propoxyl]-6-methoxyl-4-quinolyl]oxyl]-3-fluorophenyl]-N1'-(4-fluorophenyl)cyclopropane-1,1-dicarboxamide:

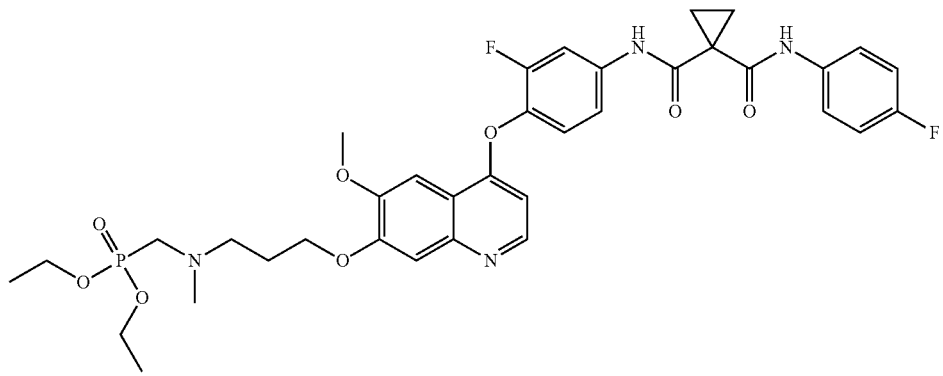 [SMILES: CCOP(=O)(CN(C)CCCOc1cc2nccc(Oc3ccc(NC(=O)C4(C(=O)Nc5ccc(F)cc5)CC4)cc3F)c2cc1OC)OCC]

A mixture of intermediate I (0.8 g or 1.5 mmol), intermediate D (0.856 g or 7.6 mmol), DIPEA (1.1 mL or 6.1 mmol), HATU (1.2 g or 3.1 mmol), DMAP (0.093 g or 0.8 mmol) in DMF (60 mL) is stirred at 30-40° C. overnight. The mixture is concentrated under reduced pressure, and the residue is purified by column chromatography (eluent: 1-5% MeOH in DCM) to give 0.352 g of the compound according to the invention (yield: 31%). The analytical data of the obtained product are as follows: $^1$HNMR (400 MHz, DMSO-d$_6$): δ=10.37 (s, 1H), 9.99 (s, 1H), 8.46 (d, J=5.2 Hz, 1H), 7.90 (dd, J=2.4, 13.2 Hz, 1H), 7.64-7.60 (m, 2H), 7.64-7.60 (m, 2H), 7.51-7.49 (m, 2H), 7.16-7.11 (m, 2H), 6.41 (t, J=4.4 Hz, 1H), 4.19 (t, J=6.0 Hz, 1H), 4.04-3.96 (m, 4H), 3.93 (s, 3H), 2.90-2.81 (m, 2H), 2.71-2.61 (m, 2H), 2.06 (s, 3H), 1.98-1.90 (m, 2H), 1.46-1.42 (m, 4H), 1.21 (t, J=7.2 Hz, 6H).

EXAMPLE 8

Preparation of one of the phosphorus-containing group-substituted quinolines according to the present invention, N1-[4-[[6-[3-(diethoxyphosphorylmethyl)(methyl)amino)propoxyl]-7-methoxyl-4-quinolyl]oxyl]-3-fluorophenyl]-N1'-(4-fluorophenyl)cyclopropane-1,1-dicarboxamide:

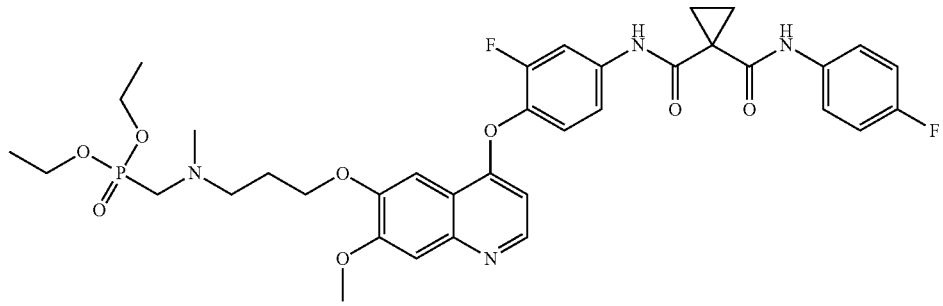 [SMILES: CCOP(=O)(CN(C)CCCOc1cc2c(Oc3ccc(NC(=O)C4(C(=O)Nc5ccc(F)cc5)CC4)cc3F)ccnc2cc1OC)OCC]

Using intermediate J and intermediate D, the above compound is prepared in the same manner as Example 7. The analytical data of the obtained product are as follows: mass spectrum m/z: 727.20 [M+H].

EXAMPLE 9

Preparation of one of the phosphorus-containing group-substituted quinolines according to the present invention, N1-[4-[[7-[[1-(2-diethoxyphosphorylacetyl)-4-piperidinyl]methoxyl]-6-methoxyl-4-quinolyl]oxyl]-3-fluorophenyl]-N1'-(4-fluorophenyl)cyclopropane-1,1-dicarboxamide:

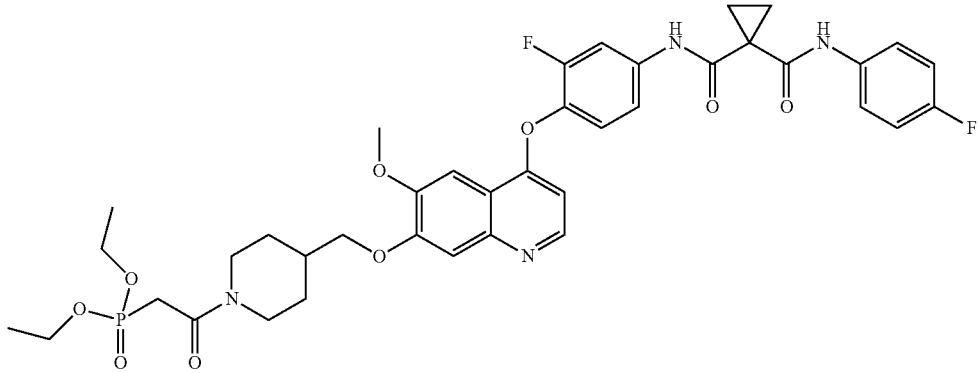 [SMILES: CCOP(=O)(CC(=O)N1CCC(COc2cc3nccc(Oc4ccc(NC(=O)C5(C(=O)Nc6ccc(F)cc6)CC5)cc4F)c3cc2OC)CC1)OCC]

A mixture of intermediate K (0.5 g or 0.8 mmol), 2-diethoxyphosphoryl acetic acid (0.307 g or 1.6 mmol), DIPEA (0.404 g or 3.1 mmol), HATU (0.597 g or 1.6 mmol) in DMF (15 mL) is stirred at room temperature for 2 h. The mixture is concentrated under reduced pressure, and the residue is purified by column chromatography (eluent: 1-5% MeOH in DCM) to give 0.237 g the compound according to the invention (yield: 39%). The analytical data of the obtained product are as follows: $^1$HNMR (400 MHz, DMSO-$d_6$): δ=10.37 (s, 1H), 9.99 (s, 1H), 8.45 (d, J=5.2 Hz, 1H), 7.90 (dd, J=2.0, 13.2 Hz, 1H), 7.64-7.60 (m, 2H), 7.50-7.48 (m, 2H), 7.42-7.37 (m, 2H), 7.16-7.11 (m, 2H), 6.40 (dd, J=1.2, 5.2 Hz, 1H), 4.45-4.35 (m, 1H), 4.05-3.98 (m, 7H), 3.93 (s, 3H), 3.20-3.00 (m, 3H), 2.65-2.55 (m, 1H), 2.20-2.00 (m, 1H), 1.88-1.78 (m, 2H), 1.45-1.44 (m, 4H), 1.42-1.28 (m, 1H), 1.23 (t, J=6.8 Hz, 6H), 1.18-1.08 (m, 1H).

EXAMPLE 10

Preparation of one of the phosphorus-containing group-substituted quinolines according to the present invention, N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide:

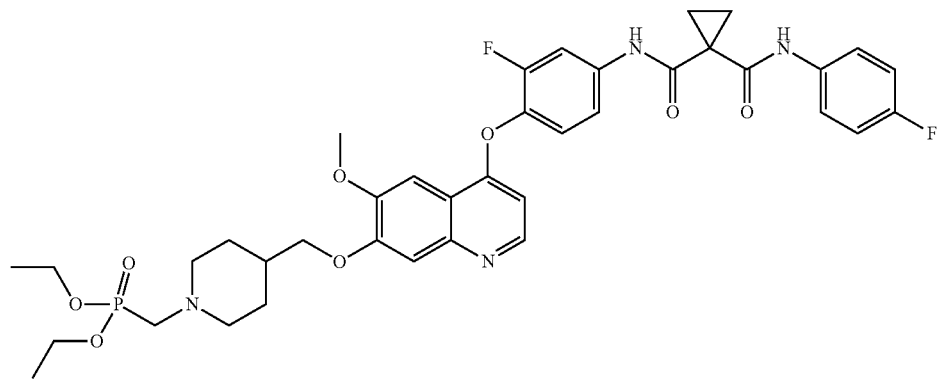 [SMILES: CCOP(=O)(CN1CCC(COc2cc3nccc(Oc4ccc(NC(=O)C5(C(=O)Nc6ccc(F)cc6)CC5)cc4F)c3cc2OC)CC1)OCC]

0.11 mL of 37% aqueous formaldehyde solution is added to the suspension of intermediate K (0.8 g or 1.3 mmol) in dioxane (10 mL), the resulting mixture is slightly heated until it becomes a solution. The solution is cooled to room temperature, 0.21 mL of diethyl phosphate is added thereto with stirring at room temperature for 30 min, and then stirring at 90-100° C. for 3 h, and the reaction is completed. The solvent is removed under reduced pressure, and the residue is purified by column chromatography (eluent: 1-4% MeOH in DCM) to give 0.354 g of the compound according to the invention (yield: 35%). The analytical data of the obtained product are as follows: $^1$HNMR (400 MHz, DMSO-$d_6$): δ=10.37 (s, 1H), 10.00 (s, 1H), 8.45 (d, J=5.2 Hz, 1H), 7.90 (dd, J=2.0, 13.2 Hz, 1H), 7.64-7.60 (m, 2H), 7.51-7.49 (m, 2H), 7.42-7.36 (m, 2H), 7.16-7.11 (m, 2H), 6.39 (d, J=5.2 Hz, 1H), 4.05-3.97 (m, 6H), 3.93 (s, 3H), 3.06-3.03 (m, 2H), 2.76-2.74 (m, 2H), 2.15-2.09 (m, 2H), 1.88-1.74 (m, 3H), 1.45-1.33 (m, 6H), 1.24 (t, J=6.8 Hz, 6H).

EXAMPLE 11

Preparation of one of the phosphorus-containing group-substituted quinolines according to the present invention, N1'-[4-[[7-[3-(amino carbonyl(diethoxyphosphorylmethyl)amino)propoxyl]-6-methoxyl-4-quinolyl]oxyl]-3-fluorophenyl]-N1-(4-fluorophenyl)cyclopropane-1,1-dicarboxamide:

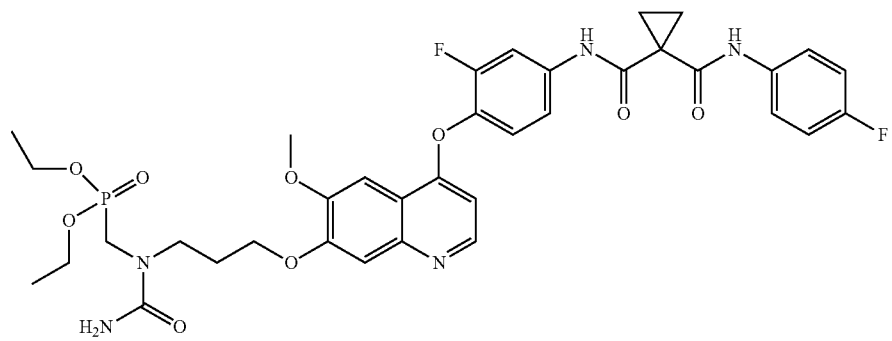 [SMILES: CCOP(=O)(CN(CCCOc1cc2nccc(Oc3ccc(NC(=O)C4(C(=O)Nc5ccc(F)cc5)CC4)cc3F)c2cc1OC)C(N)=O)OCC]

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide obtained from Example 3 (71.2 mg or 0.1 mmol) is dissolved in DCM (5 mL), then Me$_3$Si—NCO (23.0 mg or 0.20 mmol) and diisopropylethylamine (38.5 mg or 0.3 mmol) are added thereto, the resulting mixture is stirred at room temperature for 16 h, the solvent is removed under reduced pressure, and the crude product is purified by silica gel column chromatography (eluent: 1-4% MeOH in DCM) to give 57.5 mg of the compound according to the invention (yield: 76%). The analytical data of the obtained product are as follows: mass spectrum m/z: 756.12 [M+H].

EXAMPLE 12

Preparation of one of the phosphorus-containing group-substituted quinolines according to the present invention, N1'-[4-[[6-[3-(amino carbonyl(diethoxyphosphorylmethyl)amino)propoxyl]-7-methoxyl-4-quinolyl]oxyl]-3-fluorophenyl]-N1-(4-fluorophenyl)cyclopropane-1,1-dicarboxamide:

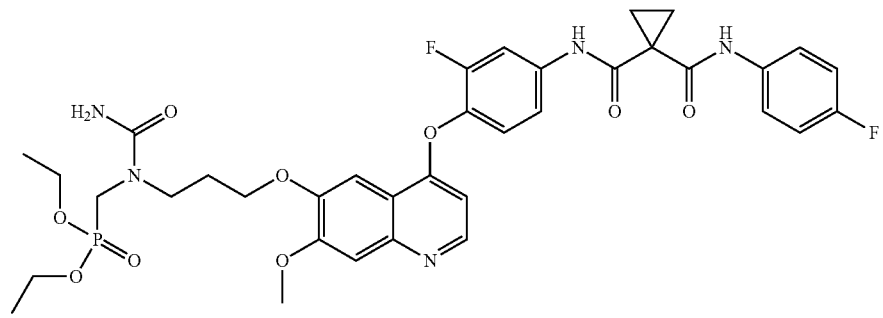 [SMILES: CCOP(=O)(CN(CCCOc1cc2c(Oc3ccc(NC(=O)C4(C(=O)Nc5ccc(F)cc5)CC4)cc3F)ccnc2cc1OC)C(N)=O)OCC]

Using N1-[4-[[6-[3-(diethoxyphosphorylmethylamino) propoxyl]-7-methoxyl-4-quinolyl]oxyl]-3-fluorophenyl]-N1'-(4-fluorophenyl)cyclopropane-1,1-dicarboxamide obtained from Example 4, the above compound is prepared in the same manner as Example 11. The analytical data of the obtained product are as follows: mass spectrum m/z: 756.18 [M+H].

EXAMPLE 13

Preparation of one of the phosphorus-containing group-substituted quinolines according to the present invention, N1'-[4-[[7-[3-(diethoxyphosphorylmethyl)(ethylaminocarbonyl)amino)propoxyl]-6-methoxyl-4-quinolyl]oxyl]-3-fluorophenyl]-N1-(4-fluorophenyl)cyclopropane-1,1-dicarboxamide:

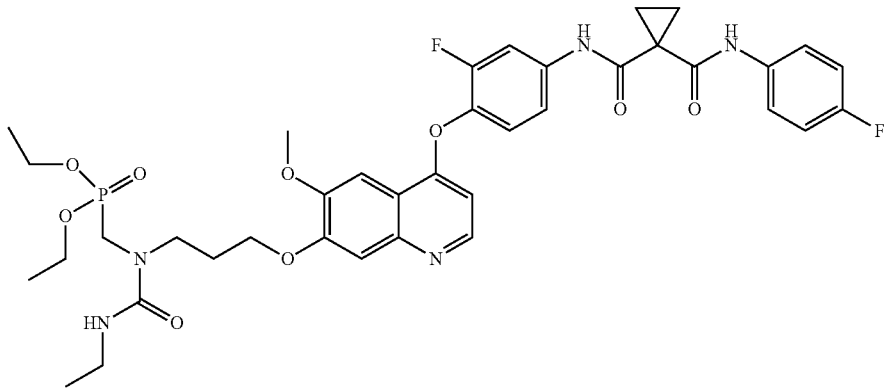 [SMILES: CCNC(=O)N(CCCOc1cc2nccc(Oc3ccc(NC(=O)C4(C(=O)Nc5ccc(F)cc5)CC4)cc3F)c2cc1OC)CP(=O)(OCC)OCC]

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide obtained from Example 3 (71.2 mg or 0.1 mmol) is dissolved in DCM (5 mL), then EtNCO (14.2 mg or 0.20 mmol) and diisopropylethylamine (38.5 mg or 0.3 mmol) are added thereto, the resulting mixture is stirred at room temperature for 16 h, the solvent is removed under reduced pressure, and the crude product is purified by silica gel column chromatography (eluent: 1-4% MeOH in DCM) to give 64.3 mg the compound according to the invention (yield: 82%). The analytical data of the obtained product are as follows: mass spectrum m/z: 784.22 [M+H].

EXAMPLE 14

Preparation of one of the phosphorus-containing group-substituted quinolines according to the present invention, N1'-[4-[[7-[3-(diethoxyphosphorylmethyl)(propionyl)amino)propoxyl]-6-methoxyl-4-quinolyl]oxyl]-3-fluorophenyl]-N1-(4-fluorophenyl)cyclopropane-1,1-dicarboxamide:

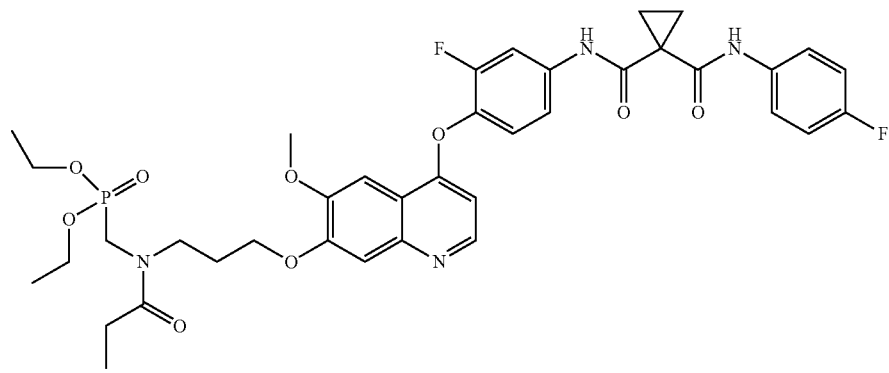 [SMILES: CCOP(=O)(CN(CCCOc1cc2nccc(Oc3ccc(NC(=O)C4(C(=O)Nc5ccc(F)cc5)CC4)cc3F)c2cc1OC)C(=O)CC)OCC]

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide (71.2 mg or 0.1 mmol) obtained from Example 3 is dissolved in DCM (5 mL), then propionic acid (14.8 mg or 0.20 mmol), EDC.HCl (38.4 mg or 0.2 mmol) and diisopropylethylamine (64.2 mg or 0.5 mmol) are added thererto, the resulting mixture is stirred at room temperature for 16 h, the solvent is removed under reduced pressure, and the crude product is purified by silica gel column chromatography (eluent: 1-4% MeOH in DCM) to give 50.7 mg the compound according to the invention (yield: 66%). The analytical data of the obtained product are as follows: mass spectrum m/z: 769.15 [M+H].

EXAMPLE 15

Preparation of one of the phosphorus-containing group-substituted quinolines according to the present invention, N1'-[4-[[7-[3-(diethoxyphosphorylmethyl)(methylsulfonyl)amino)propoxyl]-6-methoxyl-4-quinolyl]oxyl]-3-fluorophenyl]-N1-(4-fluorophenyl)cyclopropane-1,1-dicarboxamide:

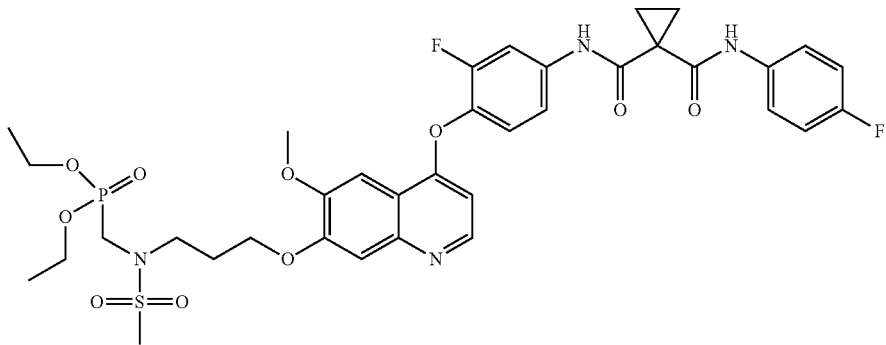 [SMILES: CCOP(=O)(CN(CCCOc1cc2nccc(Oc3ccc(NC(=O)C4(C(=O)Nc5ccc(F)cc5)CC4)cc3F)c2cc1OC)S(C)(=O)=O)OCC]

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide obtained from Example 3 (71.2 mg or 0.1 mmol) is dissolved in DCM (5 mL), and then methylsulfonyl chloride (22.9 mg or 0.20 mmol), EDC.HCl (38.4 mg or 0.2 mmol) and diisopropylethylamine (64.2 mg or 0.5 mmol) are added thererto, the resulting mixture is stirred at room temperature for 16 h, the solvent is removed under reduced pressure, and the crude product is purified by silica gel column chromatography (eluent: 1-4% MeOH in DCM) to give 44.3 mg the compound according to the invention (yield: 56%). The analytical data of the obtained product are as follows: mass spectrum m/z: 791.28 [M+H].

EXAMPLE 16

The Screening Test for Inhibiting the Kinase

In this example, the compound prepared in Example 10, N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide is tested for the inhibitory effect in the 442-kinase panel of KinomeScan™ (www.kinomescan.com) from DiscoveRx Corporation (4215 Sorrento Valley Blvd, San Diego, Calif. 92121) at 1000 nM of the compound concentration, the results are shown in the following Table 5:

For the detailed information of the screening technique, see Fabian, M. A. et al, *Nat., Biotechnol.* 2005, 23, 329 and Karaman, M. W. et al, *Nat., Biotechnol.* 2008, 26, 127. It can be seen from the following representative results that, the compound according to the present invention has significant inhibitory effect on kinases including c-Met, KDR or VEGFR2, RET, PDGFR-β, c-KIT, Flt3, MEK5, DDR1, LOK, CSF1R, EPHA7, EPHA8, EPHB6, MKNK2, BLK, HIPK4, HCK, Flt4 and the mutants thereof

TABLE 5

| Kinase Target<br>Ambit Gene Symbol | Example 10<br>% Ctrl@1000 nM |
| --- | --- |
| AAK1 | 91 |
| ABL1(E255K)-phosphorylated | 63 |
| ABL1(F317I)-nonphosphorylated | 42 |
| ABL1(F317I)-phosphorylated | 70 |
| ABL1(F317L)-nonphosphorylated | 10 |
| ABL1(F317L)-phosphorylated | 69 |
| ABL1(H396P)-nonphosphorylated | 1.9 |

TABLE 5-continued

| Kinase Target<br>Ambit Gene Symbol | Example 10<br>% Ctrl@1000 nM |
| --- | --- |
| ABL1(H396P)-phosphorylated | 63 |
| ABL1(M351T)-phosphorylated | 42 |
| ABL1(Q252H)-nonphosphorylated | 2.4 |
| ABL1(Q252H)-phosphorylated | 84 |
| ABL1(T315I)-nonphosphorylated | 3.8 |
| ABL1(T315I)-phosphorylated | 75 |
| ABL1(Y253F)-phosphorylated | 32 |
| ABL1-nonphosphorylated | 1.8 |
| ABL1-phosphorylated | 33 |
| ABL2 | 28 |
| ACVR1 | 100 |
| ACVR1B | 100 |
| ACVR2A | 100 |
| ACVR2B | 100 |
| ACVRL1 | 100 |
| ADCK3 | 67 |
| ADCK4 | 100 |
| AKT1 | 100 |
| AKT2 | 100 |
| AKT3 | 100 |
| ALK | 15 |
| AMPK-alpha1 | 100 |
| AMPK-alpha2 | 100 |
| ANKK1 | 100 |

TABLE 5-continued

| Kinase Target Ambit Gene Symbol | Example 10 % Ctrl@1000 nM |
|---|---|
| ARK5 | 100 |
| ASK1 | 100 |
| ASK2 | 100 |
| AURKA | 100 |
| AURKB | 74 |
| AURKC | 66 |
| AXL | 8 |
| BIKE | 100 |
| BLK | 0.5 |
| BMPR1A | 100 |
| BMPR1B | 100 |
| BMPR2 | 100 |
| BMX | 92 |
| BRAF | 100 |
| BRAF(V600E) | 100 |
| BRK | 3.0 |
| BRSK1 | 100 |
| BRSK2 | 100 |
| BTK | 51 |
| CAMK1 | 78 |
| CAMK1D | 96 |
| CAMK1G | 88 |
| CAMK2A | 100 |
| CAMK2B | 100 |
| CAMK2D | 94 |
| CAMK2G | 100 |
| CAMK4 | 100 |
| CAMKK1 | 32 |
| CAMKK2 | 81 |
| CASK | 100 |
| CDC2L1 | 100 |
| CDC2L2 | 100 |
| CDC2L5 | 100 |
| CDK11 | 67 |
| CDK2 | 100 |
| CDK3 | 100 |
| CDK4-cyclinD1 | 100 |
| CDK4-cyclinD3 | 100 |
| CDK5 | 100 |
| CDK7 | 15 |
| CDK8 | 76 |
| CDK9 | 100 |
| CDKL1 | 100 |
| CDKL2 | 100 |
| CDKL3 | 100 |
| CDKL5 | 100 |
| CHEK1 | 100 |
| CHEK2 | 35 |
| CIT | 100 |
| CLK1 | 89 |
| CLK2 | 78 |
| CLK3 | 100 |
| CLK4 | 46 |
| CSF1R | 0.25 |
| CSK | 14 |
| CSNK1A1 | 100 |
| CSNK1A1L | 100 |
| CSNK1D | 100 |
| CSNK1E | 100 |
| CSNK1G1 | 100 |
| CSNK1G2 | 100 |
| CSNK1G3 | 100 |
| CSNK2A1 | 100 |
| CSNK2A2 | 100 |
| CTK | 100 |
| DAPK1 | 100 |
| DAPK2 | 100 |
| DAPK3 | 100 |
| DCAMKL1 | 91 |
| DCAMKL2 | 100 |
| DCAMKL3 | 100 |
| DDR1 | 0 |
| DDR2 | 7.8 |
| DLK | 52 |
| DMPK | 85 |
| DMPK2 | 76 |
| DRAK1 | 100 |
| DRAK2 | 100 |
| DYRK1A | 100 |
| DYRK1B | 86 |
| DYRK2 | 100 |
| EGFR | 100 |
| EGFR(E746-A750del) | 92 |
| EGFR(G719C) | 75 |
| EGFR(G719S) | 81 |
| EGFR(L747-E749del,A750P) | 67 |
| EGFR(L747-S752del,P753S) | 67 |
| EGFR(L747-T751del,Sins) | 72 |
| EGFR(L858R) | 59 |
| EGFR(L858R,T790M) | 100 |
| EGFR(L861Q) | 84 |
| EGFR(S752-1759del) | 82 |
| EGFR(T790M) | 100 |
| EIF2AK1 | 100 |
| EPHA1 | 4.6 |
| EPHA2 | 4.8 |
| EPHA3 | 6 |
| EPHA4 | 4 |
| EPHA5 | 3.5 |
| EPHA6 | 4.8 |
| EPHA7 | 0.8 |
| EPHA8 | 0.15 |
| EPHB1 | 4.6 |
| EPHB2 | 2.8 |
| EPHB3 | 36 |
| EPHB4 | 12 |
| EPHB6 | 0.9 |
| ERBB2 | 96 |
| ERBB3 | 98 |
| ERBB4 | 100 |
| ERK1 | 99 |
| ERK2 | 100 |
| ERK3 | 100 |
| ERK4 | 100 |
| ERK5 | 100 |
| ERK8 | 95 |
| ERN1 | 81 |
| FAK | 51 |
| FER | 50 |
| FES | 44 |
| FGFR1 | 100 |
| FGFR | 76 |
| FGFR3 | 69 |
| FGFR3(G697C) | 100 |
| FGFR4 | 100 |
| FGR | 35 |
| FLT1 | 7.3 |
| FLT3 | 2.3 |
| FLT3(D835H) | 0.6 |
| FLT3(D835Y) | 2.4 |
| FLT3(ITD) | 2.8 |
| FLT3(K663Q) | 0.55 |
| FLT3(N841L) | 0 |
| FLT3(R834Q) | 16 |
| FLT4 | 0.2 |
| FRK | 8.8 |
| FYN | 48 |
| GAK | 100 |
| GCN2(kin.dom.2.S808G) | 100 |
| GRK1 | 100 |
| GRK4 | 78 |
| GRK7 | 100 |
| GSK3A | 100 |
| GSK3B | 100 |
| HCK | 0.35 |
| HIPK1 | 92 |
| HIPK2 | 100 |
| HIPK3 | 66 |
| HIPK4 | 0.15 |
| HPK1 | 40 |
| HUNK | 100 |
| ICK | 95 |
| IGF1R | 94 |
| IKK-alpha | 100 |

TABLE 5-continued

| Kinase Target Ambit Gene Symbol | Example 10 % Ctrl@1000 nM |
|---|---|
| IKK-beta | 100 |
| IKK-epsilon | 94 |
| INSR | 54 |
| INSRR | 65 |
| IRAK1 | 100 |
| IRAK3 | 33 |
| IRAK4 | 100 |
| ITK | 34 |
| JAK1(JH1domain-catalytic) | 93 |
| JAK1(JH2domain-pseudokinase) | 100 |
| JAK2(JH1domain-catalytic) | 100 |
| JAK3(JH1domain-catalytic) | 100 |
| JNK1 | 80 |
| JNK2 | 93 |
| JNK3 | 95 |
| KIT | 0.2 |
| KIT(A829P) | 64 |
| KIT(D816H) | 63 |
| KIT(D816V) | 18 |
| KIT(L576P) | 0 |
| KIT(V559D) | 0.15 |
| KIT(V559D, T670I) | 1.4 |
| KIT(V559D, V654A) | 4.1 |
| LATS1 | 100 |
| LATS2 | 96 |
| LCK | 2.2 |
| LIMK1 | 92 |
| LIMK2 | 100 |
| LKB1 | 100 |
| LOK | 0 |
| LRRK2 | 100 |
| LRRK2(G2019S) | 100 |
| LTK | 26 |
| LYN | 18 |
| LZK | 47 |
| MAK | 100 |
| MAP3K1 | 80 |
| MAP3K15 | 100 |
| MAP3K2 | 100 |
| MAP3K3 | 100 |
| MAP3K4 | 100 |
| MAP4K2 | 100 |
| MAP4K3 | 20 |
| MAP4K4 | 100 |
| MAP4K5 | 2.8 |
| MAPKAPK2 | 100 |
| MAPKAPK5 | 100 |
| MARK1 | 100 |
| MARK2 | 100 |
| MARK3 | 100 |
| MARK4 | 100 |
| MAST1 | 100 |
| MEK1 | 24 |
| MEK2 | 33 |
| MEK3 | 100 |
| MEK4 | 100 |
| MEK5 | 0.25 |
| MEK6 | 87 |
| MELK | 29 |
| MERTK | 2.1 |
| MET | 7.7 |
| MET(M1250T) | 3 |
| MET(Y1235D) | 4.4 |
| MINK | 100 |
| MKK7 | 100 |
| MKNK1 | 45 |
| MKNK2 | 0.05 |
| MLCK | 100 |
| MLK1 | 83 |
| MLK2 | 78 |
| MLK3 | 63 |
| MRCKA | 100 |
| MRCKB | 100 |
| MST1 | 100 |
| MST1R | 4 |
| MST2 | 100 |
| MST3 | 100 |
| MST4 | 80 |
| MTOR | 100 |
| MUSK | 13 |
| MYLK | 100 |
| MYLK2 | 100 |
| MYLK4 | 100 |
| MYO3A | 93 |
| MYO3B | 100 |
| NDR1 | 100 |
| NDR2 | 82 |
| NEK1 | 100 |
| NEK11 | 100 |
| NEK2 | 100 |
| NEK3 | 58 |
| NEK4 | 100 |
| NEK5 | 97 |
| NEK6 | 100 |
| NEK7 | 100 |
| NEK9 | 66 |
| NIM1 | 100 |
| NLK | 100 |
| CSR1 | 96 |
| P38-alpha | 53 |
| P38-beta | 87 |
| P38-delta | 53 |
| P38-gamma | 100 |
| PAK1 | 37 |
| PAK2 | 54 |
| PAK3 | 32 |
| PAK4 | 100 |
| PAK6 | 87 |
| PKA7 | 100 |
| PCTK1 | 100 |
| PCTK2 | 100 |
| PCTK3 | 100 |
| PDGFRA | 1.8 |
| PDGFRB | 0 |
| PDPK1 | 100 |
| PFCDPK1 (*P. falciparum*) | 84 |
| PFPK5 (*P. falciparum*) | 100 |
| PFTAIRE2 | 87 |
| PFTK | 100 |
| PHKG1 | 100 |
| PHKG2 | 96 |
| PIK3C2B | 100 |
| PIK3C2G | 98 |
| PIK3CA | 100 |
| PIK3CA(C420R) | 100 |
| PIK3CA(E542K) | 100 |
| PIK3CA(E545A) | 74 |
| PIK3CA(E545K) | 100 |
| PIK3CA (H1047L) | 100 |
| PIK3CA (H1047Y) | 63 |
| PIK3CA(I8DDL) | 100 |
| PIK3CA(M1043I) | 100 |
| PIK3CA(Q546K) | 100 |
| PIK3CB | 100 |
| PIK3CD | 100 |
| PIK3CG | 100 |
| PIK4CB | 100 |
| PIM1 | 96 |
| PIM2 | 67 |
| PIM3 | 67 |
| PIP5K1A | 100 |
| PIP5K1C | 100 |
| PIP5K2B | 100 |
| PIP5K2C | 38 |
| PAKC-alpha | 100 |
| PAKC-beta | 100 |
| PKMYT1 | 100 |
| PKN1 | 100 |
| PKN2 | 2.6 |

TABLE 5-continued

| Kinase Target Ambit Gene Symbol | Example 10 % Ctrl@1000 nM |
|---|---|
| PKNB (*M. tuberculosis*) | 96 |
| PLK1 | 100 |
| PLK2 | 83 |
| PLK3 | 100 |
| PLK4 | 7.4 |
| PRKCD | 100 |
| PRKCE | 100 |
| PRKCH | 100 |
| PRKCI | 100 |
| PRKCQ | 100 |
| PRKD1 | 100 |
| PRKD2 | 100 |
| PRKD3 | 88 |
| PRKG1 | 100 |
| PRKG2 | 100 |
| PRKR | 100 |
| PRKX | 81 |
| PRP4 | 76 |
| PYK2 | 19 |
| QSK | 100 |
| RAF1 | 100 |
| RET | 0.1 |
| RET (M918T) | 0.05 |
| RET (V804L) | 0.35 |
| RET (V804M) | 0.6 |
| RIOK1 | 100 |
| RIOK2 | 100 |
| RIOK3 | 100 |
| RIPK1 | 99 |
| RIPK2 | 30 |
| RIPK4 | 89 |
| RIPK5 | 82 |
| ROCK1 | 100 |
| ROCK2 | 100 |
| ROS1 | 29 |
| RPS6KA4((kin.Dom.1-N-termimal) | 76 |
| RPS6KA4((kin.Dom.2-C-termimal) | 100 |
| RPS6KA5((kin.Dom.1-N-termimal) | 100 |
| RPS6KA5((kin.Dom.2-C-termimal) | 83 |
| RSK1(Kin.Dom.1-N-terminal) | 59 |
| RSK1(Kin.Dom.2-C-terminal) | 100 |
| RSK2(Kin.Dom.1-N-terminal) | 100 |
| RSK3(Kin.Dom.1-N-terminal) | 100 |
| RSK3(Kin.Dom.2-C-terminal) | 100 |
| RSK4(Kin.Dom.1-N-terminal) | 77 |
| RSK4(Kin.Dom.2-C-terminal) | 91 |
| S6K1 | 89 |
| SBK1 | 100 |
| SgK110 | 100 |
| SGK3 | 75 |
| SIK | 60 |
| SIK2 | 100 |
| SLK | 7.4 |
| SNARK | 100 |
| SNRK | 100 |
| SRC | 3.2 |
| SRMS | 8.9 |
| SRPK1 | 70 |
| SRPK2 | 100 |
| SRPK3 | 100 |
| STK16 | 77 |
| STK33 | 46 |
| STK35 | 82 |
| STK36 | 100 |
| STK39 | 100 |
| SYK | 58 |
| TAK1 | 75 |
| TAOK1 | 100 |
| TAOK2 | 70 |
| TAOK3 | 100 |
| TBK1 | 79 |
| TEC | 100 |
| TESK1 | 39 |
| TGFBR1 | 100 |
| TGFBR2 | 100 |
| TIE1 | 4 |
| TIE2 | 2.4 |
| TLK1 | 88 |
| TLK2 | 100 |
| TNIK | 70 |
| TNK1 | 30 |
| TNK2 | 94 |
| TNNI3K | 94 |
| TRAK | 1.8 |
| TRKB | 4 |
| TRKC | 2.2 |
| TRPM6 | 86 |
| TSSK1B | 100 |
| TTK | 84 |
| TXK | 62 |
| TYK2(JH1domain-catalytic) | 92 |
| TYK2(JH1domain-pseudokinase) | 100 |
| TYRO3 | 41 |
| ULK1 | 100 |
| ULK2 | 100 |
| ULK3 | 82 |
| VEGFR2 | 3.9 |
| VRK2 | 100 |
| WEE1 | 100 |
| WEE2 | 100 |
| YANK1 | 100 |
| YANK2 | 100 |
| YANK3 | 100 |
| YES | 20 |
| YSK1 | 57 |
| YSK4 | 1.7 |
| ZAK | 36 |
| ZAP7C | 81 |

EXAMPLE 17

Inhibitory activity on the kinases in tumor cells: In this example, the compound prepared in Example 10, N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide is tested in tumor cells by ProQinase GmbH corporation (Breisacher Str. 117, D-79106 Freiburg, Germany. www.proqinase.com) for the inhibitory activity on the following kinases: c-KIT, c-MET, VEGFR2 and PDGFR-β. The test includes the following steps:

Firstly, the compound according to present invention is dissolved in dimethyl sulfoxide (DMSO) to prepare a 10 mM stock solution, which is diluted serially according to the concentration range shown in Table 6:

TABLE 6

| compound | concentration of the stock solution [M] | testing range [M] c-KIT | testing range [M] c-MET | testing range [M] VEGFR2 | testing range [M] PDGFR-β |
|---|---|---|---|---|---|
| the compound prepared in Example 10 | $1.0 \times 10^{-2}$ | $1.0 \times 10^{-5} - 1.0 \times 10^{-9}$ | $1.0 \times 10^{-5} - 1.0 \times 10^{-9}$ | $1.0 \times 10^{-5} - 1.0 \times 10^{-9}$ | $1.0 \times 10^{-5} - 1.0 \times 10^{-9}$ |

Cell Culture c-KIT kinase: in the test experiment of KIT kinase phosphorylation in the cells, human acute megakaryocytic leukemia cell line M07e having endogenous high expression wild type c-KIT is used. When these cells are stimulated with human stem cell factor (SCF), the tyrosine of KIT receptor kinases is self-phosphorylated. M07e cells are inoculated in RPMI containing 20% fetal calf serum (FCS) and 10 ng/ml GM-CSF in a multi-well cell culture dish. The compound of the invention is added to the cells after overnight starvation of serum and growth factor, then the cells are cultured in a medium without serum.

c-MET kinase: in the test experiment of c-MET kinase phosphorylation in the cells, human gastric cancer cell line MKN45 having endogenous high expression wild type c-MET (wild-type c-MET) is used. Such high expression of c-MET causes the tyrosine of c-MET receptor kinases constantly self-phosphorylated without ligands. MKN45 cells are inoculated in DMEM culture solution containing 10% FCS in a multi-well cell culture dish. The compound of the invention is added to the cells after serum overnight starvation, then the cells are cultured in a medium without serum.

VEGFR2 kinase: in the test experiment of VEGFR2 kinase phosphorylation in the cells, a spontaneous immortalized human umbilical vein endothelial cell line HUE having endogenous high expression vascular endothelial growth factor-R2 (VEGFR2) is used. When these cells are simulated with human vascular endothelial growth factor-A (VEGF-A), it causes the tyrosine of VEGFR2 receptor kinases self-phosphorylated. HUE cells are inoculated in endothelial cell growth medium (ECGM) containing 10% FCS in a multi-well cell culture dish. The compound of the invention is added to the cells after serum overnight starvation in endothelial cell growth medium (ECGM) containing 10% FCS, then the cells cultured in a ECGM culture solution without serum.

PDGFR-β kinase: in the test experiment of PDGFR-beta kinase phosphorylation in the cells, mouse embryo fibroblast cell line NIH3T3 having endogenous high expression wild type PDGFR-β (wild-type PDGFR-β) is used. When these cells are simulated with mouse platelet-derived growth factor BB (PDGF-BB), it causes the tyrosine of PDGFR-beta receptor kinases self-phosphorylated. NIH3T3 cells are inoculated in DMEM culture solution containing 10% FCS in a multi-well cell culture dish. The compound of the invention is added to the cells after serum overnight starvation, then the cells are cultured in a medium without serum.

Test Method

The diluted stock solution sample of the compound according to the invention is added to cell culture solution in a ratio of 1:100 until a final DMSO concentration of 1% is reached. After culturing at 37° C. for 90 min, the cells are stimulated according to Table 7 (quantitative method: sandwich ELISA: Substrate phosphorylation is quantitated through 96-well sandwich ELISA method by using capture antibody of specific substrate and detection antibody of dephosphorylated tyrosine. $IC_{50}$ values are determined by using GraphPad Prism 5.01 software):

TABLE 7

| target | ligand | concentration | time |
|---|---|---|---|
| c-KIT | SCF | 100 ng/mL | 3 min |
| c-MET | | without stimulation | |
| PDGFR-β | PDGF-BB | 100 ng/mL | 3 min |
| VEGFR2 | VEGF-A | 100 ng/mL | 3 min |

Test Results

By drawing titration curve of N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide inhibiting c-KIT, c-MET, VEGFR2 and PDGFR-β in the cells, $IC_{50}$ values of the compound inhibiting the above four kinases are obtained, shown in Table 8:

TABLE 8

| | $IC_{50}$ values in the cell* | | | |
|---|---|---|---|---|
| compound | c-KIT | c-MET | VEGFR2 | PDGFR-β |
| the compound prepared in Example 10 | 27 nM | 17 nM | 0.43 nM | 13 nM |

*mean value of two testing results

It can be seen from the above data that, the compound according to the present invention has significant inhibitory effect on several kinases, i.e., c-Met, c-KIT, VEGFR2 and PDGFR-β in tumor cells, their $IC_{50}$ values are in the range of 0.43-27 nM.

EXAMPLE 18

Anti-tumor experiments: in this example, N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide obtained from Example 3 is used in the anti-tumor experiments in nude mice animal model of xenograft GTL-16 human gastric cancer cells, the methods and results are as follows:

Materials 7-8 weeks old SPF level female BALB/c-nu/nu mice with 16-20 g of body weights are purchased from Experimental Animal Center of Guangdong Province, inspection certificate number: NO:0072659. GTL-16 gastric cancer cells are purchased from the Cell Source Center of Shanghai Institutes for Biological Sciences. RPM 1-1640 cell culture medium, fetal calf serum (FBS) and digestive juice of trypsin are from Gibco Corporation. All the antibiotics are purchased from Sigma Company.

Methods

Firstly culturing the GTL-16 gastric cancer cells: GTL-16 cell line is inoculated in RPM 1-1640 culture solution containing 10% FBS, 100 U/ml penicillin, 100 U/ml streptomycin, and cultured at 37° C., 5% $CO_2$, 100% humidity in a carbon dioxide cell incubator, the cells enter into logarithmic growth phase after 24 hours, after 48 hours of inoculation, the cells grow to cover the bottom of the culture bottle. Then the GTL-16 cells covering 80% bottom of the culture bottle are digested, 5 minutes after centrifuging at 1000 r/min, the cells are diluted to $2\times10^7$/ml and implanted subcutaneously in the right anterior axillary fossa with 0.1 ml per mouse. After 12 days after tumor cells were implanted, the tumor-bearing nude mice are weighted, the sizes of the tumors are measured and the mice with tumors in a size range of 40-160 $mm^3$ are randomly divided into vehicle group (vehicle, 0.2% aqueous methylsulfonic acid solution) and treatment group using the compound prepared in Example 3, N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide (which is dissolved in 0.2% aqueous methylsulfonic acid solution with a concentration of 5 mg/mL), 8 mice per group; thereafter the nude mice are weighted each day and administrated orally in a mount of 0.1 mL/10 g body weight by gavage method (50 mg/kg qd via p.o), the sizes of tumors on each animal are measured every other days, after 14 days, the tumor-bearing mice are sacrificed with cervical spine articulation, and the tumors are taken out to weight. The calculation method of Tumor Growth Inhibition (TGI): the experimental data are expressed as mean±SD; $TGI=[(V_{vehicle\ group}-V_{treatment\ group}) \div V_{vehicle\ group}]\times 100\%$. $V_{vehicle\ group}$ means tumor volume of vehicle group mice; $V_{treatment\ group}$ means tumor volume of treatment group mice.

Results

Figure 2:
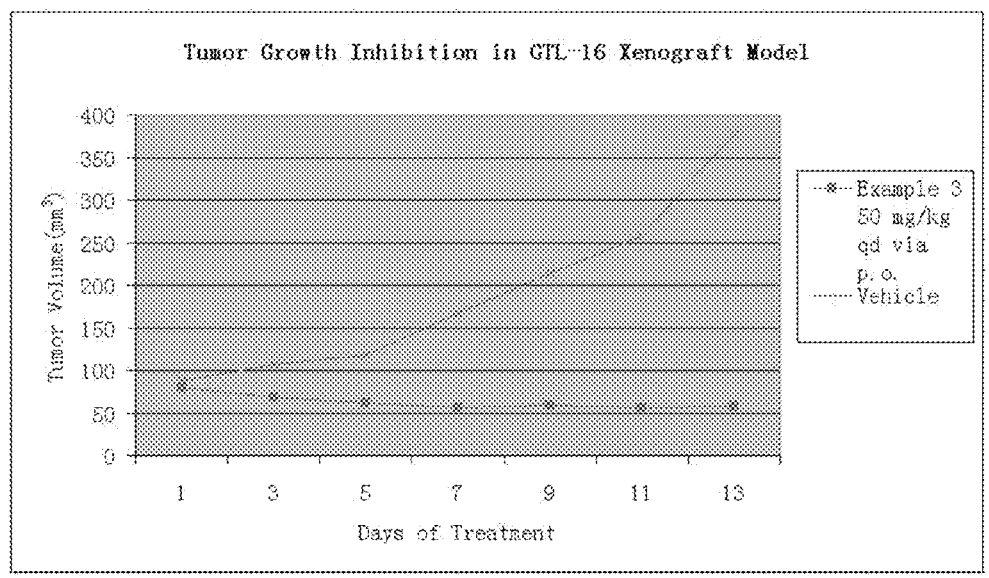
FIG. 2 is the curve of tumor sizes from the GTL-16 xenograft mouse models.

The tumor inhibitory effect of the compound according to present invention prepared in Example 3 on mice tumor in the treatment group: vehicle group and treatment group are respectively fed with vehicle and drug solution, after 14 days the average tumor volumes of the vehicle group and treatment group animals are 377.1±244.5 $mm^3$ (n=7) and 57.1±61.2 (n=8) in respective; thus TGI of the treatment group is 85%. As compared with the initial tumor volumes, the tumor sizes of the treatment group are significantly reduced. The comparisons of tumor tissues are shown in FIG. 1, and the comparisons of the experimental curves are shown in FIG. 2.

Figure 3:
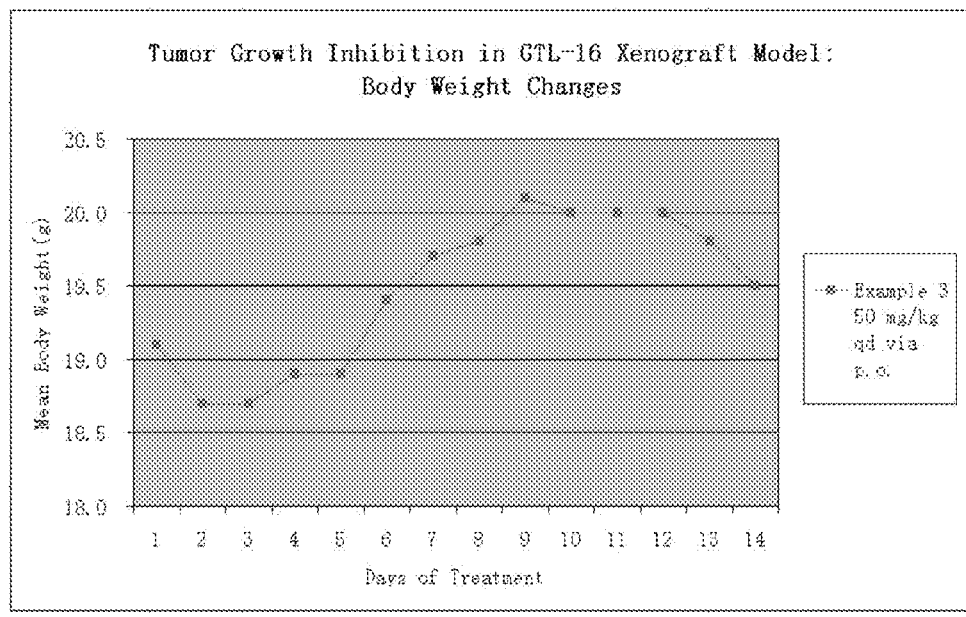
FIG. 3 is the curve showing the body weight changes in the GTL-16 xenograft mouse models.
Figure 4:
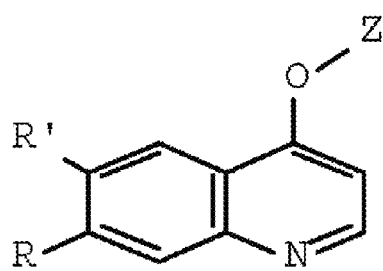
FIG. 4 is the molecular structure of the compound according to the invention.

Body weight changes for mice in vehicle group and treatment group are shown in FIG. 3: after treating for 14 days, the body weight of mice in the treatment group using the compound of Example 3 had little change (<5%).

It can be seen from the results of the above anti-tumor experiments that, in nude mice xenograft animal models, the representative compound of the present invention exhibits significant anti-tumor effect, administrating orally in a dose of 50 mg/kg, once daily, after 14 days TGI reaches 85%. Body weight of the animals in treatment group substantively do not reduce, this demonstrates that the drug has no significant toxicity.

EXAMPLE 19

Drug Ingredients and Formulation
Tablet (mg/tablet)
The compound prepared in Example 1: 100;
Lactose, Ph EUR: 182.75;
Sodium carboxymethylcellulose: 12.0;
Corn starch slurry (5 w/v %): 2.25;
Magnesium stearate: 3.0;
Applicable People
Applicable to patients suffering from protein kinase abnormal activity-associated diseases.

EXAMPLE 20

Drug Ingredients and Formulation
Tablet (mg/tablet)
The compound prepared in Example 5: 100; the contents of other materials are the same as those in Example 19.
Applicable People
Applicable to patients suffering from protein kinase abnormal activity-associated diseases.

EXAMPLE 21

Drug Ingredients and Formulation
Tablet (mg/tablet)
The compound prepared in Example 1: 50;
Lactose, Ph EUR: 223.75;
Sodium carboxymethylcellulose: 6.0;
Corn starch: 15.0;
Polyvinylpyrrolidone (5 w/v %): 2.25;
Magnesium stearate: 3.0;
Applicable People
Applicable to patients suffering from protein kinase abnormal activity-associated diseases.

EXAMPLE 22

Drug Ingredients and Formulation
Tablet (mg/tablet)
The compound prepared in Example 3: 50; the contents of other materials are the same as those in Example 21;
Applicable People
Applicable to patients suffering from protein kinase abnormal activity-associated diseases.

EXAMPLE 23

Drug Ingredients and Formulation
Tablet (mg/tablet)
The compound prepared in Example 7: 1.0;
Lactose, Ph EUR: 93.25;
Sodium carboxymethylcellulose: 4.0;
Corn starch slurry (5 w/v %): 0.75;
Magnesium stearate: 76;
Applicable People
Applicable to patients suffering from protein kinase abnormal activity-associated diseases.

EXAMPLE 24

Drug Ingredients and Formulation
Tablet (mg/tablet)
The compound prepared in Example 5: 1.0; the contents of other materials are the same as those in Example 23;
Applicable People
Applicable to patients suffering from protein kinase abnormal activity-associated diseases.

EXAMPLE 25

Drug Ingredients and Formulation
Capsule (mg/capsule)
The compound prepared in Example 7: 10.0;
Lactose, Ph EUR: 488.5;
Magnesium: 1.5;
Applicable People
Applicable to patients suffering from protein kinase abnormal activity-associated diseases.

EXAMPLE 26

Drug Ingredients and Formulation
Capsule (mg/capsule)
The compound prepared in Example 2: 10.0; the contents of other materials are the same as those in Example 25;
Applicable People
Applicable to patients suffering from protein kinase abnormal activity-associated diseases.

EXAMPLE 27

Drug Ingredients and Formulation
Injection (50 mg/ml)
The compound prepared in Example 6: 5%;
M Sodium hydroxide solution: 15%;
(a) M hydrochloric acid solution (pH is adjusted to 7.6);
Polyenthylene glycol 400: 5%;
Adjusting to 100% with water for injection;
Applicable People
Applicable to patients suffering from protein kinase abnormal activity-associated diseases.

EXAMPLE 28

Drug Ingredients and Formulation
Injection (50 mg/ml)
The compound prepared in Example 12: 5%; the contents of other materials are the same as those in Example 27; finally adjusting to 100% with water for injection;
Applicable People
Applicable to patients suffering from protein kinase abnormal activity-associated diseases.

EXAMPLE 29

Drug Ingredients and Formulation
Injection (10 mg/ml)
The compound prepared in Example 11: 1%;
Disodium hydrogen phosphate BP: 3.6%;
0.1M Sodium hydroxide solution: 15%;
Adjusting to 100% with water for injection;
Applicable People
Applicable to patients suffering from protein kinase abnormal activity-associated diseases.

EXAMPLE 30

Drug Ingredients and Formulation
Injection (10 mg/ml)
The compound prepared in Example 9: 1%; the contents of other materials are the same as those in Example 29; adjusting to 100% with water for injection;
Applicable People
Applicable to patients suffering from protein kinase abnormal activity-associated diseases.

EXAMPLE 31

Drug Ingredients and Formulation
Injection (1 mg/ml) (pH is adjusted to 6)
The compound prepared in Example 6: 0.1%;
Disodium hydrogen phosphate BP: 2.26%;
Citric acid: 0.38%;
Polyenthylene glycol 400: 3.5%;
Water for injection (for adjusting to 100%);
Applicable People
Applicable to patients suffering from protein kinase abnormal activity-associated diseases.

EXAMPLE 32

Drug Ingredients and Formulation
Injection (1 mg/ml) (pH is adjusted to 6)
The compound prepared in Example 10: 0.1%; the contents of other materials are the same as those in Example 31; finally water for injection is used to adjust the content to 100%;
Applicable People
Applicable to patients suffering from protein kinase abnormal activity-associated diseases.

EXAMPLE 33

Drug Ingredients and Formulation
Aerosol (mg/ml)
The compound prepared in Example 1: 10;
Sorbitan oleate: 13.5;
Trichlorofluoromethane: 910.0;
Dichlorodifluoromethane: 490.0;
Applicable People
Applicable to patients suffering from protein kinase abnormal activity-associated diseases.

EXAMPLE 34

Drug Ingredients and Formulation
Aerosol (mg/ml)
The compound prepared in Example 3: 10; the contents of other materials are the same as those in Example 33;
Applicable People
Applicable to patients suffering from protein kinase abnormal activity-associated diseases.

EXAMPLE 35

Drug Ingredients and Formulation
Aerosol (mg/ml)
The compound prepared in Example 4: 0.2;
Sorbitan oleate: 0.27;
Trichlorofluoromethane: 70.0;
Dichlorodifluoromethane: 280.0;
Dichlorotetrafluoroethane: 1094.0;
Applicable People
Applicable to patients suffering from protein kinase abnormal activity-associated diseases.

EXAMPLE 36

Drug Ingredients and Formulation
Aerosol (mg/ml)
The compound prepared in Example 7: 0.2; the contents of other materials are the same as those in Example 35;
Applicable People
Applicable to patients suffering from protein kinase abnormal activity-associated diseases.

EXAMPLE 37

Drug Ingredients and Formulation
Aerosol (mg/ml)
The compound prepared in Example 8: 2.5;
Sorbitan oleate: 3.38;
Trichlorofluoromethane: 67.5;
Dichlorodifluoromethane: 1086.0;
Dichlorotetrafluoroethane: 191.60;
Applicable People
Applicable to patients suffering from protein kinase abnormal activity-associated diseases.

EXAMPLE 38

Drug Ingredients and Formulation

Aerosol (mg/ml)

The compound prepared in Example 11: 2.5; the contents of other materials are the same as those in Example 37;

Applicable People

Applicable to patients suffering from protein kinase abnormal activity-associated diseases.

EXAMPLE 39

Drug Ingredients and Formulation

Aerosol (mg/ml)

The compound prepared in Example 4: 2.5;

Soybean lecithin: 2.7;

Trichlorofluoromethane: 67.5;

Dichlorodifluoromethane: 1086.0;

Dichlorotetrafluoroethane: 191.60;

Applicable People

Applicable to patients suffering from protein kinase abnormal activity-associated diseases.

EXAMPLE 40

Drug Ingredients and Formulation

Aerosol (mg/ml)

The compound prepared in Example 13: 2.5; the contents of other materials are the same as those in Example 39;

Applicable People

Applicable to patients suffering from protein kinase abnormal activity-associated diseases.

EXAMPLE 41

Drug Ingredients and Formulation

Ointment (/ml)

The compound prepared in Example 1: 40 mg;

Ethanol: 300 µL;

Water: 300 µL;

1-dodecyl azacycloheptanone: 50 µL;

Propanediol: to 1 ml;

Applicable People

Applicable to patients suffering from protein kinase abnormal activity-associated diseases.

EXAMPLE 42

Drug Ingredients and Formulation

Ointment (/ml)

The compound prepared in Example 7: 40 mg; the contents of other materials are the same as those in Example 41;

Applicable People

Applicable to patients suffering from protein kinase abnormal activity-associated diseases.

What is claimed is:

1. A compound comprising a phosphorus-containing group-substituted quinoline, wherein the compound is represented by formula (I) below:

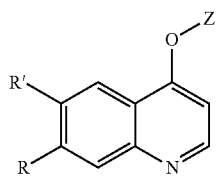

(I)

in formula (I),

Z represents

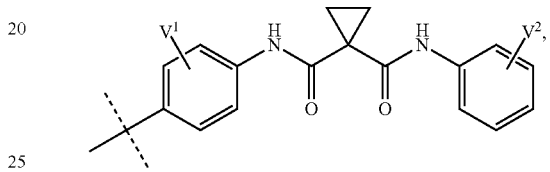

$V^1$ and $V^2$ are each independently selected from hydrogen, halogen, —$OCF_3$, —$CF_3$, —$NO_2$, —CN, —OH, —$NH_2$, —$NMe_2$, $C_{1-6}$ alkyl, $C_{3-6}$ cycloalkyl, $C_{3-6}$ heterocycloalkyl, $C_{1-6}$ alkoxy, $C_{3-6}$ cycloalkoxy, or $C_{3-6}$ heterocycloalkoxy;

either of R and R' represents phosphorus-containing substituent Q, the other is selected from hydrogen, methoxyl, methoxyethoxyl, or phosphorus-containing substituent Q;

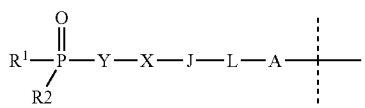

wherein, the phosphorus-containing substituent Q represents,

A is absent or represents O, NH, $S(=O)_m$, or $C_{1-6}$ alkyl, and A is optionally substituted with $G^1$;

L is absent or represents $C_{1-6}$ alkyl, $C_{3-6}$ cycloalkyl, $C_6$ aryl, $C_{5-6}$ heteroaryl, or $C_{3-6}$ heterocycloalkyl, and L is optionally substituted with $G^2$;

J is absent or represents O, NH, $S(=O)_m$, $C_{1-6}$ alkyl, $C_{3-6}$ cycloalkyl, $C_6$ aryl, $C_{5-6}$ heteroaryl, or $C_{3-6}$ heterocycloalkyl and J is optionally substituted with $G^3$;

X is absent or represents —C(=O)—, —S(O)$_m$—, $C_{1-6}$ alkyl, $C_{3-6}$ cycloalkyl, $C_6$ aryl, $C_{5-6}$ heteroaryl, or $C_{3-6}$ heterocycloalkyl, and X is optionally substituted with $G^4$;

Y is absent or represents $C_{1-6}$ alkyl, $C_{3-6}$ cycloalkyl, $C_6$ aryl, $C_{5-6}$ heteroaryl, or $C_{3-6}$ heterocycloalkyl, and Y is optionally substituted with $G^5$;

$R^1$ and $R^2$ are each independently selected from —OH, $C_{1-6}$ alkyl, $C_{3-6}$ cycloalkyl, $C_6$ aryl, $C_{5-6}$ heteroaryl, $C_{3-6}$ heterocycloalkyl, $C_{1-6}$ alkoxy, $C_{3-6}$ cycloalkoxy, $C_6$ aryloxy, $C_{5-6}$ heteroaryloxy, or $C_{3-6}$ heterocycloalkoxy, and $R^1$ and $R^2$ are each optionally substituted with $G^6$;

$R^1$ and $R^2$ together with the phosphorus atom to which they are attached may form a $C_{3-6}$ heterocycloalkyl ring, this $C_{3-6}$ heterocycloalkyl ring may further comprise heteroatom(s) selected from O, N, or $S(=O)_m$;

wherein, $G^1$, $G^2$, $G^3$, $G^4$, $G^5$ and $G^6$ are each independently selected from H, —CN, —CF$_3$, —CO$_2$H, halogen, C$_{1-6}$ alkyl, C$_{3-6}$ cycloalkyl, C$_{2-6}$ alkenyl, C$_{2-6}$ alkynyl, C$_6$ aryl, C$_{5-6}$ heteroaryl, C$_{3-6}$ heterocycloalkyl, R$^3$O—, R$^3$R$^4$N—, R$^3$S(=O)$_m$—, R$^3$R$^4$NS(=O)$_m$—, R$^5$C(=O)—, R$^3$R$^4$NC(=O)—, R$^3$OC(=O)—, R$^5$C(=O)O—, R$^3$R$^4$NC(=O)O—, R$^5$C(=O)NR$^3$—, R$^3$R$^4$NC(=O)NR$^6$—, R$^3$OC(=O)NR$^6$—, R$^3$S(=O)$_m$NR$^6$—, R$^3$R$^4$NS(=O)$_m$NR$^6$—, R$^3$R$^4$NC(=NR$^7$)NR$^6$—, R$^3$R$^4$NC(=CHNO$_2$)NR$^6$—, R$^3$R$^4$NC(=N—CN)NR$^6$—, R$^3$R$^4$NC(=NR$^7$)—, R$^3$S(=O)(=NR$^7$)NR$^6$—, or R$^3$R$^4$NS(=O)(=NR$^7$)—;

R$^3$, R$^4$, R$^5$, R$^6$ and R$^7$ are each independently selected from H, C$_{1-6}$ alkyl, C$_{3-6}$ cycloalkyl, C$_6$ aryl, C$_{5-6}$ heteroaryl, or C$_{3-6}$ heterocycloalkyl; when R$^3$ and R$^4$ are attached to the same nitrogen atom, R$^3$ and R$^4$ together with the nitrogen to which they are attached may form a C$_{3-6}$ heterocycloalkyl ring, this C$_{3-6}$ heterocycloalkyl ring may further comprise heteroatom(s) selected from O, N, or S(=O)$_m$; and R$^3$, R$^4$, R$^5$, R$^6$ and R$^7$ may be optionally substituted with halogen, CN, C$_{1-6}$ alkyl, or C$_{3-6}$ cycloalkyl;

m=0-2;

or a racemate or enantiomer thereof.

2. The compound of claim 1, wherein the compound is represented by formula (Ia) below:

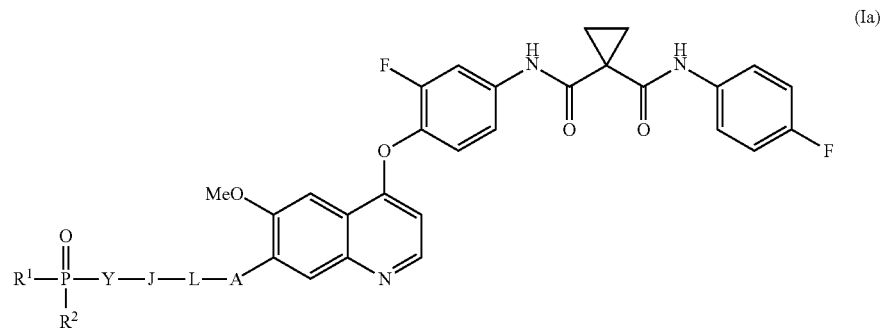

(Ia)

in the above formula,

A represents O, NH, or S(=O)$_m$, and A is optionally substituted with G$^1$;

L represents C$_{1-6}$ alkyl, or C$_{3-6}$ cycloalkyl, and L is optionally substituted with G$^2$;

J represents O, NH, or S(=O)$_m$, and J is optionally substituted with G$^3$;

Y represents C$_{1-6}$ alkyl, or C$_{3-6}$ cycloalkyl, and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;

m=0-2;

or a racemate or enantiomer thereof.

3. The compound of claim 1, wherein the compound is represented by formula (Ib) below:

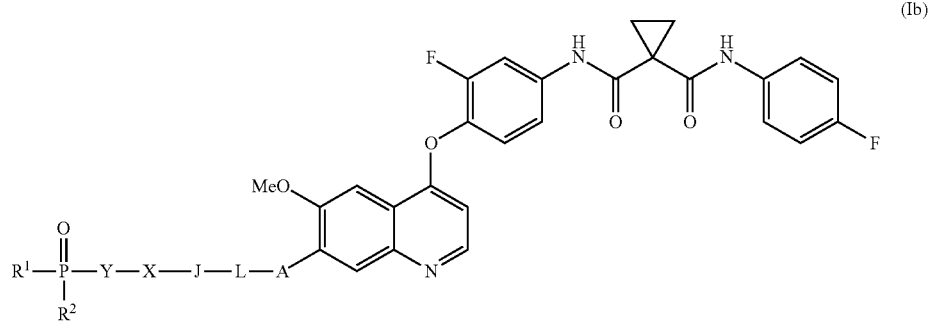

(Ib)

in the above formula,

A represents O, NH, or S(=O)$_m$, and A is optionally substituted with G$^1$;

L represents C$_{1-6}$ alkyl, and L is optionally substituted with G$^2$;

J represents C$_{3-6}$ cycloalkyl, or C$_{3-6}$ heterocycloalkyl, and J is optionally substituted with G$^3$;

X is absent or represents —C(=O)—, or —S(O)$_m$—;

Y represents C$_{1-6}$ alkyl, or C$_{3-6}$ cycloalkyl; and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;

m=0-2;

or a racemate or enantiomer thereof.

4. The compound of claim 1, wherein the compound is represented by formula (Ic) below:

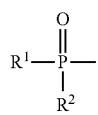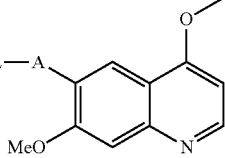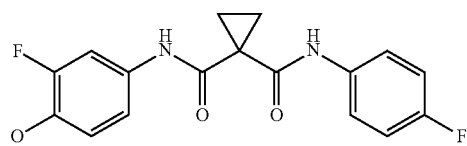

(Ic)

in the above formula,

A represents O, NH, or S(=O)$_m$, and A is optionally substituted with G$^1$;

L represents C$_{1-6}$ alkyl, or C$_{3-6}$ cycloalkyl, and L is optionally substituted with G$^2$;

J represents O, NH, or S(=O)$_m$, and J is optionally substituted with G$^3$;

Y represents C$_{1-6}$ alkyl, or C$_{3-6}$ cycloalkyl, and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;

m=0-2;

or a racemate or enantiomer thereof.

5. The phosphorus-containing group-substituted quinoline according to claim 1, wherein the compound is represented by formula (Id) below:

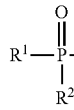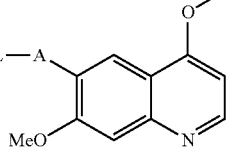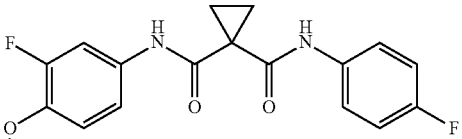

(Id)

in the above formula,

A represents O, NH, or S(=O)$_m$, and A is optionally substituted with G$^1$;

L represents C$_{1-6}$ alkyl, and L is optionally substituted with G$^2$;

J represents C$_{3-6}$ cycloalkyl, or C$_{3-6}$ heterocycloalkyl, and J is optionally substituted with G$^3$;

X is absent or represents —C(=O)—, or —S(O)$_m$—;

Y represents C$_{1-6}$ alkyl, or C$_{3-6}$ cycloalkyl, and Y is optionally substituted with G$^5$;

R$^1$ and R$^2$ are each independently selected from —OH, C$_{1-6}$ alkyl, C$_{3-6}$ cycloalkyl, C$_6$ aryl, C$_{5-6}$ heteroaryl, C$_{3-6}$ heterocycloalkyl, C$_{1-6}$ alkoxy, C$_{3-6}$ cycloalkoxy, C$_6$ aryloxy, C$_{5-6}$ heteroaryloxy, or C$_{3-6}$ heterocycloalkoxy, and R$^1$ and R$^2$ are each optionally substituted with G$^6$;

m=0-2;

or a racemate or enantiomer thereof.

6. The compound of claim 1, wherein the compound is represented by formula (Ie) below:

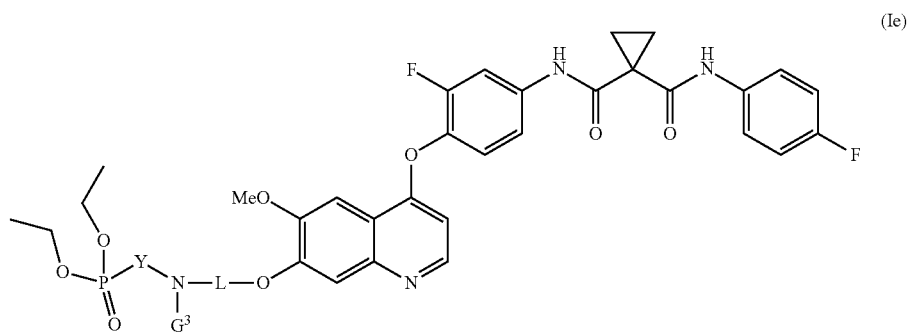

(Ie)

in the above formula,

L represents C$_{1-6}$ alkyl, or C$_{3-6}$ cycloalkyl, and L is optionally substituted with G$^2$;

Y represents C$_{1-6}$ alkyl, or C$_{3-6}$ cycloalkyl, and Y is optionally substituted with G$^5$;

or a racemate or enantiomer thereof.

7. The compound of claim 1, wherein the compound is represented by formula (If) below:

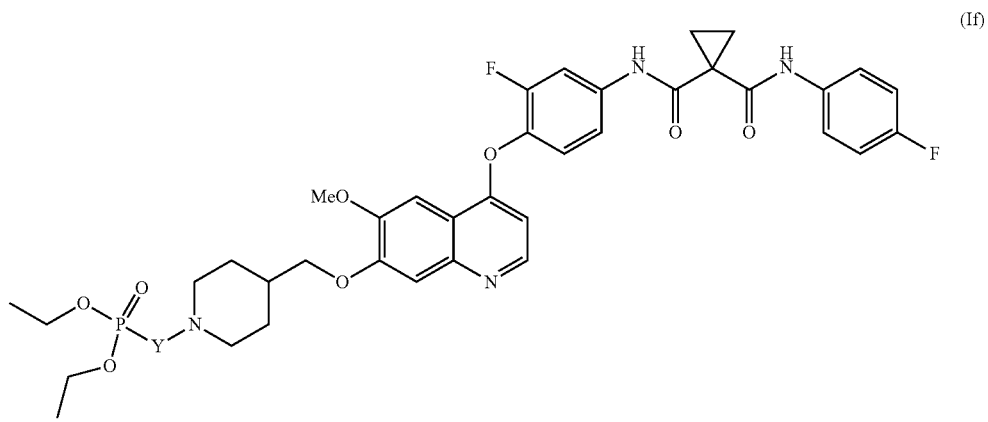

(If)

in the above formula,

Y represents C$_{1-6}$ alkyl, or C$_{3-6}$ cycloalkyl, and Y is optionally substituted with G$^5$;
or a racemate or enantiomer thereof.

8. The compound of claim 1, wherein the compound is selected from the group consisting of one or more of the following compounds:

N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethylamino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(methyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(n-propyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(methyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(n-propyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(diethoxyphosphorylmethyl)(ethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(acetyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(formyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(propionyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(isopropionyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(cyclopropylformyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide;

N1-[4-[[7-[3-(acetyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(formyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(propionyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(isopropionyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1-[4-[[7-[3-(cyclopropylformyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide;

N1'-[4-[[7-[3-(aminocarbonyl(diethoxyphosphorylmethyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(ethylaminocarbonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(methylaminocarbonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(N,N'-dimethylaminocarbonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(aminocarbonyl(diethoxyphosphorylmethyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(ethylaminocarbonyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(methylaminocarbonyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(N,N'-dimethylaminocarbonyl)amino)ethoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(methylsulfonyl)amino)propoxyl]-6-methoxyl-4-quinolyl]oxyl]-3-fluorophenyl]-N1-(4-fluorophenyl)cyclopropane-1,1-dicarboxamide;

N1'-[4-[[7-[3-(diethoxyphosphorylmethyl)(ethylsulfonyl)amino)propoxyl]-6-methoxyl-4-quinolyl]oxyl]-3-fluorophenyl]-N1-(4-fluorophenyl)cyclopropane-1,1-dicarboxamide;

N1-[4-[[6-[3-(diethoxyphosphorylmethylamino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethylamino)ethoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(methyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(ethyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(n-propyl)amino)propoxyl]-7-methoxyl-4-quinolyl]oxyl]-3-fluorophenyl]-N1'-(4-fluorophenyl)cyclopropane-1,1-dicarboxamide;

N1-[4-[[6-[3-(diethoxyphosphorylmethyl)(ethyl)amino)
propoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(diethoxyphosphorylmethyl)(methyl)
amino)ethoxyl]-7-methoxyl-4-quinolyl]oxyl]-3-fluo-
rophenyl]-N1'-(4-fluorophenyl)cyclopropane-1,1-di-
carboxamide;

N1-[4-[[6-[3-(diethoxyphosphorylmethyl)(ethyl)amino)
ethoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(diethoxyphosphorylmethyl)(n-propyl)
amino)ethoxyl]-7-methoxyl-4-quinolyl]oxyl]-3-fluo-
rophenyl]-N1'-(4-fluorophenyl)cyclopropane-1,1-di-
carboxamide;

N1-[4-[[6-[3-(diethoxyphosphorylmethyl)(ethyl)amino)
ethoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(acetyl(diethoxyphosphorylmethyl)amino)
propoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(formyl(diethoxyphosphorylmethyl)amino)
propoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(propionyl(diethoxyphosphorylmethyl)
amino)propoxyl]-7-methoxyl-4-quinolyl]oxyl]-3-fluo-
rophenyl]-N1'-(4-fluorophenyl)cyclopropane-1,1-di-
carboxamide;

N1-[4-[[6-[3-(isopropionyl(diethoxyphosphorylmethyl)
amino)propoxyl]-7-methoxyl-4-quinolyl]oxyl]-3-fluo-
rophenyl]-N1'-(4-fluorophenyl)cyclopropane-1,1-di-
carboxamide;

N1-[4-[[6-[3-(cyclopropylformyl(diethoxyphosphorylm-
ethyl)amino)propoxyl]-7-methoxyl-4-quinolyl]oxyl]-
3-fluorophenyl]-N1'-(4-fluorophenyl)cyclopropane-1,
1-dicarboxamide;

N1-[4-[[6-[3-(acetyl(diethoxyphosphorylmethyl)amino)
ethoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(formyl(diethoxyphosphorylmethyl)amino)
ethoxyl]-7-methoxyl-4-quinolyl]oxyl]-3-fluorophe-
nyl]-N1'-(4-fluorophenyl)cyclopropane-1,1-dicarboxa-
mide;

N1-[4-[[6-[3-(propionyl(diethoxyphosphorylmethyl)
amino)ethoxyl]-7-methoxyl-4-quinolyl]oxyl]-3-fluo-
rophenyl]-N1'-(4-fluorophenyl)cyclopropane-1,1-di-
carboxamide;

N1-[4-[[6-[3-(isopropionyl(diethoxyphosphorylmethyl)
amino)ethoxyl]-7-methoxyl-4-quinolyl]oxyl]-3-fluo-
rophenyl]-N1'-(4-fluorophenyl)cyclopropane-1,1-di-
carboxamide;

N1-[4-[[6-[3-(cyclopropylformyl(diethoxyphosphorylm-
ethyl)amino)ethoxyl]-7-methoxyl-4-quinolyl]oxyl]-3-
fluorophenyl]-N1'-(4-fluorophenyl)cyclopropane-1,1-
dicarboxamide;

N1'-[4-[[6-[3-(aminocarbonyl(diethoxyphosphorylm-
ethyl)amino)propoxyl]-7-methoxyl-4-quinolyl]oxyl]-
3-fluorophenyl]-N1-(4-fluorophenyl)cyclopropane-1,
1-dicarboxamide;

N1'-[4-[[6-[3-(diethoxyphosphorylmethyl)(ethylami-
nocarbonyl)amino)propoxyl]-7-methoxyl-4-quinolyl]
oxyl]-3-fluorophenyl]-N1-(4-fluorophenyl)cyclopro-
pane-1,1-dicarboxamide;

N1'-[4-[[6-[3-(diethoxyphosphorylmethyl)(methylami-
nocarbonyl)amino)propoxyl]-7-methoxyl-4-quinolyl]
oxyl]-3-fluorophenyl]-N1-(4-fluorophenyl)cyclopro-
pane-1,1-dicarboxamide;

N1'-[4-[[6-[3-(diethoxyphosphorylmethyl)(N,N'-dim-
ethylaminocarbonyl)amino)propoxyl]-7-methoxyl-4-
quinolyl]oxyl]-3-fluorophenyl]-N1-(4-fluorophenyl)
cyclopropane-1,1-dicarboxamide;

N1'-[4-[[6-[3-(aminocarbonyl(diethoxyphosphorylm-
ethyl)amino)ethoxyl]-7-methoxyl-4-quinolyl]oxyl]-3-
fluorophenyl]-N1-(4-fluorophenyl)cyclopropane-1,1-
dicarboxamide;

N1'-[4-[[6-[3-(diethoxyphosphorylmethyl)(ethylami-
nocarbonyl)amino)ethoxyl]-7-methoxyl-4-quinolyl]
oxyl]-3-fluorophenyl]-N1-(4-fluorophenyl)cyclopro-
pane-1,1-dicarboxamide;

N1'-[4-[[6-[3-(diethoxyphosphorylmethyl)(methylami-
nocarbonyl)amino)ethoxyl]-7-methoxyl-4-quinolyl]
oxyl]-3-fluorophenyl]-N1-(4-fluorophenyl)cyclopro-
pane-1,1-dicarboxamide;

N1'-[4-[[6-[3-(diethoxyphosphorylmethyl)(N,N'-dim-
ethylaminocarbonyl)amino)ethoxyl]-7-methoxyl-4-
quinolyl]oxyl]-3-fluorophenyl]-N1-(4-fluorophenyl)
cyclopropane-1,1-dicarboxamide;

N1'-[4-[[6-[3-(diethoxyphosphorylmethyl)(methylsulfo-
nyl)amino)propoxyl]-7-methoxyl-4-quinolyl]oxyl]-3-
fluorophenyl]-N1-(4-fluorophenyl)cyclopropane-1,1-
dicarboxamide;

N1'-[4-[[6-[3-(diethoxyphosphorylmethyl)(ethylsulfonyl)
amino)propoxyl]-7-methoxyl-4-quinolyl]oxyl]-3-fluo-
rophenyl]-N1-(4-fluorophenyl)cyclopropane-1,1-di-
carboxamide;

N1-[4-[[7-[[1-(diethoxyphosphorylmethyl)-4-piperidi-
nyl]methoxyl]-6-methoxyl-4-quinolyl]oxyl]-3-fluo-
rophenyl]-N1'-(4-fluorophenyl)cyclopropane-1,1-di-
carboxamide;

N1-[4-[[7-[[1-(2-diethoxyphosphorylacetyl)-4-piperidi-
nyl]methoxyl]-6-methoxyl-4-quinolyl]oxyl]-3-fluo-
rophenyl]-N1'-(4-fluorophenyl)cyclopropane-1,1-di-
carboxamide;

N1-[4-[[6-[[1-(diethoxyphosphorylmethyl)-4-piperidi-
nyl]methoxyl]-7-methoxyl-4-quinolyl]oxyl]-3-fluo-
rophenyl]-N1'-(4-fluorophenyl)cyclopropane-1,1-di-
carboxamide;

N1-[4-[[6-[[1-(2-diethoxyphosphorylacetyl)-4-piperidi-
nyl]methoxyl]-7-methoxyl-4-quinolyl]oxyl]-3-fluo-
rophenyl]-N1'-(4-fluorophenyl)cyclopropane-1,1-di-
carboxamide.

9. The phosphorus-containing group-substituted quinoline according to claim 1, wherein the compound is selected from the group consisting of one or more of the following compounds:

N1-[4-[[7-[3-(diethoxyphosphorylmethylamino)pro-
poxyl]-6-methoxyl-4-quinolyl]oxyl]-3-fluorophenyl]-
N1'-(4-fluorophenyl)cyclopropane-1,1-dicarboxamide;

N1-[4-[[7-[3-(diethoxyphosphoryl(N-methyl)methy-
lamino)propoxyl]-6-methoxyl-4-quinolyl]oxyl]-3-
fluorophenyl]-N1'-(4-fluorophenyl)cyclopropane-1,1-
dicarboxamide;

N1-[4-[[7-[3-(acetyl(diethoxyphosphorylmethyl)amino)
propoxyl]-6-methoxyl-4-quinolyl]oxyl]-3-fluorophe-
nyl]-N1'-(4-fluorophenyl)cyclopropane-1,1-dicarboxa-
mide;

N1-[4-[[7-[[1-(2-diethoxyphosphorylacetyl)-4-piperidinyl]methoxyl]-6-methoxyl-4-quinolyl]oxyl]-3-fluorophenyl]-N1'-(4-fluorophenyl)cyclopropane-1,1-dicarboxamide;

N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide;

or a racemate or enantiomer thereof.

10. A process of preparing a compound of claim 1 comprising the steps in one of the following Schemes 1-5:

Scheme 1
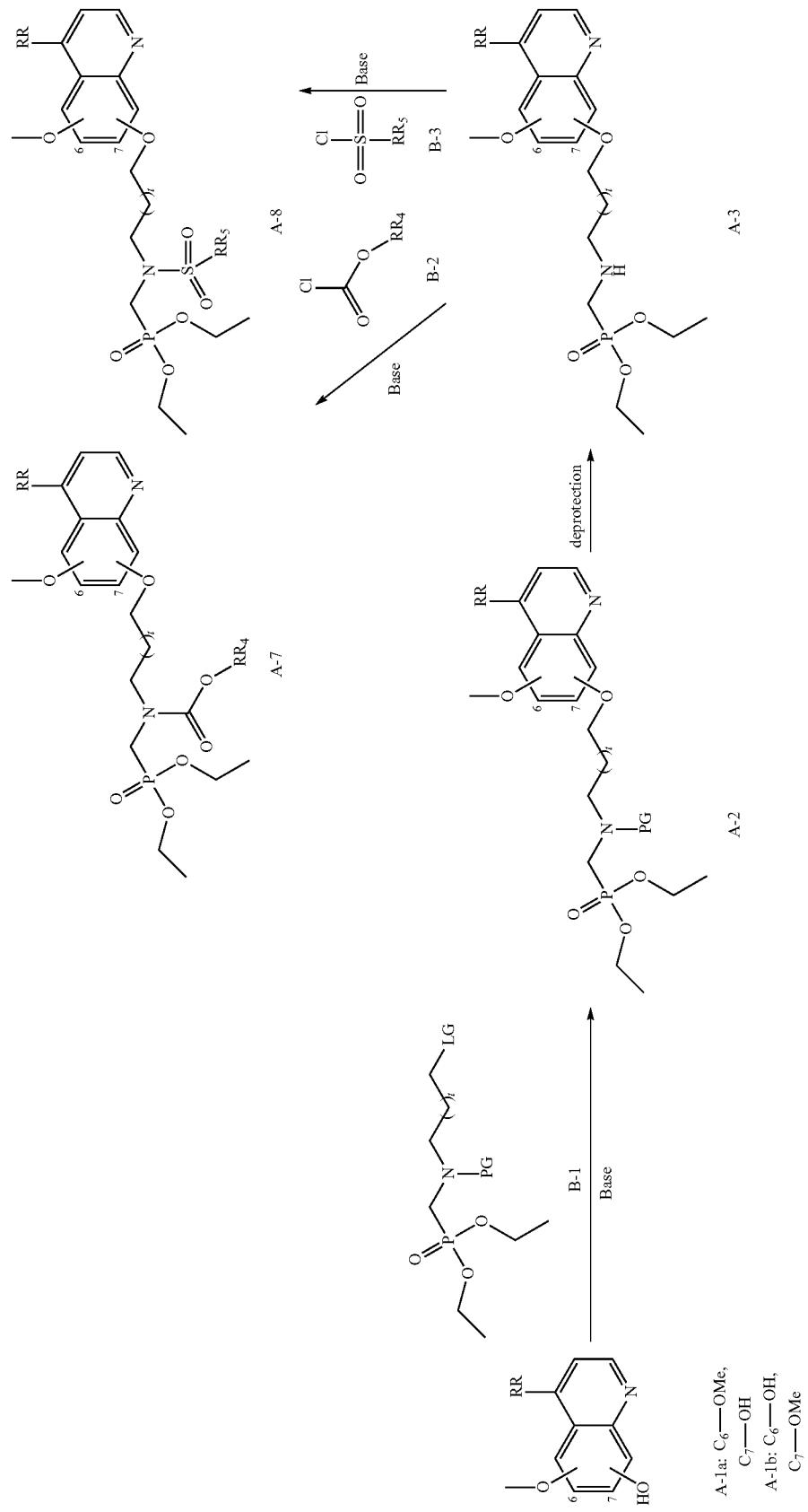
A-1a: $C_6$—OMe, $C_7$—OH
A-1b: $C_6$—OH, $C_7$—OMe

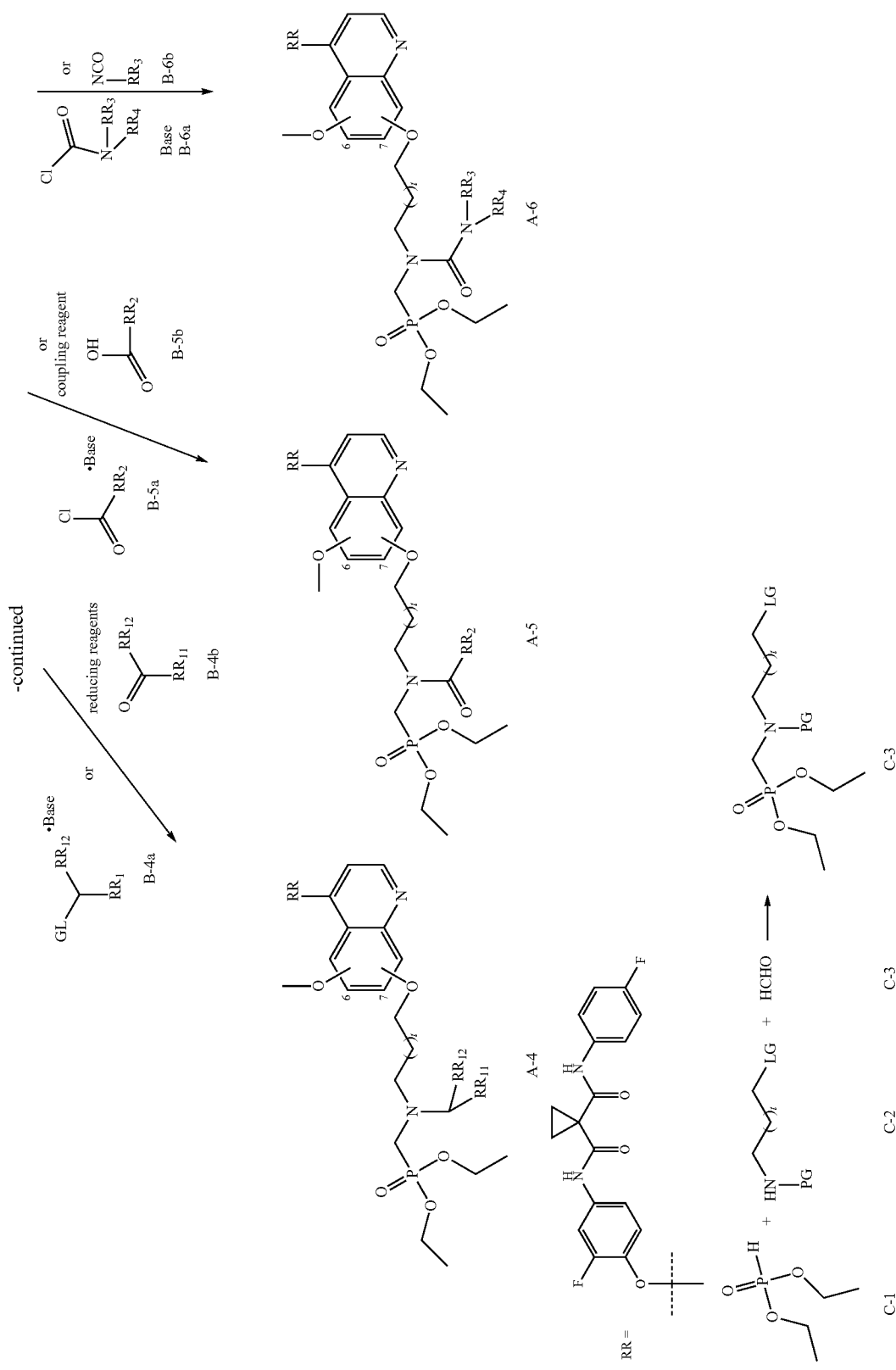

wherein t=0-4;

LG or GL represents common leaving groups in the organic chemistry field;

PG represents common protecting groups in the organic chemistry field;

$RR_1$, $RR_{11}$, $RR_{12}$, $RR_2$, $RR_3$, $RR_4$, or $RR_5$ is each selected from H, $C_{1-6}$ alkyl, $C_{3-6}$ cycloalkyl, $C_6$ aryl, $C_{5-6}$ heteroaryl, or $C_{3-6}$ heterocycloalkyl, and is optionally substituted with H, —CN, —$CF_3$, —$CO_2H$, halogen, $C_{1-6}$ alkyl, $C_{3-6}$ cycloalkyl, $C_{2-6}$ alkenyl, $C_{2-6}$ alkynyl, $C_6$ aryl, $C_{5-6}$ heteroaryl, $C_{3-6}$ heterocycloalkyl, $R^3O$—, $R^3R^4N$—, $R^3S(=O)_m$—, $R^3R^4NS(=O)_m$—, $R^5C(=O)$—, $R^3R^4NC(=O)$—, $R^3OC(=O)$—, $R^5C(=O)O$—, $R^3R^4NC(=O)O$—, $R^5C(=O)NR^3$—, $R^3R^4NC(=O)NR^6$—, $R^3OC(=O)NR^6$—, $R^3S(=O)_mNR^6$—, $R^3R^4NS(=O)_mNR^6$—, $R^3R^4NC(=NR^7)NR^6$—, $R^3R^4NC(=CHNO_2)NR^6$—, $R^3R^4NC(=N-CN)NR^6$—, $R^3R^4NC(=NR^7)$—, $R^3S(=O)(=NR^7)NR^6$—, or $R^3R^4NS(=O)(=NR^7)$), wherein $R^3$, $R^4$, $R^5$, $R^6$ and $R^7$ are each independently selected from hydrogen, $C_{1-6}$ alkyl, $C_{3-6}$ cycloalkyl, $C_6$ aryl, $C_{5-6}$ heteroaryl, or $C_{3-6}$ heterocycloalkyl; when $R^3$ and $R^4$ are attached to the same nitrogen atom, $R^3$ and $R^4$ together with the nitrogen to which they are attached may form a $C_{3-6}$ heterocycloalkyl ring, this $C_{3-6}$ heterocycloalkyl ring may further comprise heteroatom(s) selected from O, N, $S(=O)_m$; and $R^3$, $R^4$, $R^5$, $R^6$ and $R^7$ are each optionally substituted with halogen, CN, $C_{1-6}$ alkyl, or $C_{3-6}$ cycloalkyl; m=0-2;

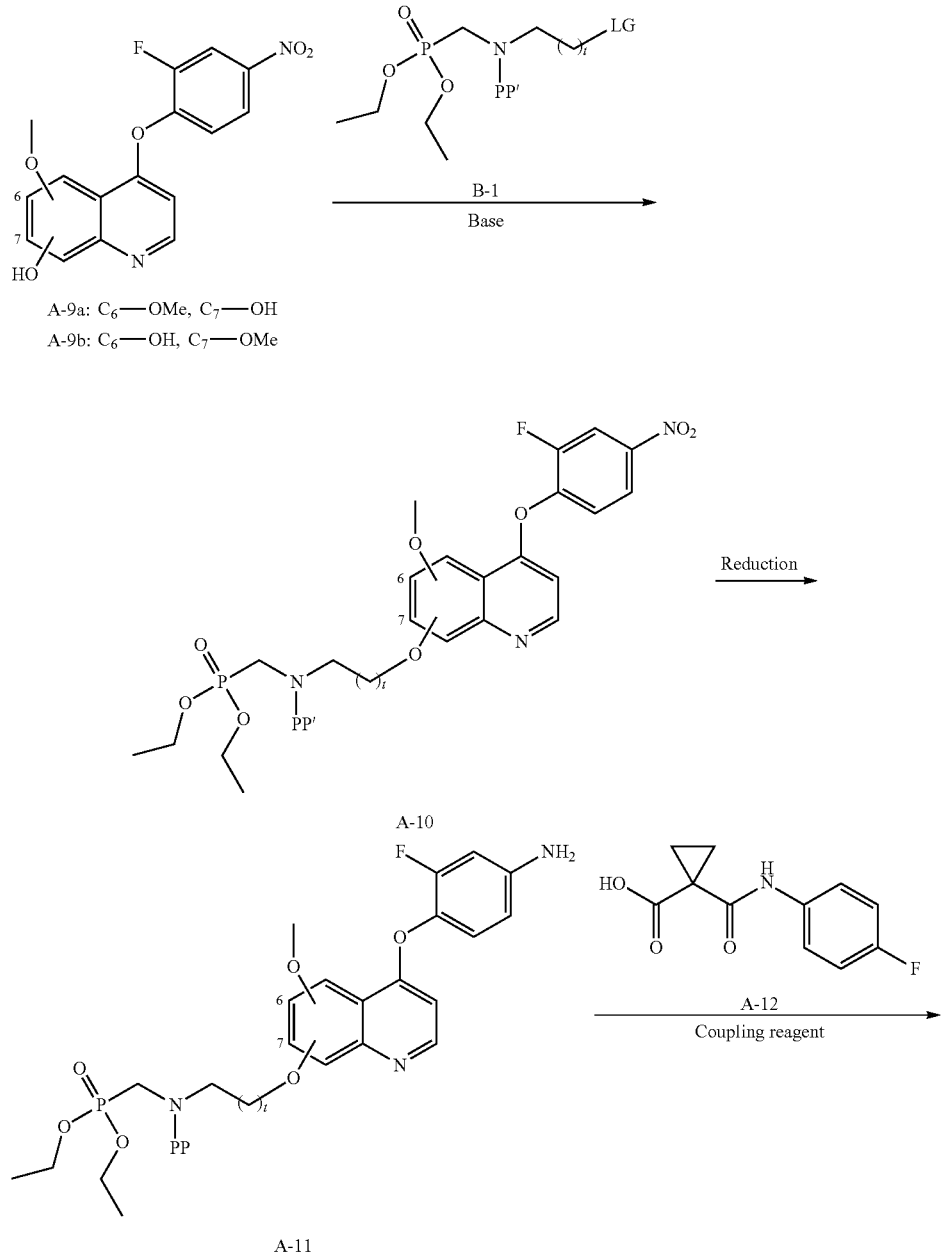

Scheme 2

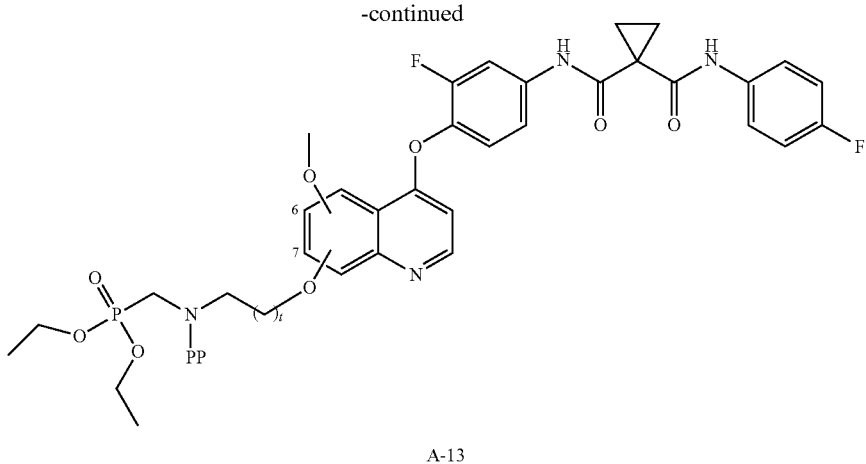
A-13
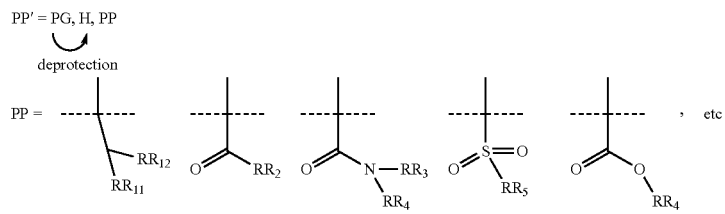
wherein PP' can be any one of PG, H and PP, and PG can be converted into H by deprotection;
Scheme 3
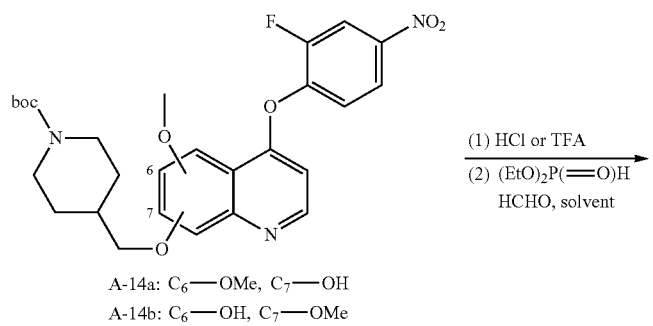
A-14a: C$_6$—OMe, C$_7$—OH
A-14b: C$_6$—OH, C$_7$—OMe
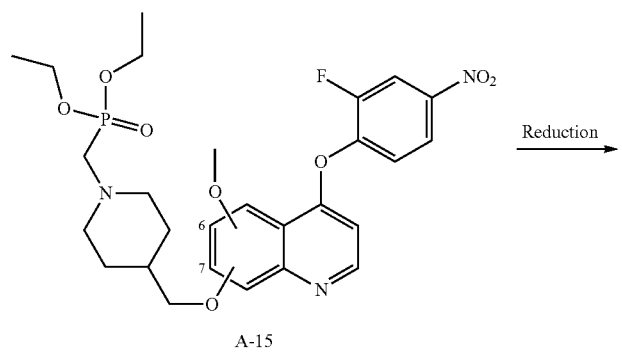
A-15

-continued
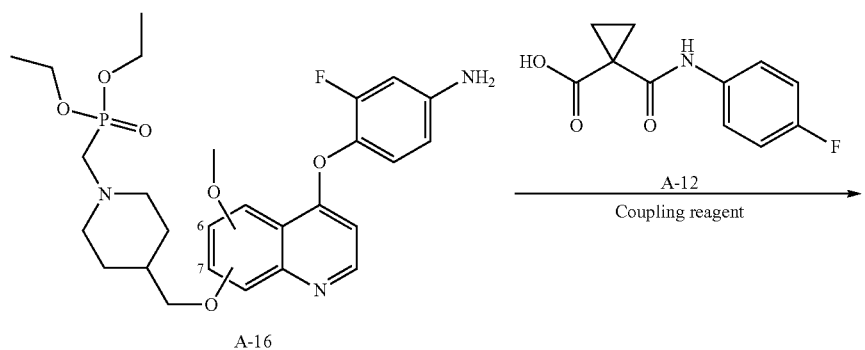
A-16
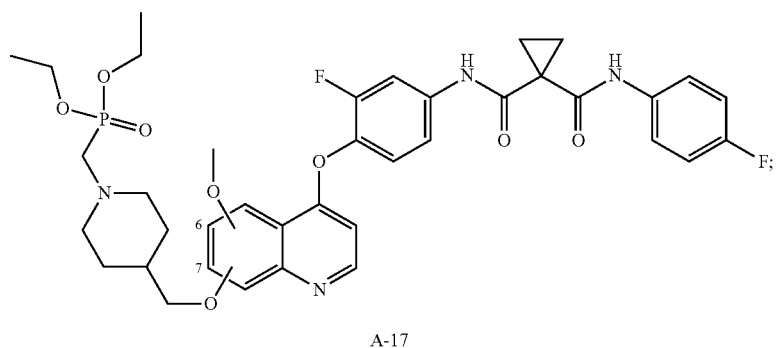
A-17
Scheme 4
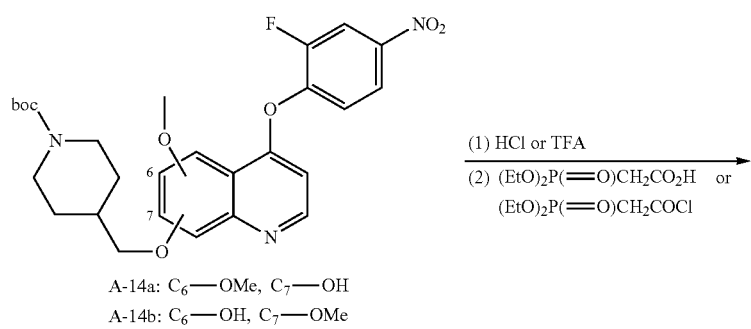
A-14a: C$_6$—OMe, C$_7$—OH
A-14b: C$_6$—OH, C$_7$—OMe
(1) HCl or TFA
(2) (EtO)$_2$P(=O)CH$_2$CO$_2$H or (EtO)$_2$P(=O)CH$_2$COCl
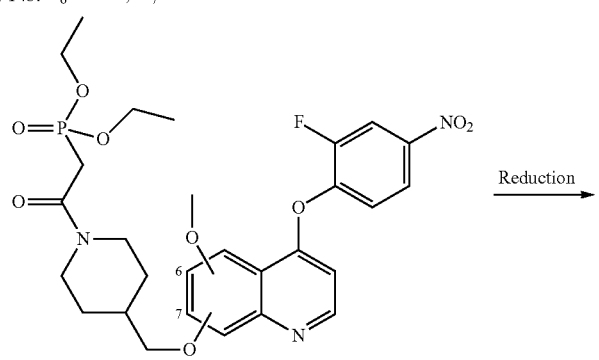
A-18
Reduction -continued
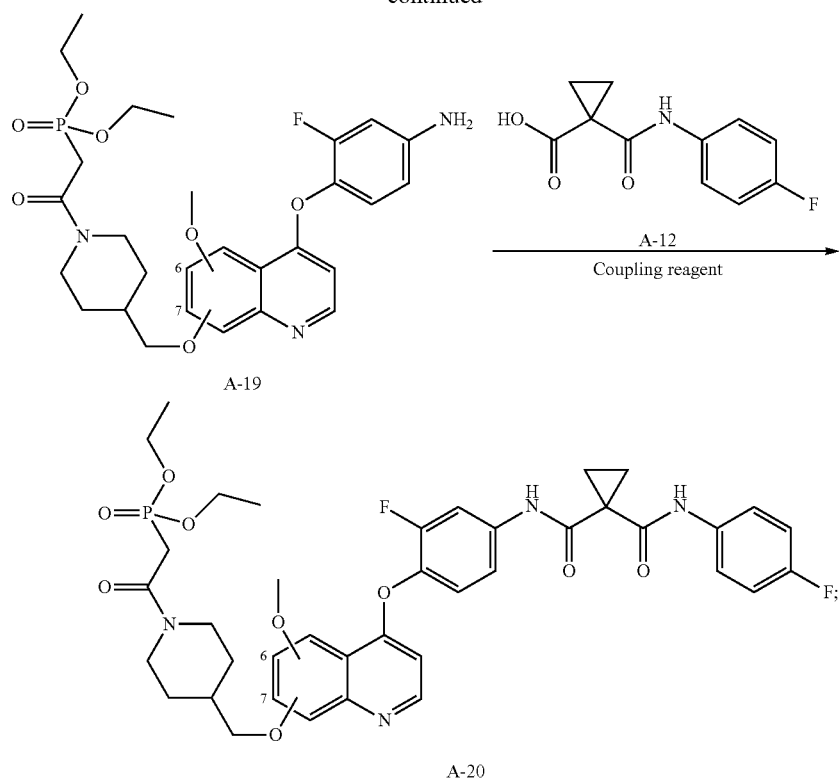
Scheme 5
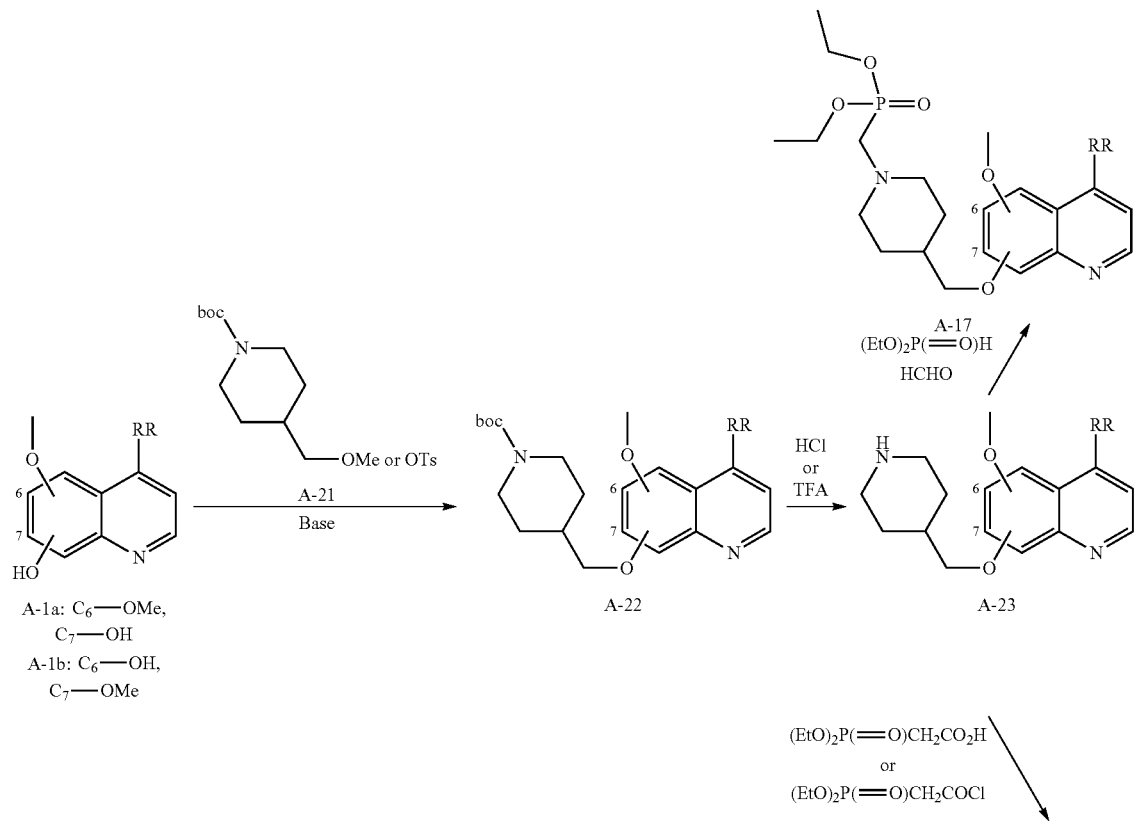

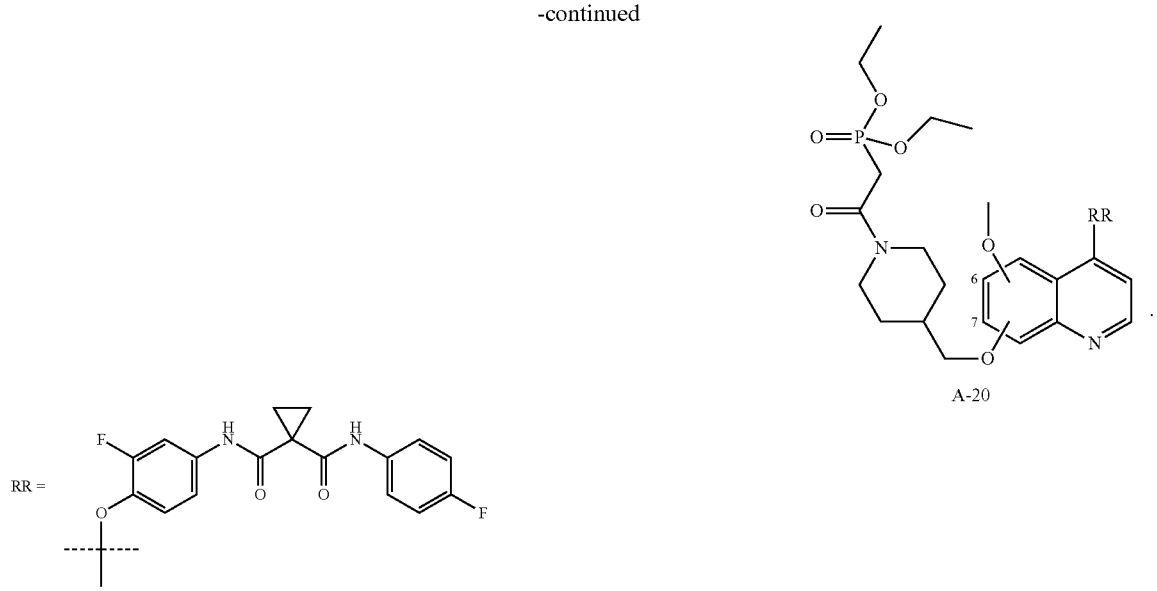

A-20

11. A method of treating at least one tumor associated with the abnormal activities of protein kinase in a subject in need thereof, comprising administering an effective amount of a compound according to claim 1.

12. The method of claim 11, wherein the protein kinase is c-Met, KDR or VEGFR2, RET, PDGFR-β, c-KIT, Flt3, MEK5, DDR1, LOK, CSF1R, EPHA7, EPHA8, EPHB6, MKNK2, BLK, HIPK4, HCK, Flt4.

13. The method of claim 11, wherein the protein kinase is RON, ALK (or Anaplastic Lymphoma Kinase), EGF1R, HER2, HER3, HER4, PDGFR-α, c-fms, FLT1, Src, Frk, Btk, CsK, Abl, Fes, Fps, Fak, AcK, Yes, Fyn, Lyn, Lck, Hck, Fgr, Yrk, PDK1, TAK1, Tie-2, Tie-1, YSK4, TRK A, TRK B, TRK C, SLK, PKN2, PLK4, MST1R, MAP4K, or DDR2.

14. The method of claim 11, wherein the tumor is selected from solid tumor and liquid tumors.

15. The method of claim 11, wherein the tumor comprises: lung cancer, bone cancer, pancreatic cancer, skin cancer, head and neck cancer, skin or intraocular melanoma, uterine cancer, ovarian cancer, rectal cancer, anal region cancer, stomach cancer, colon cancer, breast cancer, fallopian tube cancer, endometrial cancer, cervical cancer, vaginal cancer, vulva cancer, Hodgkin's disease, esophageal cancer, intestinal cancer, endocrine system cancer, thyroid cancer, parathyroid cancer, soft tissue sarcoma, urethral cancer, penile cancer, prostate cancer, chronic or acute leukemia, bladder cancer, kidney or ureter cancer, renal cancer, central nervous system (CNS) tumors, spinal axis tumors, pituitary adenomas, gastrointestinal stromal tumors, colorectal cancer, non-small cell lung cancer, small cell lung cancer, mastocytosis, glioma, sarcoma, lymphoma, or a combination of any thereof.

16. A method of claim 11, comprising administering an effective amount of a compound of formula (I) or pharmaceutically acceptable salt or solvate thereof, or a racemate or enantiomer of the compound of formula (I), or pharmaceutically acceptable salt or solvate thereof.

17. The method of claim 15, further comprising at least one pharmaceutically acceptable carrier.

18. The method of claim 15, wherein the compound is administered in a formulation comprising oral formulation, injectable formulation, anal suppository, nasal inhalation, eye drop, and skin patch.

* * * * *